US007893096B2

(12) United States Patent
Valiante, Jr.

(10) Patent No.: US 7,893,096 B2
(45) Date of Patent: Feb. 22, 2011

(54) USE OF SMALL MOLECULE COMPOUNDS FOR IMMUNOPOTENTIATION

(75) Inventor: Nicholas M. Valiante, Jr., Fremont, CA (US)

(73) Assignee: Novartis Vaccines and Diagnostics, Inc., Emeryville, CA (US)

(*) Notice: Subject to any disclaimer, the term of this patent is extended or adjusted under 35 U.S.C. 154(b) by 0 days.

(21) Appl. No.: 10/814,480

(22) Filed: Mar. 29, 2004

(65) Prior Publication Data

US 2005/0136065 A1    Jun. 23, 2005

Related U.S. Application Data

(60) Provisional application No. 60/458,888, filed on Mar. 28, 2003.

(51) Int. Cl.
| | |
|---|---|
| A01N 43/64 | (2006.01) |
| A01N 43/78 | (2006.01) |
| A01N 43/76 | (2006.01) |
| A01N 43/50 | (2006.01) |
| A01N 43/52 | (2006.01) |
| A01N 43/36 | (2006.01) |
| A01N 43/38 | (2006.01) |
| A61K 31/41 | (2006.01) |
| A61K 31/425 | (2006.01) |
| A61K 31/42 | (2006.01) |
| A61K 31/415 | (2006.01) |
| A61K 31/40 | (2006.01) |

(52) U.S. Cl. .................. 514/359; 514/360; 514/365; 514/367; 514/374; 514/375; 514/377; 514/385; 514/387; 514/408; 514/412

(58) Field of Classification Search ............. 514/637, 514/631, 359, 360, 365, 367, 374, 375, 377, 514/385, 387, 396, 408, 412
See application file for complete search history.

(56) References Cited

U.S. PATENT DOCUMENTS

| | | | | |
|---|---|---|---|---|
| 4,171,353 | A | * | 10/1979 | Ryan ...................... 424/278.1 |
| 6,211,177 | B1 | | 4/2001 | Sperl et al. |
| 6,248,771 | B1 | | 6/2001 | Shenoy et al. |
| 6,399,603 | B1 | | 6/2002 | Jacobs et al. |
| 6,417,194 | B1 | | 7/2002 | Fox et al. |
| 6,596,746 | B1 | * | 7/2003 | Das et al. .................. 514/370 |
| 2002/0022624 | A1 | | 2/2002 | Dinnell et al. |
| 2002/0107392 | A1 | | 8/2002 | Renhowe et al. ............. 544/60 |
| 2003/0147923 | A1 | * | 8/2003 | Klaviniskis et al. ...... 424/246.1 |
| 2004/0087626 | A1 | * | 5/2004 | Renhowe et al. ............ 514/338 |
| 2005/0234083 | A1 | * | 10/2005 | Chamberlain et al. ....... 514/275 |

FOREIGN PATENT DOCUMENTS

| | | |
|---|---|---|
| WO | WO 92/18483 | 10/1992 |
| WO | WO 00/12074 | 3/2000 |
| WO | WO 00/59904 | 10/2000 |
| WO | WO 00/62778 A | 10/2000 |
| WO | WO 00/76505 | 12/2000 |
| WO | WO 02/090375 | 5/2001 |
| WO | WO 01/64668 | 9/2001 |
| WO | WO 01/66539 A | 9/2001 |
| WO | WO 02/22598 | 3/2002 |
| WO | WO02/42273 A2 | 5/2002 |
| WO | WO02/44156 A2 | 6/2002 |
| WO | WO02/076960 A1 | 10/2002 |
| WO | WO 02/083624 | 10/2002 |
| WO | WO02/094808 A1 | 11/2002 |
| WO | WO 03/000694 | 1/2003 |
| WO | WO 03/074515 A1 | 9/2003 |
| WO | WO 03/082272 | 10/2003 |
| WO | WO03/082272 A1 | 10/2003 |
| WO | WO 2004/018419 A2 | 3/2004 |
| WO | WO 2004/085425 A1 | 10/2004 |
| WO | WO2004/985425 A1 | 10/2004 |

OTHER PUBLICATIONS

Ukrainets et al., "4-Hydroxy-2-Quinolones. 32. Synthesis and Antithyroid Activity of Thio Analogs of 1H-2-Oxo-3-(2-Benzimidazolyl)-4-Hydroxyquinoline" *Chemistry of Heterocyclic Compounds* 33(5):600-604, 1997.

Ukrainets et al., "4-Hydroxy-2-Quinolones 7 Synthesis and Biological Properties of 1-R-3-(2-Benzimidazolyl)-4-Hydroxy-2-Quinolones" *Chemistry of Heterocyclic Compounds* 29(1):92-94, 1993.

Sato et al., "Characteristics of Antitumor Activity of 3,4-dihydro-6-[4-(3,4-dimethoxybenzoyl)-1-piperazinyl)- . . . " *Cancer Letters* 91:1-9, 1995.

Oyaizu et al., "Inhibition of CD4 Cross-Linking-Induced Lymphoyctes Apoptosis by Vesnarinone as a Novel Immunomodulating Agent . . . " *Blood* 87(6):2361-2368, Mar. 15, 1996.

Toldy et al., "3,4,5-Trimethoxybenzoylderivative, Eine Neue Verbindungsgruppe Mit Antiulzerogener Wirkung" *Acta Chimica Academiae Scientiarum Hungaricae Tomus* 49(3):265-286, 1966.

Sato et al., "Induction of Tumour Differentiation and Apoptosis and Le$^y$ Antigen Expression in Treatment with Differentiation-Inducing Agent, Vesnarinone, of a Patient with Salivary Adenoid Cystic Carcinoma" *Apoptosis* 2:106-113, 1997.

Petigara et al., "Synthesis and Central Nervous System Depressant Activity of New Piperazine Derivatives" 11:332-336, Mar. 1, 1968.

Yamaguchi, "Vesnarinone Inhibits Growth of Large Cell Lung Cancer Cell Lines via Induction of Apoptosis" *Med. J. Kagoshima Univ.* 51(4):67-75. Feb. 2000.

* cited by examiner

*Primary Examiner*—Yong S Chong
(74) *Attorney, Agent, or Firm*—Helen Lee; Otis Littlefield

(57) ABSTRACT

The invention provides immunostimulatory compositions comprising a small molecule immuno-poteniator (SMIP) compound and methods of administration thereof. Also provided are methods of administering a SMIP compound in an effective amount to enhance the immune response of a subject to an antigen. Further provided are novel compositions and methods of administering SMIP compounds alone or in combination with another agent for the treatment of cancer, infectious diseases and/or allergies/asthma.

10 Claims, No Drawings

USE OF SMALL MOLECULE COMPOUNDS FOR IMMUNOPOTENTIATION

FIELD OF THE INVENTION

This invention relates generally to compounds capable of stimulating or modulating an immune response in a subject. More particularly the invention pertains to novel combinations of antigens with small molecules to be used in vaccine therapies. The compounds in one embodiment can be used as adjuvants for prophylactic and therapeutic vaccines for infectious diseases and cancer. In another embodiment they can be used as immunotherapeutics for cancer, infectious diseases and/or allergy/asthma either alone or in combination with existing therapies.

BACKGROUND OF THE INVENTION

Immune response to certain antigens that are otherwise weakly antigenic can be enhanced through the use of vaccine adjuvants. Such adjuvants potentiate the immune response to specific antigens and are therefore the subject of considerable interest and study within the medical community.

Research has permitted development of vaccines possessing antigenic epitopes that were previously impossible to produce. For example, currently available vaccine candidates include synthetic peptides mimicking streptococcal, gonococcal, and malarial antigens. These purified antigens are generally weak antigens, however, that require adjuvants in order to evoke protective immunity. However, conventional vaccine adjuvants possess a number of drawbacks that limit their overall use and effectiveness.

Again, this is fine for vaccines but not other uses.

Substances that stimulate immune cells in vitro exhibit similar immuno-stimulatory effects in vivo. These compounds, such as recombinant cytokines, pathogen products (e.g. toxins, lipids, proteins/peptides, carbohydrates and nucleic acids) and other mammalian-derived immunostimulatory molecules (e.g. heat shock proteins, complement, immune complexes and proteoglycans) all induce a measurable pro-inflammatory response both in vitro and in vivo.

Historically, the classic adjuvants have been Freund's complete or incomplete (i.e., without mycobacteria) adjuvants. Edmund Coley described the potential of Coley's toxin for cancer immuno-therapy. Other materials, such as mineral oil and aluminum hydroxide, have also been used as adjuvants, but they invariably suffer from disadvantages. For example, mineral oil is known to produce tissue irritation and to be potentially oncogenic. Alum, the only approved adjuvant in the United States, also induces granulomas at the inoculation site and furthermore it does not effectively induce cell-mediated immunity. Moreover, many of the adjuvants currently available have limited utility because they contain components, that are not metabolizable in humans. Additionally, most adjuvants are difficult to prepare in that they may require time consuming procedures and the use, in some cases, of elaborate and expensive equipment to formulate a vaccine and adjuvant system.

Immunological adjuvants are described in "Current Status of Immunological Adjuvants", Ann. Rev. Immunol., 1986, 4, pp. 369-388, and "Recent Advances in Vaccine Adjuvants and Delivery Systems" by Derek T O'Hagan and Nicholas M. Valiente. See also U.S. Pat. Nos. 4,806,352; 5,026,543; and 5,026,546 for disclosures of various vaccine adjuvants appearing in the patent literature.

Compounds are described in issued U.S. Pat. Nos. 4,547,511 and 4,738,971 with the general structure (a):

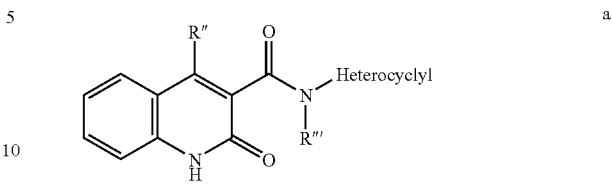

for the treatment of disorders responsive to agents that enhance cell-mediated immunity. An essential component of the molecule as described in the cited patents is the amide substituent as shown in structure (a). The invention did not contemplate combinations with antigens.

Immunostimulatory oligonucleotides and polynucleotides are described in PCT WO 98/55495 and PCT WO 98/16247. U.S. Patent Application No. 2002/0164341 describes adjuvants including an unmethylated CpG dinucleotide (CpG ODN) and a non-nucleic acid adjuvant. U.S. Patent Application No. 2002/0197269 describes compositions comprising an antigen, an antigenic CpG-ODN and a polycationic polymer.

Additionally, issued U.S. Pat. Nos. 4,689,338, 5,389,640, 5,268,376, 4,929,624, 5,266,575, 5,352,784, 5,494,916, 5,482,936, 5,346,905, 5,395,937, 5,238,944, 5,525,612, WO99/29693 and U.S. Ser. No. 09/361,544 disclose compounds of the general structure (b):

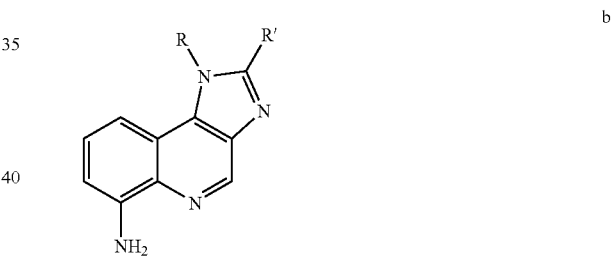

for the use as "immune response modifiers."

There has been an effort to find new immune modulators for use as adjuvants for vaccines and immunotherapies that would overcome the drawbacks and deficiencies of conventional immune modulators. In particular, an adjuvant formulation that elicits potent cell-mediated and humoral immune responses to a wide range of antigens in humans and domestic animals, but lacking the side effects of conventional adjuvants and other immune modulators, would be highly desirable. This need could be met by small molecule immune potentiators (SMIPs) because the small molecule platform provides diverse compounds for the selective manipulation of the immune response, necessary for increasing the therapeutic index immune modulators.

Furthermore, it would be desirable to provide novel compounds with a varied capacity to alter levels and/or profiles of cytokine production in human immune cells. Compounds with structural disparities will often times elicit a desired response through a different mechanism of action, or with greater specificity to a target, such as a dendritic cell, modulating potency and lowering side effects when administered to a patient.

The immunosuppressive effect of cytostatic substances has rendered them useful in the therapy of autoimmune diseases such as multiple sclerosis, psoriasis and certain rheumatic diseases. Even here their beneficial effect has to be weighed against the serious side effects that necessitate too low dosages and/or interruption of the treatment.

It is the object of the present invention to provide a combination of active substances that results in a significantly improved cytostatic or cytotoxic effect as compared to conventional cytostatics given alone, e.g. vincristin, methotrexate, cisplatin etc. Thereby, chemotherapies may be offered that combine increasing efficiency with a large reduction of side effects and therapeutic doses. Thus, the therapeutic efficiency of known cytostatic drugs is increased. Also, certain cell lines that are insensitive to chemotherapeutic treatment may become susceptible to chemotherapy by applying the combination of active substances.

Therapeutics that could serve to augment natural host defenses against viral and bacterial infections, or against tumor induction and progression, with reduced cytotoxicity would be very beneficial. The present invention provides such therapeutic agents, and further provides other related advantages.

All of the aforementioned documents are incorporated by reference as if fully set forth herein.

SUMMARY OF THE INVENTION

The instant invention provides novel immune potentiators, immunogenic compositions, novel compounds and pharmaceutical compositions, and novel methods of administering a vaccine, by administering small molecule immune potentiators in combination with antigens. The invention further provides compositions, novel compounds and pharmaceutical compositions, for use in the treatment of cancer, infectious diseases, allergies, and asthma.

The SMIP compounds used in the methods and compositions of the invention are inexpensive to produce and easy to administer. They have potential for finer specificity compared to existing immunostimulants, thus providing improved efficacy and safety profiles.

As adjuvants, the SMIP compounds are combined with numerous antigens and delivery systems to form a final vaccine product.

As immuno-therapeutics, the SMIP compounds are used alone or in combination with other therapies (e.g. anti-virals, anti-bacterials, other immune modulators or in therapeutic vaccine antigens) for treatment of chronic infections such as HIV, HCV, HBV, HSV, and *H. pylori*, as well as medicaments for the reduction of tumor growth.

As immunotherapeutics, the SMIP compounds also may be used for the treatment of cancer either alone or in combination with other anti-cancer therapies (e.g. chemotherapeutic agents, mabs or other immune potentiators). In addition, certain SMIPs with the capapcity to induce Type 1 cytokines (e.g. IL-12, TNF or IFN's) could be useful for the treatment of allergies or asthma due to their capacity to steer the immune response towards more benign sequelae. The SMIP compounds may be used for example for the treatment of BCG, cholera, plague, typhoid, hepatitis B infection, influenza, inactivated polio, rabies, measles, mumps, rubella, oral polio, yellow fever, tetanus, diphtheria, hemophilus influenzae b, meningococcus infection, and pneumococcus infection. The SMIP compounds may be used in an anti cell proliferative effective amount for the treatment of cancer. The SMIP compounds may also be used in anti-Th2/Type2 cytokine amount for the deviation of allergic/asthmatic immune responses.

In another embodiment methods of treating cancer are provided wherein known anticancer agents are combined with SMIP compounds to reduce tumor growth in a subject. A number of suitable anticancer agents are contemplated for use in the methods of the present invention and are described more thoroughly in the detailed description.

In accordance with the present invention, there is provided a method of inhibiting tumor cell growth in a subject, which method comprises administering to said subject an effective dose of a combination containing at least a SMIP and a MAb, wherein said combination is more effective to inhibit such cell growth than when said MAb is administered individually. Further provided are methods of treating cancer with said combination comprising an additional SMIP compound or MAb, as well as methods of administration to a subject in need thereof.

Applicants have discovered a broad class of compounds that unexpectedly shows potent stimulation of cytokine activity in human peripheral blood mononuclear cells and as immunotherapeutics and/or vaccine adjuvants in combination with an antigen(s), will provide effective treatments for disorders described herein and those apparent to one skilled in the art.

In one embodiment, the SMIP compounds used in the methods and compositions of the invention are represented by Formula (I):

X—Y—Z  (I)

wherein,
X is selected from the group consisting of substituted or unsubstituted alkyl, aryl, heteroaryl, fused arylaryl, fused heteroarylaryl, fused heteroarylheteroaryl, unfused arylaryl, unfused heteroarylaryl, unfused heteroarylheteroaryl and heterocyclyl groups;
Y is a linking moiety; and,
Z is selected from the group consisting of substituted or unsubstituted aryl, heteroaryl, fused arylaryl, fused heteroarylaryl, and fused arylheteroaryl groups;

wherein, upon administration of compound I to a patient, human peripheral blood mononuclear cells are stimulated to produce cytokines.

Provided is a method of enhancing an immune response in a subject to an antigen, the method comprising administering to said subject an antigen and an effective amount of a SMIP compound, or a salt, ester or prodrug thereof, to enhance the immune response to said antigen. The antigen is associated, for example, with a disease such as BCG, cholera, plague, typhoid, hepatitis B infection, influenza, inactivated polio, rabies, measles, mumps, rubella, oral polio, yellow fever, tetanus, diphtheria, hemophilus influenzae b, meningococcus infection, and pneumococcus infection. The antigen could be any antigen known in the art including any antigen disclosed herein. The immune response is, for example, the cellular production of one or more cytokines.

Also provided is a pharmaceutical composition comprising an antigen and a SMIP compound capable of enhancing an immune response in a host to said antigen. The SMIP compound may be present in a concentration effective to enhance an immune response to an antigen. The composition may further comprise an aqueous carrier. The antigen may be associated with a disease such as BCG, cholera, plague, typhoid, hepatitis B infection, influenza, inactivated polio, rabies, measles, mumps, rubella, oral polio, yellow fever, tetanus, diphtheria, hemophilus influenzae b, meningococcus infection, and pneumococcus infection. The antigen could be any antigen known in the art including any antigen disclosed herein. The immune response is for example the cellular production of one or more cytokines leading to the enhancement of antigen-specific B (e.g. antibodies) and T cell responses and immunologic memeory.

In one embodiment, the present invention is for an immune-response eliciting pharmaceutical composition comprising a SMIP compound of formula (I):

Wherein X is selected from the group consisting of substituted or unsubstituted alkyl, aryl, heteroaryl, fused arylaryl, fused heteroarylaryl, fused heteroarylheteroaryl, unfused arylaryl, unfused heteroarylaryl, unfused heteroarylheteroaryl and heterocyclyl groups; Y is a linking moiety; and, Z is selected from the group consisting of substituted or unsubstituted aryl, heteroaryl, fused arylaryl, fused heteroarylaryl, and fused arylheteroaryl, or a pharmaceutically acceptable salt, ester, or prodrug thereof and a pharmaceutically acceptable excipient. In this embodiment, the administration of the pharmaceutical composition enhances an immune response in a subject. In an embodiment of the invention, the immune response is about 1.2 times the non-enhanced response. In a further embodiment of the invention, the immune response is about 1.3 times the non-enhanced immune response. In a further embodiment of the invention, the immune response is about 1.4 times the non-enhanced immune response. In a further embodiment of the invention, the immune response is about 1.5 times the non-enhanced immune response. In a further embodiment of the invention, the immune response is about 2 times the non-enhanced immune response. In a further embodiment of the invention, the immune response is about 3 times the non-enhanced immune response. In a further embodiment of the invention, the immune response is about 4 times or greater the non-enhanced immune response. The magnitude of enhancement of an immune response can be determined by the methods described herein.

In another embodiment, Y is a covalent bond or a linking moiety selected from the group consisting of —CO—, —O—, —S—, —CH$_2$—, and —NH—.

In a further embodiment, the SMIP compound is compound of formula (II):

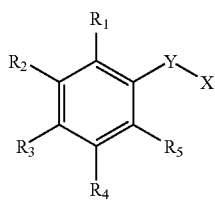

Wherein Y is absent or a linking moiety; X is selected from the group consisting of substituted or unsubstituted alkyl, aryl, heteroaryl, fused arylaryl, fused heteroarylaryl, fused heteroarylheteroaryl, unfused arylaryl, unfused heteroarylaryl, unfused heteroarylheteroaryl and heterocyclyl groups;

R$_1$ is selected from the group consisting of H, halogen, hydroxy, amino, nitro, cyano, carboxylic acid, and substituted or unsubstituted alkyl, alkenyl, alkynyl alkylamino, aminoalkyl, alkylcarbonyloxy, alkoxycarbonyl, aminocarbonyl, alkylaminocarbonyl, carbonylamino, alkylcarbonylamino, alkoxy, alkoxyalkyl, carbocyclyl, heterocyclyl, aryl, heteroaryl, fused arylaryl, unfused arylaryl fused heteroarylaryl, unfused heteroarylaryl, fused arylheteroaryl and unfused arylheteroaryl groups;

R$_2$ is selected from the group consisting of H, halogen, hydroxy, amino, nitro, cyano, carboxylic acid, and substituted or unsubstituted alkyl, alkenyl, alkynyl alkylamino, aminoalkyl, alkylcarbonyloxy, alkoxycarbonyl, aminocarbonyl, alkylaminocarbonyl, carbonylamino, alkylcarbonylamino, alkoxy, alkoxyalkyl, carbocyclyl, heterocyclyl, aryl, heteroaryl, fused arylaryl, unfused arylaryl fused heteroarylaryl, unfused heteroarylaryl, fused arylheteroaryl and unfused arylheteroaryl groups; or, R$_2$ is taken together with R$_3$ to form a substituted or unsubstituted 5-7 membered ring consisting of all carbon atoms or 1-2 heteroatoms selected from the group consisting of O, S, N; or, R$_3$ is selected from the group consisting of H, halogen, hydroxy, amino, nitro, cyano, carboxylic acid, and substituted or unsubstituted alkyl, alkenyl, alkynyl alkylamino, aminoalkyl, alkylcarbonyloxy, alkoxycarbonyl, aminocarbonyl, alkylaminocarbonyl, carbonylamino, alkylcarbonylamino, alkoxy, alkoxyalkyl, carbocyclyl, heterocyclyl, aryl, heteroaryl, fused arylaryl, unfused arylaryl fused heteroarylaryl, unfused heteroarylaryl, fused arylheteroaryl and unfused arylheteroaryl groups; R$_4$ is selected from the group consisting of H, halogen, hydroxy, amino, nitro, cyano, carboxylic acid, and substituted or unsubstituted alkyl, alkenyl, alkynyl alkylamino, aminoalkyl, alkylcarbonyloxy, alkoxycarbonyl, aminocarbonyl, alkylaminocarbonyl, carbonylamino, alkylcarbonylamino, alkoxy, alkoxyalkyl, carbocyclyl, heterocyclyl, aryl, heteroaryl, fused arylaryl, unfused arylaryl fused heteroarylaryl, unfused heteroarylaryl, fused arylheteroaryl and unfused arylheteroaryl groups; and R$_5$ is selected from the group consisting of H, halogen, hydroxy, amino, nitro, cyano, carboxylic acid, and substituted or unsubstituted alkyl, alkenyl, alkynyl alkylamino, aminoalkyl, alkylcarbonyloxy, alkoxycarbonyl, aminocarbonyl, alkylaminocarbonyl, carbonylamino, alkylcarbonylamino, alkoxy, alkoxyalkyl, carbocyclyl, heterocyclyl, aryl, heteroaryl, fused arylaryl, unfused arylaryl fused heteroarylaryl, unfused heteroarylaryl, fused arylheteroaryl and unfused arylheteroaryl groups, or a pharmaceutically acceptable salt, ester, or prodrug thereof.

In another embodiment, Y is a linking moiety is selected from the group consisting of —CO—, —O—, —S—, —CH$_2$—, —NH—; with the proviso that an aminocarbonyl group is not formed between the attachment of Y and X.

In a further enbodiment, the pharmaceutical composition comprises a SMIP compound that is selected from the group consisting of an acylpiperazine, an indoledione, a tetrahydroisoquinoline, a benzocyclodione, an amino azavinyl compound, a thiosemicarbazone, a lactam, an aminobenzimidazole quinolinone, a hydropthalamide, a benzophenone, an isoxazole, a sterol, a quinazolinone, a pyrole, an anthraquinone, a quinoxaline, a triazine, an benzazole, and a pyrazolopyrimidine, or a pharmaceutically acceptable salt, ester, or prodrug thereof.

In an embodiment of the invention, the pharmaceutical composition comprises a SMIP compound that is an acylpiperazine compound of formula (III):

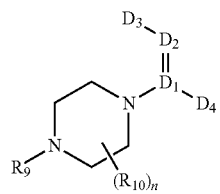

Wherein R$_9$ is selected from the group consisting of substituted or unsubstituted aryl, heteroaryl, arylalkyl, arylalkenyl, heteroarylalkyl, and heteroarylalkenyl; $R_{10}$ is substituted or unsubstituted alkyl; n is an integer from 0-2; and if $D_1$ is carbon then $D_2$ is oxygen, $D_3$ is absent, and $D_4$ is selected from the group consisting of substituted or unsubstituted aryl, heteroaryl, carbocycyl, alkoxyaryl, fused arylaryl, fused arylheteroaryl, and fused heteroarylaryl; or, if $D_1$ is nitrogen than $D_2$ is nitrogen, $D_4$ is absent, and $D_3$ is selected from the group consisting of substituted or unsubstituted aryl, heteroaryl, carbocycyl, alkoxyaryl, fused arylaryl, fused arylheteroaryl, and fused heteroarylaryl, or a pharmaceutically acceptable salt, ester, or prodrug thereof.

In a further embodiment of the invention, the pharmaceutical composition comprises a SMIP compound that is an indoledione compound of formula (IV):

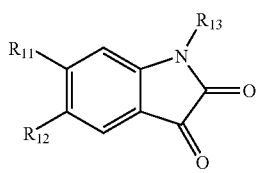

IV

Wherein $R_{11}$ and $R_{12}$ are independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl. $R_{13}$ is selected from the group consisting of substituted or unsubstituted aryl, heteroaryl, arylalkyl, heteroarylalkyl, heterocyclyl, heterocyclylalkyl, and alkylbenzyl, or a pharmaceutically acceptable salt, ester, or prodrug thereof.

In another embodiment of the invention, the pharmaceutical composition comprises a SMIP compound that is a tetrahydraisoquinoline compound is a compound of Formula (V):

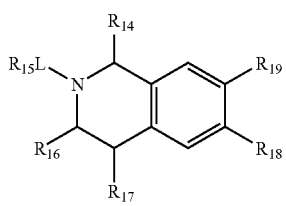

V

Wherein L is a covalent bond or selected from the group consisting of —CH$_2$—, —CO—, —O—, —S—, CHF, —NH—, —NR$_{20}$—, where $R_{20}$ is lower alkyl; $R_{14}$ is selected from the group consisting of hydrogen, halogen, and substituted or unsubstituted alkyl; $R_{15}$ is selected from the group consisting of substituted or unsubstituted carbocyclyl, aryl, arylalkyl, alkoxyaryl, heteroaryl, heterocyclyl; $R_{16}$ is selected from the group consisting of hydrogen, halogen, and substituted or unsubstituted alkyl; $R_{17}$ is selected from the group consisting of hydrogen, halogen, and substituted or unsubstituted alkyl; $R_{18}$ and $R_{19}$ are independently selected from the group consisting of H, hydroxy, halogen, alkoxy, amino, unsubstituted alkyl, substituted alkyl, and alkylamino, or a pharmaceutically acceptable salt, ester, or prodrug thereof.

In an additional embodiment of the invention, the pharmaceutical composition comprises a SMIP compound that is a benzocyclodione compound of formula (VI):

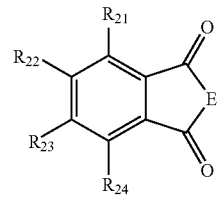

VI

Wherein E is selected from the group consisiting of NR$_{25}$ or CR$_{26}$R$_{27}$; $R_{21}$, $R_{23}$, and $R_{24}$ are independently selected from the group consisting of H, hydroxy, halogen, alkoxy, amino, unsubstituted alkyl, substituted alkyl, and alkylamino. $R_{22}$ is selected from the group consisting or H, hydroxy, halogen, alkoxy, amino, and unsubstituted or substituted alkyl, and alkylamino, arylalkyl, heteroarylalkyl, aryl, heteroaryl, arylcarbonyl, heterocyclyl, heterocyclylalkyl, and heteroarylcarbonyl; $R_{25}$ is selected from the group consisting of substituted or unsubstituted aryl, heteroaryl, heterocyclyl, carbocyclyl, arylalkyl, heteroarylalkyl, and heterocyclyalkyl; $R_{26}$ is selected from the group consisiting of H, halogen, hydroxy, amino, and substituted or unsubstituted alkyl, carbonylalkyl, and alkylcarbonylalkyl; $R_{27}$ is selected from the group aryl, arylalkyl, heteroarylalkyl, heterocyclyl, heterocyclylalkyl, carbocyclyl, arylcarbonylalkyl, and arylalkylcarbonyl, or a pharmaceutically acceptable salt, ester, or prodrug thereof.

In an embodiment of the invention, the pharmaceutical composition comprises a SMIP compound that is an aminoazavinyl compound of formula (VII):

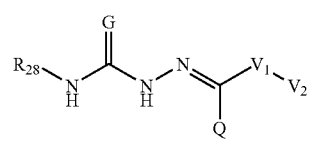

VII

Wherein G is either S or NH; $R_{28}$ is selected from the group consisting of H, and substituted or unsubstituted alkyl, aryl, heteroaryl, heteroarylalkyl, arylalkyl, carbocyclyl, carbocyclylalkyl, heterocyclyl, and heterocyclylalkyl; Q is selected from the group consisting of hydrogen, substituted alkyl, unsubstituted alkyl, and aryl, substituted aryl, heteroaryl, substituted heteroaryl, heterocyclyl, substituted heterocyclyl, biaryl, substituted biaryl, arylheteroaryl, substituted arylheteroaryl, heteroarylheteroaryl, and substituted heteroarylheteroaryl; $V_1$ is selected from the group consisting of alkyl, substituted alkyl, aryl, substituted aryl, arylalkyl, substituted arylalkyl, heteroaryl, substituted heteroaryl, heteroarylalkyl, substituted heteroarylalkyl, alkoxy, substituted alkoxy, aminocarbonyl, alkoxycarbonyl, carboxyl sulfonyl, methanesulfonyl, and substituted or unsubstituted alkylcarbonyl, arylcarbonyl, aralkylcarbonyl, heteroarylcarbonyl, heteroaralkylcarbonyl, alkylcarbonyloxy, arylcarbonyloxy, aralkylcarbonyloxy, heteroarylcarbonyloxy, heteroaralkylcarbonyloxy, alkylaminocarbonyloxy, arylaminocarbonyloxy, formyl, loweralkylcarbonyl, loweralkoxycarbonyl, aminocarbonyl, aminoaryl, alkylsulfonyl, sulfonamido, aminoalkoxy, alkylamino, heteroarylamino, alkylcarbonylamino, alkylaminocarbonylamino, arylaminocarbonylamino, aralkylcarbonylamino, heteroarylcarbonylamino, arylcarbonylamino, cycloamidino, cycloalkyl, cycloimido, arylsulfonyl and arylsulfonamido; $V_2$ is selected from the group consisting of hydrodgen, halogen, alkyl, substituted alkyl, aryl, substituted aryl, arylalkyl, substituted arylalkyl, heteroaryl, substituted heteroaryl, heteroarylalkyl, substituted heteroarylalkyl, alkoxy, substituted alkoxy, aminocarbonyl, alkoxycarbonyl, carboxyl sulfonyl, methanesulfonyl, and substituted or unsubstituted alkylcarbonyl, arylcarbonyl, aralkylcarbonyl, heteroarylcarbonyl, heteroaralkylcarbonyl, alkylcarbonyloxy, arylcarbonyloxy, aralkylcarbonyloxy, heteroarylcarbonyloxy, heteroaralkylcarbonyloxy, alkylaminocarbonyloxy, arylaminocarbonyloxy, formyl, loweralkylcarbonyl, loweralkoxycarbonyl, aminocarbonyl, aminoaryl, alkylsulfonyl, sulfonamido, aminoalkoxy, alkylamino, heteroarylamino, alkylcarbonylamino, alkylaminocarbonylamino, arylaminocarbonylamino, aralkylcarbonylamino, heteroarylcarbonylamino, arylcarbonylamino, cycloamidino, cycloalkyl, cycloimido, arylsulfonyl and arylsulfonamido, or a pharmaceutically acceptable salt, ester, or prodrug thereof.

In a further embodiment of the invention, the pharmaceutical composition comprises a SMIP compound that is an ABIQ compound of formula (VIII):

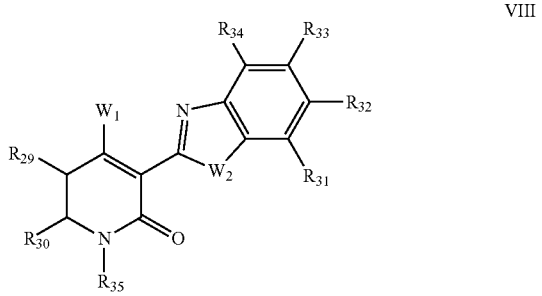

VIII

Wherein $W_1$ is selected from the group consisting of —OH, —$OR_{36}$ groups, —$NR_{37}R_{38}$; $W_2$ is selected from the group consisting of O, S, and $NR_{39}$ groups; $R_{29}$ and $R_{30}$ join to form a 5 to 6 membered substituted or unsubstituted ring comprising all carbon atoms or at least one O, N, or S atom; $R_{35}$ and $R_{39}$ may be the same or different and are selected from the group consisting of H, —OH substituted and unsubstituted alkyl groups, substituted and unsubstituted aryl groups, —C(=O)H, —C(=O)-alkyl groups, and —C(=O)-aryl groups; $R_{31}$, $R_{32}$, $R_{33}$, and $R_{34}$ may be the same or different and are independently selected from the group consisting of H, Cl, Br, F, I, —$NO_2$, —CN, —OH, —$OR_{40}$ groups, —$NR_{41}R_{42}$ groups, —C(=O)$R_{43}$ groups, —SH groups, substituted and unsubstituted amidinyl groups, substituted and unsubstituted guanidinyl groups, substituted and unsubstituted alkyl groups, substituted and unsubstituted aryl groups, substituted and unsubstituted alkenyl groups, substituted and unsubstituted alkynyl groups, substituted and unsubstituted heterocyclyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, substituted and unsubstituted aminoalkyl groups, substituted and unsubstituted heterocyclylaminoalkyl groups, substituted and unsubstituted dihetero-cyclylaminoalkyl groups, substituted and unsubstituted (alkyl)(heterocyclyl)aminoalkyl groups, substituted and unsubstituted (aryl)(heterocyclyl)aminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups; $R_{36}$ is selected from the group consisting of substituted and unsubstituted alkyl groups, substituted and unsubstituted aryl groups, substituted and unsubstituted heterocyclyl groups, substituted and unsubstituted heterocyclylalkyl groups, —C(=O)H, —C(=O)-alkyl groups, —C(=O)-aryl groups, —C(=O)O-alkyl groups, —C(=O)O-aryl groups, —C(=O)$NH_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —$NH_2$, —NH(alkyl) groups, —NH(aryl) groups, —N(alkyl)$_2$ groups, —N(alkyl)(aryl) groups, —N(aryl)$_2$ groups, —C(=O)NH(heterocyclyl) groups, —C(=O)N(heterocyclyl)$_2$ groups, —C(=O)N(alkyl)(heterocyclyl) groups, and —C(=O)N(aryl)(heterocyclyl) groups; $R_{37}$ is selected from the group consisting of H, substituted and unsubstituted alkyl groups, substituted and unsubstituted aryl groups, and substituted and unsubstituted heterocyclyl groups; $R_{38}$ is selected from the group consisting of H, substituted and unsubstituted alkyl groups, substituted and unsubstituted aryl groups, substituted and unsubstituted heterocyclyl groups, —OH, alkoxy groups, aryloxy groups, —$NH_2$, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted alkylamino groups, substituted and unsubstituted arylamino groups, substituted and unsubstituted dialkylamino groups, substituted and unsubstituted diarylamino groups, substituted and unsubstituted (alkyl)(aryl) amino groups, —C(=O)H, —C(=O)-alkyl groups, —C(=O)-aryl groups, —C(=O)O-alkyl groups, —C(=O)O-aryl groups, —C(=O)$NH_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted and unsubstituted heterocyclylaminoalkyl groups, substituted and unsubstituted diheterocyclylaminoalkyl groups, substituted and unsubstituted (alkyl)(heterocyclyl)aminoalkyl groups, substituted and unsubstituted (aryl)(heterocyclyl)aminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups; $R_{41}$ is selected from the group consisting of H, substituted and unsubstituted alkyl groups, substituted and unsubstituted aryl groups, and substituted and unsubstituted heterocyclyl groups; $R_{42}$ is selected from the group consisting of H, substituted and unsubstituted alkyl groups, substituted and unsubstituted aryl groups, substituted and unsubstituted heterocyclyl groups, —C(=O)H, —C(=O)-alkyl groups, —C(=O)-aryl groups, —C(=O)$NH_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted and unsubstituted heterocyclylaminoalkyl groups, substituted and unsubstituted diheterocyclylaminoalkyl groups, substituted and unsubstituted (heterocyclyl)(alkyl)aminoalkyl groups, substituted and unsubstituted (heterocyclyl)(aryl)aminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups; and $R_{43}$ is selected from the group consisting of H, —NH2, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted and unsubstituted alkyl groups, substituted and unsubstituted aryl groups, —OH, substituted and unsubstituted alkoxy groups, substituted and unsubstituted heterocyclyl groups, substituted and unsubstituted aryloxy groups, heterocyclyloxy groups, —NHOH, —N(alkyl)OH groups, —N(aryl)OH groups, —N(alkyl)O-alkyl groups, —N(aryl)O-alkyl groups, —N(alkyl)O-aryl groups, and —N(aryl)O-aryl groups, or a pharmaceutically acceptable salt, ester, or prodrug thereof.

In a further embodiment of the invention, the pharmaceutical composition comprises a SMIP compound that is an hydropthalamide compound of formula (IX):

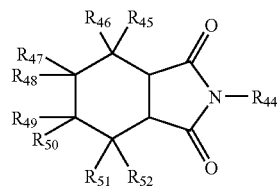

IX

Wherein $R_{44}$ is selected from the group consisting of substituted or unsubstituted aryl, heteroaryl, arylalkyl, heteroarylalkyl, fused arylaryl, unfused arylaryl, fused heteroarylaryl, unfused heteroarylaryl, fused arylheteroaryl, and unfused arylheteroaryl; $R_{45}$, $R_{47}$, $R_{49}$, and $R_{51}$ may be the same or different and are independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl; and $R_{46}$, $R_{48}$, $R_{50}$, and $R_{52}$ may be the same or different and are independently selected from the group consisting of H, halogen, and substituted or unsubstituted alkyl groups, or a pharmaceutically acceptable salt, ester, or prodrug thereof.

In a further embodiment of the invention, the pharmaceutical composition comprises a SMIP compound that is a benzophenone compound of formula (X):

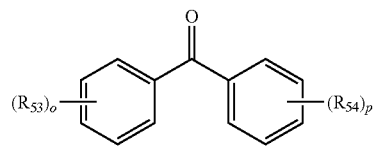

X

Wherein $R_{53}$ is independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl; $R_{54}$ is independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl; and o and p are integers from 0-4, or a pharmaceutically acceptable salt, ester, or prodrug thereof.

In a further embodiment of the invention, the pharmaceutical composition comprises a SMIP compound that is an isoxazole compound of formula (XI):

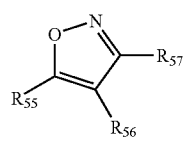

XI

Wherein $R_{55}$ is selected from the group consisting of substituted or unsubstituted aryl, arylalkyl, heteroaryl, heteroarylalkyl, heterocyclyl, and heterocyclylalkyl; $R_{56}$ is selected from the group consisting of substituted or unsubstituted aryl, arylalkyl, heteroaryl, heteroarylalkyl, heterocyclyl, and heterocyclylalkyl; $R_{57}$ is selected from the group consisting of H, halogen, hyroxy, and substituted or unsubstituted alkyl, aryl, heteroaryl, heterocyclyl, and carbonyl, or a pharmaceutically acceptable salt, ester, or prodrug thereof.

In a further embodiment of the invention, the pharmaceutical composition comprises a SMIP compound that is a sterol compound of formula (XII):

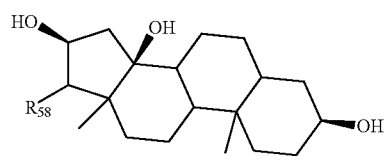

XII

Wherein $R_{58}$ is selected from the group consisting of substituted or unsubstituted aryl, arylalkyl, heteroaryl, heteroarylalkyl, heterocyclyl, and heterocyclylalkyl, or a pharmaceutically acceptable salt, ester, or prodrug thereof.

In a further embodiment of the invention, the pharmaceutical composition comprises a SMIP compound that is a quinazilinone compound of formula (XIII):

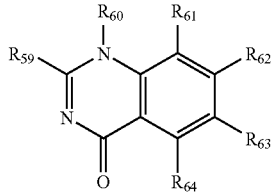

XIII

Wherein $R_{59}$ is selected from the group consisting of H, halogen, hydroxy, and substituted or unsubstituted alkyl, aminoalkyl, alklyaminoalkyl, alkoxy, dialkylaminoalkyl, hydroxyalkyl, alkenyl, alkynyl, carbocyclyl, carbocyclylalkyl, heterocyclyl, and heterocyclylalkyl; $R_{60}$ is selected from the group consisting of substituted or unsubstituted aryl, heteroaryl, arylalkyl, heteroarylalkyl, and heterocyclylalkyl; and, $R_{61}$, $R_{62}$, $R_{63}$, and $R_{64}$ may be the same or different and are independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups, or a pharmaceutically acceptable salt, ester, or prodrug thereof.

In a further embodiment of the invention, the pharmaceutical composition comprises a SMIP compound that is a pyrrole compound of formula (XIV):

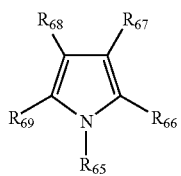

XIV

Wherein $R_{65}$ is selected from the group consisting of H, hydroxy, and substituted or unsubstituted alkyl, aryl, heteroaryl, heteroarylalkyl, arylalkyl, heteroarylaminoalkyl, arylaminoalkyl, heteroaryloxyalkyl, and aryloxyalkyl groups; $R_{66}$, $R_{67}$, $R_{68}$, and $R_{69}$ may be the same or different and are independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups, or a pharmaceutically acceptable salt, ester, or prodrug thereof.

In a further embodiment of the invention, the pharmaceutical composition comprises a SMIP compound that is an anthraquinone compound is a compound of Formula (XVI):

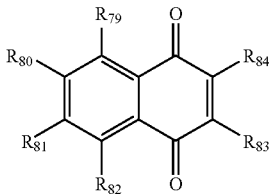

XVI

Wherein $R_{79}$, $R_{80}$, $R_{81}$, and $R_{82}$ may be the same or different and are independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, sulfonyl, aminosulfonyl, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups; and, $R_{83}$ and $R_{84}$ are taken together to form a substituted or unsubstituted 5-6 membered ring containing all carbon atoms or 1-2 heteroatoms selected from the group consisting of O, S, and N, or a pharmaceutically acceptable salt, ester, or prodrug thereof.

In a further embodiment of the invention, the pharmaceutical composition comprises a SMIP compound that is a quinoxaline compound of formula (XVII):

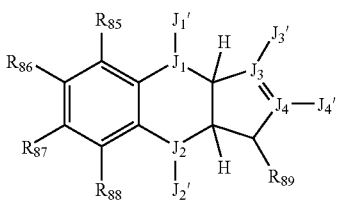

XVII

Wherein $J_1$ is either C or N, $J_{1'}$ is selected from the group consisting of H, substituted aryl, unsubstituted aryl, substituted heteroaryl, and unsubstituted heteroaryl; $J_2$ is either C or N, $J_{2'}$ is selected from the group consisting of H, substituted aryl, unsubstituted aryl, substituted heteroaryl, and unsubstituted heteroaryl; $J_3$ is selected from the group consisting of —CO—, —NH—, and —N=; if $J_4$ is —O— then $J_{4'}$ is absent; or, if $J_4$ is =C— then $J_{4'}$ is selected from the group consisting of H and substituted or unsubstituted alkyl, alkoxy, aryl, heteroaryl, heteroarylalkyl, arylalkyl, aminoalkyl, alkylamino, and alkylthio groups; and, $R_{85}$, $R_{86}$, $R_{87}$, $R_{88}$, and $R_{89}$ may be the same or different and are independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, sulfonyl, aminosulfonyl, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups, or a pharmaceutically acceptable salt, ester, or prodrug thereof.

In a further embodiment of the invention, the pharmaceutical composition comprises a SMIP compound that is a triazine compound, or a pharmaceutically acceptable salt, ester, or prodrug thereof.

In a further embodiment of the invention, the pharmaceutical composition comprises a SMIP compound that is a benzazole compound of formula (XXI):

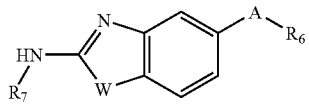

Wherein A is selected from the group consisting of —O—, —S—, —NH—, and —NR$_8$—; W is selected from the group consisting of —CH$_2$—, —O—, —S—, —NH—, and —NR$_8$—; R$_7$ is selected from the group consisting of carbocyclyl, unfused carbocyclylcarbocyclyl, substituted aryl, unsubstituted aryl, substituted heteroaryl, unsubstituted heteroaryl, substituted fused arylheteroaryl, unsubstituted fused arylheteroaryl, substituted unfused arylaryl and unsubstituted unfused arylaryl; R$_6$ is selected from the group consisting of substituted or unsubstituted aryl, and heteroaryl; and, R$_8$ is independently substituted or unsubstituted alkyl, or a pharmaceutically acceptable salt, ester, or prodrug thereof.

In a further embodiment of the invention, the pharmaceutical composition comprises a SMIP compound that is a pyrazalopyrimidine compound of formula (XXII):

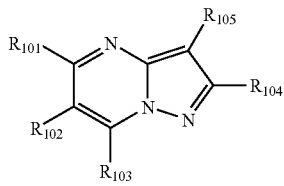

Wherein R$_{101}$ is selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, sulfonyl, aminosulfonyl, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups; R$_{102}$ is selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups; R$_{103}$ is selected from the group consisting of H, nitro, halogen, amino, hydroxy, cyano, carboxcyclic acid, trifluoromethyl, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups; R$_{104}$ is selected from the group consisting of H and substituted or unsubstituted aryl, heteroaryl, arylalkoxy, heteroarylalkoxy, arylalkylamino, arylamino, heteroarylamino, heteroarylaminoalkyl, heterocyclyl, heterocyclylalkoxy, heterocyclylalkyl, carbocyclylalkyl and carbocyclyl groups; R$_{105}$ is selected from the group consisting of H and substituted or unsubstituted aryl, heteroaryl, arylalkoxy, heteroarylalkoxy, arylalkylamino, arylamino, heteroarylamino, heteroarylaminoalkyl, heterocyclyl, heterocyclylalkoxy, heterocyclylalkyl, carbocyclylalkyl and carbocyclyl groups; wherein at least one of R$_{104}$ and R$_{105}$ is not H, or a pharmaceutically acceptable salt, ester, or prodrug thereof.

In a further embodiment of the invention, the pharmaceutical composition comprising any of the above SMIP compounds further comprises an antigen. In a preferred embodiment the pharmaceutical composition is an enhanced immune-response eliciting composition.

In an additional embodiment of the invention, the antigen is associated with a disease selected from the group consisting of BCG, cholera, plague, typhoid, hepatitis B infection, influenza, inactivated polio, rabies, measles, mumps, rubella, oral polio, yellow fever, tetanus, diphtheria, hemophilus influenzae b, meningococcus infection, and pneumococcus infection.

The invention also relates to a method of stimulating an immune response in a subject comprising administering a pharmaceutical composition comprising a SMIP compound. The immune response may be defined as the cellular production of one or more cytokines.

The invention also relates to a method of treating asthma comprising administering to a patient in need thereof, an effective amount of a pharmaceutical composition comprising one or more of the SMIP compounds described herein.

The invention also relates to a method of vaccinating a subject comprising administering an effective amount of a pharmaceutical composition comprising one or more of the SMIP compounds described herein prior to, at the same time as, or after administration of a vaccine composition comprising an antigen.

The invention also relates to a method of vaccinating a subject comprising administering the pharmaceutical composition comprising one or more of the SMIP compounds described herein and one or more antigens.

The present invention also relates to pharmaceutical compositions comprising one or more SMIP compounds selected from the group consisting of: N-methyl-4-[(2-{[2-(1-methylethyl)phenyl]amino}-1H-benzimidazol-5-yl)oxy]pyridine-2-carboxamide; N-methyl-4-{[1-methyl-2-({3-[(trimethylsilyl)ethynyl]phenyl}-1H-benzimidazol-5-yl]oxy}pyridine-2-carboxamide; N-methyl-4-[(1-methyl-2-{[2-(phenylcarbonyl)phenyl]amino}-1H-benzimidazol-5-yl)oxy]pyridine-2-carboxamide; 4-(methyloxy)-N-[6-(methyloxy)-1,3-benzothiazol-2-yl]-3-nitrobenzamide; 4-({2-[(4-butylphenyl)amino]-1,3-benzothiazol-5-yl}oxy)-N-methylpyridine-2-carboxamide; N-methyl-4-({1-methyl-2-[(6-pyrrolidin-1-ylpyridin-3-yl)amino]-1H-benzimidazol-5-yl}oxy)pyridine-2-carboxamide; 4-({2-[1,1'-bi(cyclohexyl)-2-ylamino]-1-methyl-1H-benzimidazol-5yl}oxy)-N-methylpyridine-2-carboxamide; 4-({2-[(4-chlorophenyl)amino]-1-methyl-1H-benzimidazol-5-yl}oxy)-N-1,3-thiazol-2-ylpyridine-2-carboxamide; 4-[(1-methyl-2-{[2-(methyloxy)phenyl]amino}-1H-benzimidazol-5-yl)oxy]-N-[3-(methyloxy)propyl]pyridine-2-carboxamide; and, 4-({2-[(4-ethylphenyl)amino]-1,3-benzoxazol-5-yl}oxy)-N-methylpyridine-2-carboxamide.

The present invention also relates to pharmaceutical compositions comprising one or more SMIP compounds selected from the group consisting of: 5-chloro-1-{[3-(trifluoromethyl)phenyl]methyl}-1H-indole-2,3-dione; 1-[(4-methylphenyl)methyl]-5-nitro-1H-indole-2,3-dione; 5-chloro-1-{[3-(trifluoromethyl)phenyl]methyl}-1H-indole-2,3-dione; 1-methyl-6,7-bis(methyloxy)-2-{[3-(methyloxy)phenyl]carbonyl}-1,2,3,4-tetrahydroisoquinoline; 1-methyl-6,7-bis (methyloxy)-2-(naphthalen-2-ylcarbonyl)-1,2,3,4-tetrahydroisoquinoline; and, [2-(trifluoromethyl)phenyl]methyl 3-[4-(aminocarbonyl)phenyl]-2-cycloheptyl-1-oxo-1,2,3,4-tetrahydroisoquinoline-4-carboxylate.

The present invention also relates to pharmaceutical compositions comprising one or more SMIP compounds selected from the group consisting of: ethyl 4-{[5-[3,4-bis(methyloxy)phenyl]-7-(trifluoromethyl)pyrazolo[1,5-a]pyrimidin-3-yl]carbonyl}piperazine-1-carboxylate; 5-[3,4-bis(methyloxy)phenyl]-3-(piperidin-1-ylcarbonyl)-7-(trifluoromethyl) pyrazolo[1,5-a]pyrimidine; 5-[3,4-bis(methyloxy)phenyl]-N-methyl-N-(2-pyridin-2-ylethyl)-7-(trifluoromethyl) pyrazolo[1,5-a]pyrimidine-2-carboxamide; 5-propyl-2-thien-2-ylpyrazolo[1,5-a]pyrimidin-7-ol; anthra[1,2-c][1,2,5]thiadiazole-6,11-dione; benzo[b]oxanthrene-6,11-dione; ethyl 6,11-dioxo-6,11-dihydrobenzo[b]phenazine-2 -carboxylate; N,N-dimethyl-9,10-dioxo-9,10-dihydroanthracene-1-sulfonamide; and, 2-(trifluoromethyl)-3-{[3,4,5-tris(methyloxy)phenyl]carbonyl}naphtho[2,3-b]furan-4,9-dione.

The present invention also relates to pharmaceutical compositions comprising one or more SMIP compounds selected from the group consisting of: 2-(2-oxopropyl)-2-phenyl-1H-indene-1,3(2H)-dione; 5,6-dichloro-2-[2-chloro-5-(trifluoromethyl)phenyl]-1H-isoindole-1,3(2H)-dione; ethyl 4-{5-[(3-nitrophenyl)carbonyl]-1,3-dioxo-1,3-dihydro-2H-isoindol-2-yl}benzoate; 5,6-dichloro-2-[2-chloro-5-(trifluoromethyl)phenyl]-1H-isoindole-1,3(2H)-dione; 2-(4-amino-2-oxo-1-propyl-1,2-dihydroquinolin-3-yl)-1H-benzimidazole-6-carbonitrile; 4-amino-6-fluoro-7-({[4-(methyloxy)phenyl]methyl}amino)-3-[5-(4-methylpiperazin-1-yl)-1H-benzimidazol-2-yl]quinolin-2 (1H)-one; 6-chloro-3-(5-chloro-1H-benzimidazol-2-yl)-4-{[2-(dimethylamino)ethyl]amino}quinolin-2(1H)-one; and, 4-amino-5-(1H-benzimidazol-2-yl)-1-methyl-1,7-dihydro-6H-pyrazolo[3,4-b]pyridin-6-one.

The present invention also relates to pharmaceutical compositions comprising one or more SMIP compounds selected from the group consisting of: 3-bromo-4-{[(2-fluorophenyl)methyl]oxy}-5-(methyloxy)benzaldehyde thiosemicarbazone; 2-[4-(3-chlorophenyl)piperazin-1-yl]-5-nitrobenzaldehyde thiosemicarbazone; 4-{[2-(3-chlorophenyl)ethyl]amino}-3-nitrobenzaldehyde thiosemicarbazone; (1E)-6,9-dimethyl-2,3,4,9-tetrahydro-1H-carbazol-1-one thiosemicarbazone; (2E)-1,1'-bi(cyclohexan)-1-en-2-one thiosemicarbazone; 4-{[2-(4-chlorophenyl)ethyl]amino}-3-nitrobenzaldehyde thiosemicarbazone; 4-(diethylamino)-2-{[(4-fluorophenyl)methyl]oxy}benzaldehyde N-(2-piperidin-1-ylethyl)thiosemicarbazone; 3,4-bis(methyloxy) benzaldehyde (1,1-dioxido-1,2-benzisothiazol-3-yl) (methyl)hydrazone; and, (2E)-2-[(4-chlorophenyl)(5-chlorothien-2-yl)methylidene]hydrazine carboximidamide.

The present invention also relates to pharmaceutical compositions comprising one or more SMIP compounds selected from the group consisting of: 5,5-dimethyl-4-methylidene-3-(2,4,6-trinitrophenyl)-1,3-oxazolidin-2-one; 5-methyl-2-[4-(methyloxy)phenyl]hexahydro-1H-isoindole-1,3(2H)-dione; 5-methyl-2-(4-methylphenyl)hexahydro-1H-isoindole-1,3(2H)-dione; N~2~-(4-chlorophenyl)-6,6-dimethyl-1,6-dihydro-1,3,5-triazine-2,4-diamine; (7Z)-7-(furan-2-ylmethylidene)-3-phenyl-3,4-dihydro-2H-[1,3]thiazolo[3,2-a][1,3,5]triazin-6(7H)-one; (3aR)-6,7-dihydroxy-9-[3,4,5-tris(methyloxy)phenyl]-3a,4,9,9a-etrahydronaphtho[2,3-c]furan-1(3H)-one; 6-chloro-2-(ethyloxy)-4-methyl-3-(4-nitrophenyl)-3a,4,9,9a-tetrahydro-3H-pyrrolo[2,3-b]quinoxaline; ethyl 2-(ethyloxy)-4-methyl-3a,4,9,9a-tetrahydro-3H-pyrrolo[2,3-b]quinoxaline-3-carboxylate;

ethyl 4-({[2,5-bis(methyloxy)phenyl]amino}methyl)-3,5-dimethyl-1H-pyrrole-2-carboxylate; 1-{3-[(6-amino-5-nitropyridin-2-yl)amino]propyl}-4-(2-chlorophenyl)-N-[(2S)-2-hydroxypropyl]-1H-pyrrole-3-carboxamide; (4-methylphenyl)(5-nitro-2-piperidin-1-ylphenyl)methanone; (2S,5R)-N~1~-(4-methylphenyl)-5-phenyl-N~2~-(2-pyridin-2-ylethyl)pyrrolidine-1,2-dicarboxamide; 2-[(3S)-3-(acetylamino)-2-oxopyrrolidin-1-yl]-N-[2-(4-fluorophenyl)ethyl]acetamide; N-[2-(2,4-dichlorophenyl)ethyl]-4-({(Z)-[(4,4-difluorocyclohexyl)imino][(3S)-3-methylpiperazin-1-yl]methyl}amino)benzamide; 4-[4-(methyloxy)phenyl]-5-phenylisoxazole; methyl 4-{[4-(1-methylethyl)-2,3-dioxo-7-(trifluoromethyl)-3,4-dihydroquinoxalin-1(2H)-yl]methyl}benzoate; (3beta,16beta)-3,14,16-trihydroxybufa-20,22-dienolide; and, 2-(aminomethyl)-1-(2-pyridin-2-ylethyl)quinazolin-4(1H)-one.

As to the timing of administration, it should be emphasized that it is the combination of therapeutic agents that gives rise to its synergistic therapeutic effect no matter whether the first and the second agent are administered together or separately. Therefore, the two agents may be given together in a single dose or in separate doses.

The invention further provides compositions, methods of use, and methods of manufacture as described in the detailed description of the invention.

DETAILED DESCRIPTION OF THE INVENTION

As used above and elsewhere herein the following terms and abbreviations have the meanings defined below:
ATP: Adenosine triphosphate
BCG Mycobacterium bovis bacillus Calmette-Guerin
BSA: Bovine Serum Albumin
FHA Filamentous haemaglutinin
GCMS Gas Chromatography/Mass Spectroscopy
*H. Pylori Helicobacter Pylori*
HAV Hepatitis A Virus
HBV Hepatitis B Virus
HCV Hepatitis C Virus
HIV Human Immunodeficiency Virus
HPLC High Performance Liquid Chromatography
HSV Herpes Simplex Virus
$IC_{50}$ value: The concentration of an inhibitor that causes a 50% reduction in a measured activity.
IFN Interferon
IL Interleukin
IMS Immunomagnetic separation
IPV Inactivated polio virus
LCMS Liquid Chromatography/Mass Spectroscopy
LPS Lipopolysaccharide
Men A Neisseria Meningitidis Type A
Men C Neisseria Meningitidis Type C
Men B Neisseria Meningitidis Type B
Men W Neisseria Meningitidis Type W
Men Y Neisseria Meningitidis Type Y
MeOH: Methanol
NANB Non-A, non-B hepatitis
NMR Nuclear magnetic resonance
OMV Outer membrane vesicle
PBMC Peripheral blood mononuclear cells
PT Petussis holotoxin
Rt Room temperature (25° C.)
SMIP Small Molecule Immune Potentiator
TLC Thin-layer chromatography
TNF-a Tumour necrosis factor-a The methods of the invention are useful in treating "allergic diseases," that is accomplished in the same way as other immunotherapeutic methods described herein.

An "allergen" refers to a substance (antigen) that can induce an allergic or asthmatic response in a susceptible subject. The list of allergens is enormous and can include pollens, insect venoms, animal dander, dust, fungal spores, and drugs (e.g. penicillin).

"Asthma" refers to a disorder of the respiratory system characterized by inflammation, narrowing of the airways and increased reactivity of the airways to inhaled agents. Asthma is frequently, although not exclusively associated with atopic or allergic symptoms.

The term "leukotriene inhibitor" includes any agent or compound that inhibits, restrains, retards or otherwise interacts with the action or activity of leukotrienes, such as, but not limited to, 5-lipoxygenase ("5-LO") inhibitors, 5-lipoxygenase activating protein ("FLAP") antagonists, and leukotriene D4 ("LTD4") antagonists.

"Immune-stimulation" or "immune potentiation" refers to activation of the immune system, including humoral or cellular activation, for example, activation of a cell, such as a killer (T or NK) or dendritic cell of the immune system, for example, causing the increase in cytokine production from a dendritic cell leading to an overall enhancement of host defense (immune response).

An "immunogenic composition" refers to a composition capable of modulating the production of cytokines in a subject thereby effecting immune potentiation in the subject.

An "immune-stimulatory effective amount" is an amount effective for activation of the immune system, for example, causing the increase in cytokine production from a dendritic cell leading to an overall enhancement of host defense (immune response).

"Enhancing the immune response to an antigen" by a compound refers to enhancement of the immune response in comparison to that in the absence of the compound. An enhanced immune-response eliciting composition is a composition generally comprising an antigen and a small molecule immune potentiator compound that elicits an immune response greater that a composition comprising an antigen and not containing one or more small molecule immune potentiator compounds. In this embodiment, the compound acts as an adjuvant, for example for use in vaccine compositions and methods.

The term "effective amount" is an amount necessary or sufficient to realize a desired biological effect. For example, an effective amount of a compound to treat an infectious disorder may be an amount necessary to cause an antigen specific immune response upon exposure to an infectious agent. The effective amount may vary, depending, for example, upon the condition treated, weight of the subject and severity of the disease. One of skill in the art can readily determine the effective amount empirically without undue experimentation.

As used herein "an effective amount for treatment" refers to an amount sufficient to palliate, ameliorate, stabilize, reverse, slow or delay progression of a condition such as a disease state.

A "subject" or "patient" is meant to describe a human or vertebrate animal including a dog, cat, pocket pet, marmoset, horse, cow, pig, sheep, goat, elephant, giraffe, chicken, lion, monkey, owl, rat, squirrel, slender loris, and mouse.

A "pocket pet" refers to a group of vertebrate animals capable of fitting into a coat pocket such as, for example, hamsters, chinchillas, ferrets, rats, guinea pigs, gerbils, rabbits and sugar gliders.

As used herein, the term "pharmaceutically acceptable ester" refers to esters, that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrugs" refers to those prodrugs of the compounds of the present invention that are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated by reference. Prodrugs as described in U.S. Pat. No. 6,284,772 for example may be used.

The term "loweralkyl" refers to branched or straight chain acyclical alkyl groups comprising one to ten carbon atoms, including, e.g., methyl, ethyl, propyl, isopropyl, n-butyl, t-butyl, neopentyl and the like.

The phrase "alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following that are provided by way of example: —$CH(CH_3)_2$, —$CH(CH_3)(CH_2CH_3)$, —$CH(CH_2CH_3)_2$, —$C(CH_3)_3$, —$C(CH_2CH_3)_3$, —$CH_2CH(CH_3)_2$, —$CH_2CH(CH_3)$ ($CH_2CH_3$), —$CH_2CH(CH_2CH_3)_2$, —$CH_2C(CH_3)_3$, —$CH_2C$ ($CH_2CH_3)_3$, —$CH(CH_3)CH(CH_3)(CH_2CH_3)$, —$CH_2CH_2CH(CH_3)_2$, —$CH_2CH_2CH(CH_3)(CH_2CH_3)$, —$CH_2CH_2CH(CH_2CH_3)_2$, —$CH_2CH_2C(CH_3)_3$, —$CH_2CH_2C(CH_2CH_3)_3$, —$CH(CH_3)CH_2CH(CH_3)_2$, —$CH(CH_3)CH(CH_3)CH(CH_3)_2$, —$CH(CH_2CH_3)CH(CH_3)CH$ ($CH_3)(CH_2CH_3)$, and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above. Thus, the phrase unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound. Preferred unsubstituted alkyl groups include straight and branched chain alkyl groups and cyclic alkyl groups having 1 to 20 carbon atoms. More preferred such unsubstituted alkyl groups have from 1 to 10 carbon atoms while even more preferred such groups have from 1 to 5 carbon atoms. Most preferred unsubstituted alkyl groups include straight and branched chain alkyl groups having from 1 to 3 carbon atoms and include methyl, ethyl, propyl, and —$CH(CH_3)_2$.

The phrase "substituted alkyl" refers to an unsubstituted alkyl group as defined above in which one or more bonds to a carbon(s) or hydrogen(s) are replaced by a bond to non-hydrogen and non-carbon atoms such as, but not limited to, a halogen atom in halides such as F, Cl, Br, and I; a phosphorus atom in groups such as phosphate and dialkyl alkylphosphonate; oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. Preferred substituted alkyl groups include, among others, alkyl groups in which one or more bonds to a carbon or hydrogen atom is/are replaced by one or more bonds to fluorine atoms. One example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl) (heterocyclyl)amine, (aryl)(heterocyclyl)amine, or diheterocyclylamine group.

The term "alkoxy" refers to RO— wherein R, for example, is alkyl such as loweralkyl defined above. Representative examples of loweralkyl alkoxy groups include methoxy, ethoxy, t-butoxy and the like.

The term "substituted alkoxy" refers to RO—, where R is, for example, an alkyl substituted, for example, with a halogen. RO is for example $OCF_3$.

The term "alkenyl" refers to a branched or straight chain groups comprising two to twenty carbon atoms which also comprises one or more carbon-carbon double bonds. Representative alkenyl groups include prenyl, 2-propenyl (i.e., allyl), 3-methyl-2-butenyl, 3,7-dimethyl-2,6-octadienyl, 4,8-dimethyl-3,7-nonadienyl, 3,7,11-trimethyl-2,6,10-dodecatrienyl and the like.

The term "substituted alkenyl" refers to alkenyl groups that are substituted, for example, diethyl hex-5-enylphosponate, and others with an alkyl or substituted alkyl group such as dialkyl phosphate or an ester such as an acetate ester.

The term "dialkyl amino" refers to an amino group substituted with two alkyl groups such as C1-20 alkyl groups.

The term "substituted dialkyl amino" refers to a dialkylamino substituted, for example, with a carboxylic acid, ester, hydroxy or alkoxy.

The term "hydroxyalkylthio" refers to a thio radical to which is appended a hydroxyalkyl group, where the alkyl is for example lower alkyl. An example is hydroxyethylthio, —$SCH_2CH_2OH$.

The term "N-alkylsulfonamide" refers to the group —$SO_2NH$alkyl, where alkyl is, for example, octyl.

The term "alkynyl" refers to a branched or straight chain comprising two to twenty carbon atoms which also comprises one or more carbon-carbon triple bonds. Representative alkynyl groups include ethynyl, 2-propynyl (propargyl), 1-propynyl and the like.

The phrase "aryl" refers to aryl groups that do not contain heteroatoms. Thus the phrase includes, but is not limited to, groups such as phenyl, biphenyl, anthracenyl, naphthenyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. A preferred unsubstituted aryl group is phenyl. Unsubstituted aryl groups may be bonded to one or more carbon atom(s), oxygen atom(s), nitrogen atom(s), and/or sulfur atom(s) in the parent compound, however.

The phrase "substituted aryl group" has the same meaning with respect to aryl groups that substituted alkyl groups had with respect to alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, and hydroxyphenyl among others.

The term "arylalkyl" refers to a loweralkyl radical to which is appended an aryl group. Representative arylalkyl groups include benzyl, phenylethyl, hydroxybenzyl, fluorobenzyl, fluorophenylethyl and the like.

The term "unfused arylaryl" refers to a group or substituent to which two aryl groups, which are not condensed to each other, are bound. Exemplary unfused arylaryl compounds include, for example, phenylbenzene, diphenyldiazene, 4-methylthio-1-phenylbenzene, phenoxybenzene, (2-phenylethynyl)benzene, diphenyl ketone, (4-phenylbuta-1,3-diynyl)benzene, phenylbenzylamine, (phenylmethoxy)benzene, and the like. Preferred substituted unfused arylaryl groups include: 2-(phenylamino)-N-[4-(2-phenylethynyl)phenyl]acetamide, 1,4-diphenylbenzene, N-[4-(2-phenylethynyl)phenyl]-2-[benzylamino]acetamide, 2-amino-N-[4-(2-phenylethynyl)phenyl]propanamide, 2-amino-N-[4-(2-phenylethynyl)phenyl]acetamide, 2-(cyclopropylamino)-N-[4-(2-phenylethynyl)phenyl]acetamide, 2-(ethylamino)-N-[4-(2-phenylethynyl)phenyl]acetamide, 2-[(2-methylpropyl)amino]-N-[4-(2-phenylethynyl)phenyl]acetamide, 5-phenyl-2H-benzo[d]1,3-dioxolene, 2-chloro-1-methoxy-4-phenylbenzene, 2-[(imidazolylmethyl)amino]-N-[4-(2-phenylethynyl)phenyl]acetamide, 4-phenyl-1-phenoxybenzene, N-(2-aminoethyl)[4-(2-phenylethynyl)phenyl]carboxamide, 2-{[(4-fluorophenyl)methyl]amino}-N-[4-(2-phenylethynyl)phenyl]acetamide, 2-{[(4-methylphenyl)methyl]amino}-N-[4-(2-phenylethynyl) phenyl]acetamide, 4-phenyl-1-(trifluoromethyl)benzene, 1-butyl-4-phenylbenzene, 2-(cyclohexylamino)-N-[4-(2-phenylethynyl)phenyl]acetamide, 2-(ethylmethylamino)-N-[4-(2-phenylethynyl)phenyl]acetamide, 2-(butylamino)-N-[4-(2-phenylethynyl)phenyl]acetamide, N-[4-(2-phenylethynyl)phenyl]-2-(4-pyridylamino)acetamide, N-[4-(2-phenylethynyl)phenyl]-2-(quinuclidin-3-ylamino) acetamide, N-[4-(2-phenylethynyl)phenyl]pyrrolidin-2- ylcarboxamide, 2-amino-3-methyl-N-[4-(2-phenylethynyl) phenyl]butanamide, 4-(4-phenylbuta-1,3-diynyl) phenylamine, 2-(dimethylamino)-N-[4-(4-phenylbuta-1,3-diynyl)phenyl]acetamide, 2-(ethylamino)-N-[4-(4-phenylbuta-1,3-diynyl)phenyl]acetamide, 4-ethyl-1-phenylbenzene, 1-[4-(2-phenylethynyl)phenyl]ethan-1-one, N-(1-carbamoyl-2-hydroxypropyl)[4-(4-phenylbuta-1,3-diynyl)phenyl]carboxamide, N-[4-(2-phenylethynyl)phenyl] propanamide, 4-methoxyphenyl phenyl ketone, phenyl-N-benzamide, (tert-butoxy)-N-[(4-phenylphenyl)methyl] carboxamide, 2-(3-phenylphenoxy)ethanehydroxamic acid, 3-phenylphenyl propanoate, 1-(4-ethoxyphenyl)-4-methoxybenzene, and [4-(2-phenylethynyl)phenyl]pyrrole.

The term "unfused heteroarylaryl" refers to a unfused arylaryl group where one of the aryl groups is a heteroaryl group. Exemplary heteroarylaryl groups include, for example, 2-phenylpyridine, phenylpyrrole, 3-(2-phenylethynyl)pyridine, phenylpyrazole, 5-(2-phenylethynyl)-1,3-dihydropyrimidine-2,4-dione, 4-phenyl-1,2,3-thiadiazole, 2-(2-phenylethynyl)pyrazine, 2-phenylthiophene, phenylimidazole, 3-(2-piperazinylphenyl)furan, 3-(2,4-dichlorophenyl)-4-methylpyrrole, and the like. Preferred substituted unfused heteroarylaryl groups include: 5-(2-phenylethynyl)pyrimidine-2-ylamine, 1-methoxy-4-(2-thienyl)benzene, 1-methoxy-3-(2-thienyl)benzene, 5-methyl-2-phenylpyridine, 5-methyl-3-phenylisoxazole, 2-[3-(trifluoromethyl)phenyl]furan, 3-fluoro-5-(2-furyl)-2-methoxy-1-prop-2-enylbenzene, (hydroxyimino)(5-phenyl(2-thienyl))methane, 5-[(4-methylpiperazinyl)methyl]-2-phenylthiophene, 2-(4-ethylphenyl) thiophene, 4-methylthio-1-(2-thienyl)benzene, 2-(3-nitrophenyl)thiophene, (tert-butoxy)-N-[(5-phenyl(3-pyridyl))methyl]carboxamide, hydroxy-N-[(5-phenyl(3-pyridyl))methyl]amide, 2-(phenylmethylthio)pyridine, and benzylimidazole.

The term "unfused heteroarylheteroaryl" refers to an unfused arylaryl group where both of the aryl groups is a heteroaryl group. Exemplary heteroarylheteroaryl groups include, for example, 3-pyridylimidazole, 2-imidazolylpyrazine, and the like. Preferred substituted unfused heteroarylheteroaryl groups include: 2-(4-piperazinyl-3-pyridyl)furan, diethyl(3-pyrazin-2-yl(4-pyridyl))amine, and dimethyl {2-[2-(5-methylpyrazin-2-yl)ethynyl](4-pyridyl)}amine.

The term "fused arylaryl" refers to an aryl group as previously defined which is condensed, and fully conjugated to an aryl group. Representative fused arylaryl groups include biphenyl, 4-(1-naphthyl)phenyl, 4-(2-naphthyl)phenyl and the like.

The term "fused heteroarylaryl" refers to an aryl group as previously defined which is condensed, and fully conjugated with a heteroaryl group. Representative fused heteroarylaryl groups include quinoline, quinazoline and the like.

The term "fused heteroarylheteroaryl" refers to a heteroaryl group as previously defined which is condensed, and fully conjugated with another heteroaryl group. Representative fused heteroarylheteroaryl groups include pyrazalopyrimidine, imidazoquinoline and the like.

The term "aryloxy" refers to RO— wherein R is an aryl group. Representative arylalkoxy group include benzyloxy, phenylethoxy and the like.

The term "arylalkoxy" refers to a lower alkoxy radical to which is appended an aryl group. Representative arylalkoxy group include benzyloxy, phenylethoxy and the like.

The term "aryloxyaryl" refers to an aryl radical to which is appended an aryloxy group. Representative aryloxyaryl groups include 4-phenoxyphenyl, 3-phenoxyphenyl, 4-phenoxy-1-naphthyl, 3-phenoxy-1-naphthyl and the like.

The term "aryloxyarylalkyl" refers to an arylalkyl radical to which is appended an aryloxy group. Representative aryloxyarylalkyl groups include 4-phenoxyphenylmethyl, 3-phenoxyphenylmethyl, 4-phenoxyphenylethyl, 3-phenoxy-phenylethyl and the like.

The term "arylalkoxyaryl" refers to an aryl radical to which is appended an arylalkoxy group. Representative arylalkoxyaryl groups include 4-benzyloxylphenyl, 3-benzyloxyphenyl and the like.

The term "arylalkoxyarylalkyl" refers to an arylalkyl radical to which is appended an arylalkoxy group. Representative arylalkoxyarylalkyl groups include 4-benzyloxylbenzyl, 3-benzyloxybenzyl and the like.

The term "cycloalkyl" refers to an alicyclic group comprising from 3 to 7 carbon atoms including, but not limited to, cyclopropyl, cyclobutyl, cyclopentyl, cyclohexyl and the like.

The term "cycloalkylalkyl" refers to a loweralkyl radical to which is appended a cycloalkyl group. Representative examples of cycloalkylalkyl include cyclopropylmethyl, cyclohexylmethyl, 2-(cyclopropyl)ethyl and the like.

The term "halogen" refers to iodine, bromine, chlorine or fluorine; "halo" refers to iodo, bromo, chloro or fluoro.

The term "haloalkyl" refers to a lower alkyl radical, as defined above, bearing at least one halogen substituent, for example, chloromethyl, fluoroethyl or trifluoromethyl and the like.

The phrase "heterocyclyl" (or heterocyclic, or heterocyclo) refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydroditihiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

The phrase "substituted heterocyclyl" refers to an heterocyclyl group as defined above in which one of the ring members is bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, 1-methyl piperazinyl, and 2-chloropyridyl among others.

"Aminosulfonyl" refers to the group —S(O)$_2$—NH$_2$. "Substituted aminosulfonyl" refers to the group —S(O)$_2$—NRR' where R is loweralkyl and R' is hydrogen or a loweralkyl. The term "aralkylaminosulfonlyaryl" refers to the group -aryl-S(O)$_2$—NH-aralkyl, where the aralkyl is loweraralkyl.

"Carbonyl" refers to the divalent group —C(O)—.

"Carbonyloxy" refers generally to the group —C(O)—O—. Such groups include esters, —C(O)—O—R, where R is loweralkyl, cycloalkyl, aryl, or loweraralkyl. The term "carbonyloxycycloalkyl" refers generally to both an "carbonyloxycarbocycloalkyl" and an "carbonyloxyheterocycloalkyl", i.e., where R is a carbocycloalkyl or heterocycloalkyl, respectively. The term "arylcarbonyloxy" refers to the group —C(O)—O-aryl, where aryl is a mono- or polycyclic, carbocycloaryl or heterocycloaryl. The term "aralkylcarbonyloxy" refers to the group —C(O)—O-aralkyl, where the aralkyl is loweraralkyl.

The term "sulfonyl" refers to the group —SO$_2$—. "Alkylsulfonyl" refers to a substituted sulfonyl of the structure —SO$_2$R — in which R is alkyl. Alkylsulfonyl groups employed in compounds of the present invention are typically loweralkylsulfonyl groups having from 1 to 6 carbon atoms in its backbone structure. Thus, typical alkylsulfonyl groups employed in compounds of the present invention include, for example, methylsulfonyl (i.e., where R is methyl), ethylsulfonyl (i.e., where R is ethyl), propylsulfonyl (i.e., where R is propyl), and the like. The term "arylsulfonyl" refers to the group —SO$_2$-aryl. The term "aralkylsulfonyl" refers to the group —SO$_2$-aralkyl, in which the aralkyl is loweraralkyl. The term "sulfonamido" refers to —SO$_2$NH$_2$.

As used herein, the term "carbonylamino" refers to the divalent group —NH—C(O)— in which the hydrogen atom of the amide nitrogen of the carbonylamino group can be replaced a loweralkyl, aryl, or loweraralkyl group. Such groups include moieties such as carbamate esters (—NH—C(O)—O—R) and amides —NH—C(O)—O—R, where R is a straight or branched chain loweralkyl, cycloalkyl, or aryl or loweraralkyl. The term "loweralkylcarbonylamino" refers to alkylcarbonylamino where R is a loweralkyl having from 1 to about 6 carbon atoms in its backbone structure. The term "arylcarbonylamino" refers to group —NH—C(O)—R where R is an aryl. Similarly, the term "aralkylcarbonylamino" refers to carbonylamino where R is a lower aralkyl.

As used herein, the term "guanidino" or "guanidyl" refers to moieties derived from guanidine, H$_2$N—C(=NH)—NH$_2$. Such moieties include those bonded at the nitrogen atom carrying the formal double bond (the "2"-position of the guanidine, e.g., diaminomethyleneamino, (H$_2$N)$_2$C=NH—) and those bonded at either of the nitrogen atoms carrying a formal single bond (the "1-" and/or "3"-positions of the guandine, e.g., H$_2$N—C(=NH)—NH—). The hydrogen atoms at any of the nitrogens can be replaced with a suitable substituent, such as loweralkyl, aryl, or loweraralkyl.

Representative cycloimido and heterocycloimido groups include, for example, those shown below. These cycloimido and heterocycloimido can be further substituted and may be attached at various positions as will be apparent to those having skill in the organic and medicinal chemistry arts in conjunction with the disclosure herein.

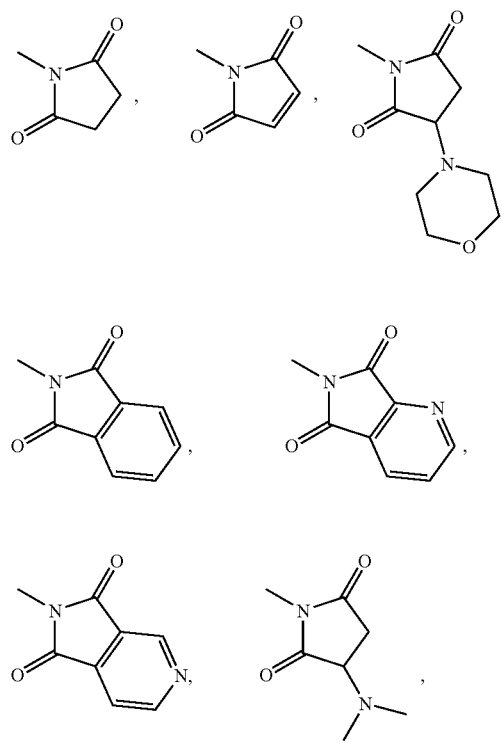

-continued

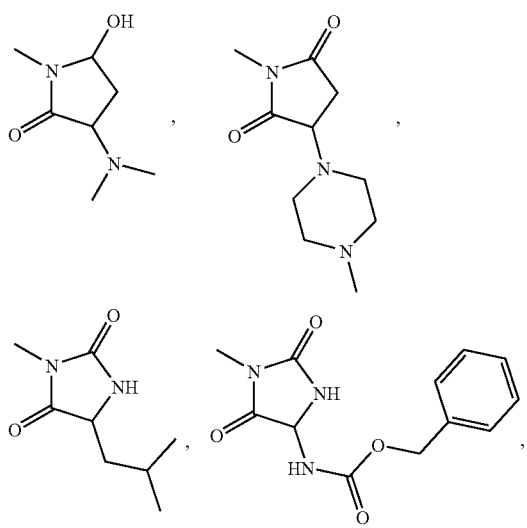

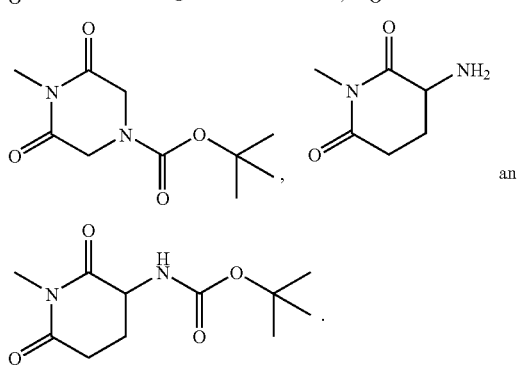

Representative substituted amidino and heterocycloamidino groups include, for example, those shown below. These amidino and heterocycloamidino groups can be further substituted as will be apparent to those having skill in the organic and medicinal chemistry arts in conjunction with the disclosure herein.

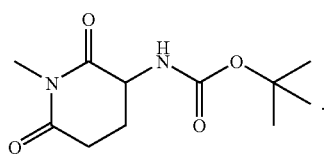

Representative substituted alkylcarbonylamino, alkyloxycarbonylamino, aminoalkyloxycarbonylamino, and arylcarbonylamino groups include, for example, those shown below. These groups can be further substituted as will be apparent to those having skill in the organic and medicinal chemistry arts in conjunction with the disclosure herein.

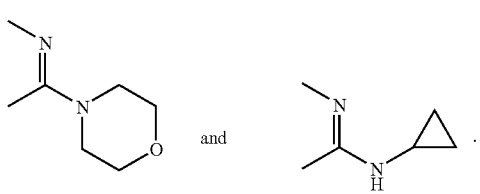

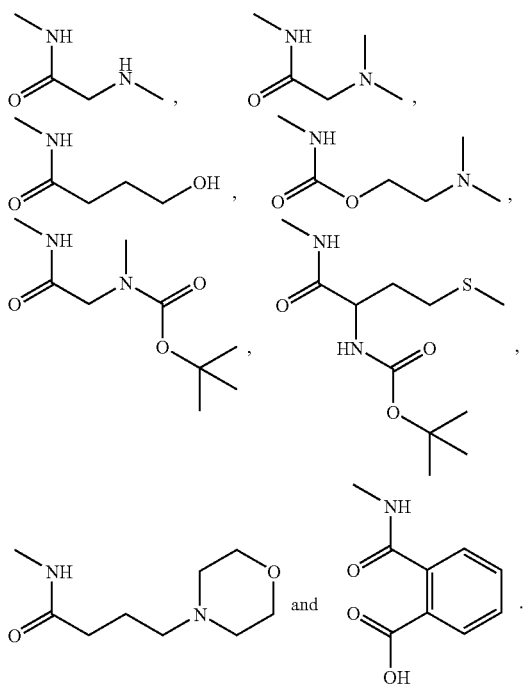

Representative substituted aminocarbonyl groups include, for example, those shown below. These can heterocyclo groups be further substituted as will be apparent to those having skill in the organic and medicinal chemistry arts in conjunction with the disclosure herein.

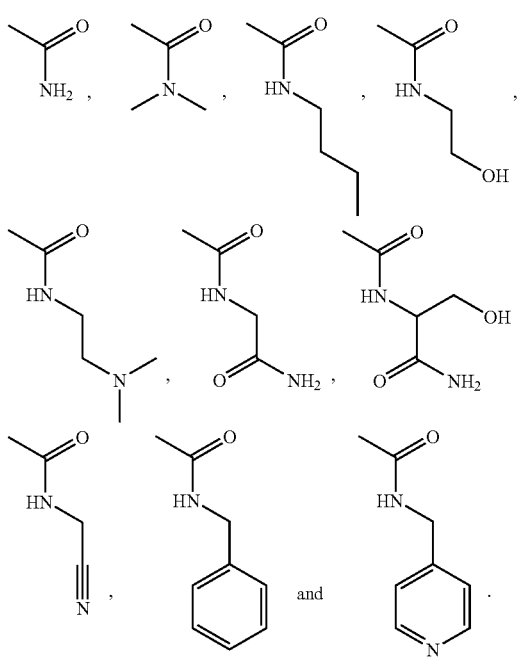

Representative substituted alkoxycarbonyl groups include, for example, those shown below. These alkoxycarbonyl groups can be further substituted as will be apparent to those having skill in the organic and medicinal chemistry arts in conjunction with the disclosure herein.

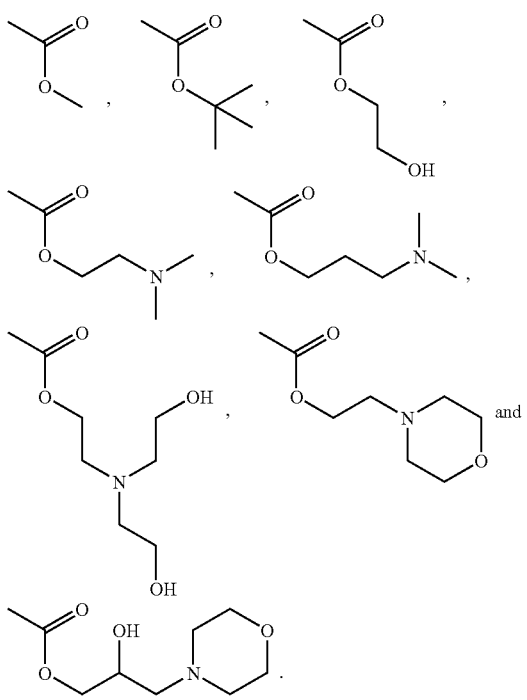

"Substituted" refers to the definite replacement of hydrogen with one or more monovalent or divalent radicals. Suitable substitution groups include, those described herein for particular groups, as well as hydroxyl, nitro, amino, imino, cyano, halo, thio, thioamido, amidino, imidino, oxo, oxamidino, methoxamidino, imidino, guanidino, sulfonamido, carboxyl, formyl, alkyl, substituted alkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, cyanoalkyl, benzyl, pyridyl, pyrazolyl, pyrrole, thiophene, imidazolyl, and the like.

The term "linking moiety" refers to a covalent bond or an uncyclized divalent group, such as, for example, —CO—, —O—, —S—, —CH2—, —NH—, and substituted or unsubstituted alkyl, alkenyl, alkynyl, carbonyl, alkoxycarbonyl groups as defined herein.

The term "SMIP compound" refers to small molecule immuno-potentiating compounds, that include small molecule compounds below about MW 800 g/mol, capable of stimulating or modulating a pro-inflammatory response in a patient. In an embodiment, the SMIP compounds are able to stimulate human peripheral blood mononuclear cells to produce cytokines. Preferred SMIP compounds and derivatives thereof include, for example, aminoazavinyl compounds, benzazole compounds, acylpiperazine compounds, indoledione compounds, tetrahydroisoquinoline (THIQ) compounds, anthraquinone compounds, indanedione compounds, pthalimide compounds, benzocyclodione compounds, aminobenzimidazole quinolinone (ABIQ) compounds, hydraphthalimide compounds, pyrazolopyrimidine compounds, quinazilinone compounds, quinoxaline compounds, triazine compounds, tetrahydropyrrolidinoquinoxaline compounds, pyrrole compounds, benzophenone compounds, sterol compound, and isoxazole compounds.

Acylpiperazine compounds as described throughout this application include compounds of formula (III) as shown below:

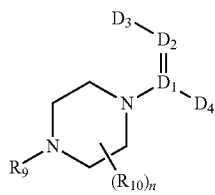

III wherein, $R_9$ is selected from the group consisting of substituted or unsubstituted aryl, heteroaryl, arylalkyl, arylalkenyl, heteroarylalkyl, and heteroarylalkenyl;

$R_{10}$ is substituted or unsubstituted alkyl;

n is an integer from 0-2; and if $D_1$ is carbon than $D_2$ is oxygen, $D_3$ is absent, and $D_4$ is selected from the group consisting of substituted or unsubstituted aryl, heteroaryl, carbocycyl, alkoxyaryl, fused arylaryl, fused arylheteroaryl, and fused heteroarylaryl; or, if $D_1$ is nitrogen than $D_2$ is nitrogen, $D_4$ is absent, and $D_3$ is selected from the group consisting of substituted or unsubstituted aryl, heteroaryl, carbocycyl, alkoxyaryl, fused arylaryl, fused arylheteroaryl, and fused heteroarylaryl.

Indoledione compounds as described throughout this application include compounds of formula (IV) as shown below:

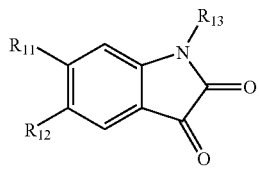

IV wherein, $R_{11}$ and $R_{12}$ are independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups; and, $R_{13}$ is selected from the group consisting of substituted or unsubstituted aryl, heteroaryl, arylalkyl, heteroarylalkyl, heterocyclyl, heterocyclylalkyl, and alkylbenzyl.

Tetrahydroisoquinoline (THIQ) compounds as described throughout this application include compounds of formula (V) as shown below:

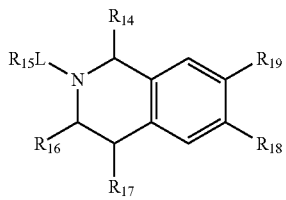

V wherein,
L is a covalent bond or selected from the group consisting of —CH₂—, —Co—, —O—, —S—, CHF, —NH—, —NR₂₀—, where R₂₀ is lower alkyl;
R₁₄ is selected from the group consisting of hydrogen, halogen, and substituted or unsubstituted alkyl;
R₁₅ is selected from the group consisting of substituted or unsubstituted carbocyclyl, aryl, arylalkyl, alkoxyaryl, heteroaryl, heterocyclyl;
R₁₆ is selected from the group consisting of hydrogen, halogen, and substituted or unsubstituted alkyl;
R₁₇ is selected from the group consisting of hydrogen, halogen, and substituted or unsubstituted alkyl; and,
R₁₈ and R₁₉ are independently selected from the group consisting of H, hydroxy, halogen, alkoxy, amino, unsubstituted alkyl, substituted alkyl, and alkylamino.

Benzocyclodione compounds as described throughout this application include compounds of formula (VI) as shown below:

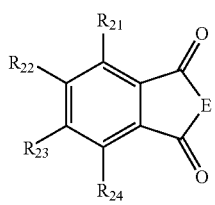

VI wherein,
E is selected from the group consisting of NR₂₅ or CR₂₆R₂₇;
R₂₁, R₂₃, and R₂₄ are independently selected from the group consisting of H, hydroxy, halogen, alkoxy, amino, unsubstituted alkyl, substituted alkyl, and alkylamino;
R₂₂ is selected from the group consisting or H, hydroxy, halogen, alkoxy, amino, and unsubstituted or substituted alkyl, and alkylamino, arylalkyl, heteroarylalkyl, aryl, heteroaryl, arylcarbonyl, heterocyclyl, heterocyclylalkyl, and heteroarylcarbonyl;
R₂₅ is selected from the group consisting of substituted or unsubstituted aryl, heteroaryl, heterocyclyl, carbocyclyl, arylalkyl, heteroarylalkyl, and heterocyclyalkyl;
R₂₆ is selected from the group consisting of H, halogen, hydroxy, amino, and substituted or unsubstituted alkyl, carbonylalkyl, and alkylcarbonylalkyl; and,
R₂₇ is selected from the group aryl, arylalkyl, heteroarylalkyl, heterocyclyl, heterocyclylalkyl, carbocyclyl, arylcarbonylalkyl, and arylalkylcarbonyl.

Aminoazavinyl compounds as described throughout this application include compounds of formula (VII) as shown below:

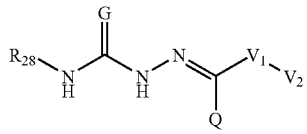

VII wherein,
G is either S or NH;
R₂₈ is selected from the group consisting of H, and substituted or unsubstituted alkyl, aryl, heteroaryl, heteroarylalkyl, arylalkyl, carbocyclyl, carbocyclylalkyl, heterocyclyl, and heterocyclylalkyl;
Q is selected from the group consisting of hydrogen, substituted alkyl, unsubstituted alkyl, and aryl, substituted aryl, heteroaryl, substituted heteroaryl, heterocyclyl, substituted heterocyclyl, fused or unfused arylaryl, substituted arylaryl, arylheteroaryl, substituted arylheteroaryl, heteroarylheteroaryl, and substituted heteroarylheteroaryl;
V₁ is selected from the group consisting of alkyl, substituted alkyl, aryl, substituted aryl, arylalkyl, substituted arylalkyl, heteroaryl, substituted heteroaryl, heteroarylalkyl, substituted heteroarylalkyl, alkoxy, substituted alkoxy, aminocarbonyl, alkoxycarbonyl, carboxyl sulfonyl, methanesulfonyl, and substituted or unsubstituted alkylcarbonyl, arylcarbonyl, aralkylcarbonyl, heteroarylcarbonyl, heteroaralkylcarbonyl, alkylcarbonyloxy, arylcarbonyloxy, aralkylcarbonyloxy, heteroarylcarbonyloxy, heteroaralkylcarbonyloxy, alkylaminocarbonyloxy, arylaminocarbonyloxy, formyl, loweralkylcarbonyl, loweralkoxycarbonyl, aminocarbonyl, aminoaryl, alkylsulfonyl, sulfonamido, aminoalkoxy, alkylamino, heteroarylamino, alkylcarbonylamino, alkylaminocarbonylamino, arylaminocarbonylamino, aralkylcarbonylamino, heteroarylcarbonylamino, arylcarbonylamino, cyclo-amidino, cycloalkyl, cycloimido, arylsulfonyl and arylsulfonamido; and,
V₂ is selected from the group consisting of hydrodgen, halogen, alkyl, substituted alkyl, aryl, substituted aryl, arylalkyl, substituted arylalkyl, heteroaryl, substituted heteroaryl, heteroarylalkyl, substituted heteroarylalkyl, alkoxy, substituted alkoxy, aminocarbonyl, alkoxycarbonyl, carboxyl sulfonyl, methanesulfonyl, and substituted or unsubstituted alkylcarbonyl, arylcarbonyl, aralkylcarbonyl, heteroarylcarbonyl, heteroaralkylcarbonyl, alkylcarbonyloxy, arylcarbonyloxy, aralkylcarbonyloxy, heteroarylcarbonyloxy, heteroaralkylcarbonyloxy, alkylaminocarbonyloxy, arylaminocarbonyloxy, formyl, loweralkylcarbonyl, loweralkoxycarbonyl, aminocarbonyl, aminoaryl, alkylsulfonyl, sulfonamido, aminoalkoxy, alkylamino, heteroarylamino, alkylcarbonylamino, alkylaminocarbonylamino, arylaminocarbonylamino, aralkylcarbonylamino, heteroarylcarbonylamino, arylcarbonylamino, cyclo-amidino, cycloalkyl, cycloimido, arylsulfonyl and arylsulfonamido.

Lactam compounds as described throughout this application include compounds of formula (VIII) as shown below:

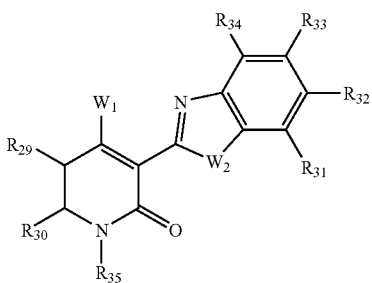

VIII wherein,
- $W_1$ is selected from the group consisting of —OH, —OR$_{36}$ groups, —NR$_{37}$R$_{38}$;
- $W_2$ is selected from the group consisting of O, S, and NR$_{39}$ groups;
- $R_{29}$ and $R_{30}$ join to form a 5 to 6 membered substituted or unsubstituted ring comprising all carbon atoms or at least one O, N, or S atom;
- $R_{35}$ and $R_{39}$ may be the same or different and are selected from the group consisting of H, —OH substituted and unsubstituted alkyl groups, substituted and unsubstituted aryl groups, —C(=O)H, —C(=O)-alkyl groups, and —C(=O)-aryl groups;
- $R_{31}$, $R_{32}$, $R_{33}$, and $R_{34}$ may be the same or different and are independently selected from the group consisting of H, Cl, Br, F, I, —NO$_2$, —CN, —OH, —OR$_{40}$ groups, —NR$_{41}$R$_{42}$ groups, —C(=O)R$_{43}$ groups, —SH groups, substituted and unsubstituted amidinyl groups, substituted and unsubstituted guanidinyl groups, substituted and unsubstituted alkyl groups, substituted and unsubstituted aryl groups, substituted and unsubstituted alkenyl groups, substituted and unsubstituted alkynyl groups, substituted and unsubstituted heterocyclyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, substituted and unsubstituted aminoalkyl groups, substituted and unsubstituted heterocyclylaminoalkyl groups, substituted and unsubstituted diheterocyclylaminoalkyl groups, substituted and unsubstituted (alkyl)(heterocyclyl)aminoalkyl groups, substituted and unsubstituted (aryl)(heterocyclyl)aminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups;
- $R_{36}$ is selected from the group consisting of substituted and unsubstituted alkyl groups, substituted and unsubstituted aryl groups, substituted and unsubstituted heterocyclyl groups, substituted and unsubstituted heterocyclylalkyl groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —NH$_2$, —NH(alkyl) groups, —NH(aryl) groups, —N(alkyl)$_2$ groups, —N(alkyl)(aryl) groups, —N(aryl)$_2$ groups, —C(=O)NH(heterocyclyl) groups, —C(=O)N(heterocyclyl)$_2$ groups, —C(=O)N(alkyl)(heterocyclyl) groups, and —C(=O)N(aryl)(heterocyclyl) groups;
- $R_{37}$ is selected from the group consisting of H, substituted and unsubstituted alkyl groups, substituted and unsubstituted aryl groups, and substituted and unsubstituted heterocyclyl groups;
- $R_{38}$ is selected from the group consisting of H, substituted and unsubstituted alkyl groups, substituted and unsubstituted aryl groups, substituted and unsubstituted heterocyclyl groups, —OH, alkoxy groups, aryloxy groups, —NH$_2$, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted alkylamino groups, substituted and unsubstituted arylamino groups, substituted and unsubstituted dialkylamino groups, substituted and unsubstituted diarylamino groups, substituted and unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)-heterocyclyl groups, —C(=O)—O-heterocyclyl groups, —C(=O)NH(heterocyclyl) groups, —C(=O)-N(heterocyclyl)$_2$ groups, —C(=O)-N(alkyl)(heterocyclyl) groups, —C(=O)—N(aryl)(heterocyclyl) groups, substituted and unsubstituted heterocyclylaminoalkyl groups, substituted and unsubstituted diheterocyclylaminoalkyl groups, substituted and unsubstituted (alkyl)(heterocyclyl)aminoalkyl groups, substituted and unsubstituted (aryl)(heterocyclyl)aminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups;
- $R_{41}$ is selected from the group consisting of H, substituted and unsubstituted alkyl groups, substituted and unsubstituted aryl groups, and substituted and unsubstituted heterocyclyl groups;
- $R_{42}$ is selected from the group consisting of H, substituted and unsubstituted alkyl groups, substituted and unsubstituted aryl groups, substituted and unsubstituted heterocyclyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, —C(=O)-heterocyclyl groups, —C(=O)—O-heterocyclyl groups, —C(=O)NH(heterocyclyl) groups, —C(=O)-N(heterocyclyl)$_2$ groups, —C(=O)—N(alkyl)(heterocyclyl) groups, —C(=O)—N(aryl)(heterocyclyl) groups, substituted and unsubstituted heterocyclylaminoalkyl groups, substituted and unsubstituted diheterocyclylaininoalkyl groups, substituted and unsubstituted (heterocyclyl)(alkyl)aminoalkyl groups, substituted and unsubstituted (heterocyclyl)(aryl)aminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups; and $R_{43}$ is selected from the group consisting of H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted and unsubstituted alkyl groups, substituted and unsubstituted aryl groups, —OH, substituted and unsubstituted alkoxy groups, substituted and unsubstituted heterocyclyl groups, substituted and unsubstituted aryloxy groups, heterocycly-loxy groups, —NHOH, —N(alkyl)OH groups, —N(aryl)OH groups, —N(alkyl)O-alkyl groups, —N(aryl)O-alkyl groups, —N(alkyl)O-aryl groups, and —N(aryl)O-aryl groups.

Preferably $R_{29}$ and $R_{30}$ join together to form a substituted or unsubstituted phenyl ring.

Hydropthalamide compounds as described throughout this application include compounds of formula (IX) as shown below:

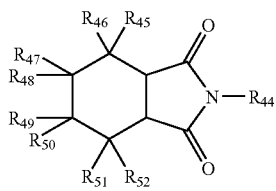

IX wherein, $R_{44}$ is selected from the group consisting of substituted or unsubstituted aryl, heteroaryl, arylalkyl, heteroarylalkyl, fused arylaryl, unfused arylaryl, fused heteroarylaryl, unfused heteroarylaryl, fused arylheteroaryl, and unfused arylheteroaryl;

$R_{45}$, $R_{47}$, $R_{49}$, and $R_{51}$ may be the same or different and are independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl; and $R_{46}$, $R_{48}$, $R_{50}$, and $R_{52}$ may be the same or different and are independently selected from the group consisting of H, halogen, and substituted or unsubstituted alkyl groups.

Benzophenone compounds as described throughout this application include compounds of formula (X) as shown below:

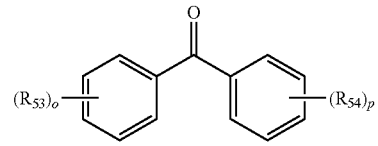

X wherein, $R_{53}$ is independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl;

$R_{54}$ is independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl; and o and p are integers from 0-4.

Isoxazole compounds as described throughout this application include compounds of formula (XI) as shown below:

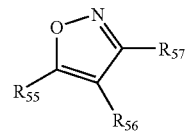

XI wherein, $R_{55}$ is selected from the group consisting of substituted or unsubstituted aryl, arylalkyl, heteroaryl, heteroarylalkyl, heterocyclyl, and heterocyclylalkyl;

$R_{56}$ is selected from the group consisting of substituted or unsubstituted aryl, arylalkyl, heteroaryl, heteroarylalkyl, heterocyclyl, and heterocyclylalkyl; and, $R_{57}$ is selected from the group consisting of H, halogen, hydoxy, and substituted or unsubstituted alkyl, aryl, heteroaryl, heterocyclyl, and carbonyl.

Sterol compounds as described throughout this application include compounds of formula (XII) as shown below:

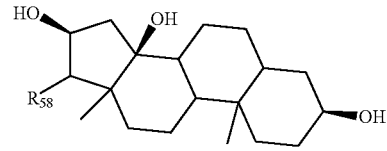

XII wherein,

R$_{58}$ is selected from the group consisting of substituted or unsubstituted aryl, arylalkyl, heteroaryl, heteroarylalkyl, heterocyclyl, and heterocyclylalkyl. Preferably R$_{58}$ is a pyranone substituent.

Quinazilinone compounds as described throughout this application include compounds of formula (XIII) as shown below:

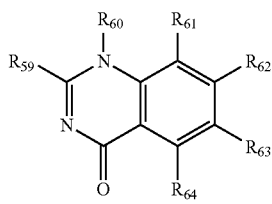

(XIII)

wherein,

R$_{59}$ is selected from the group consisting of H, halogen, hydroxy, and substituted or unsubstituted alkyl, aminoalkyl, alklyaminoalkyl, alkoxy, dialkylaminoalkyl, hydroxyalkyl, alkenyl, alkynyl, carbocyclyl, carbocyclylalkyl, heterocyclyl, and heterocyclylalkyl;

R$_{60}$ is selected from the group consisting of substituted or unsubstituted aryl, heteroaryl, arylalkyl, heteroarylalkyl, and heterocyclylalkyl; and, R$_{61}$, R$_{62}$, R$_{63}$, and R$_{64}$ may be the same or different and are independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups.

Pyrrole compounds as described throughout this application include compounds of formula (XIV) as shown below:

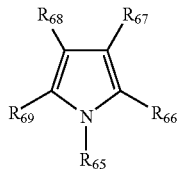

(XIV)

wherein,

R$_{65}$ is selected from the group consisting of H, hydroxy, and substituted or unsubstituted alkyl, aryl, heteroaryl, heteroarylalkyl, arylalkyl, heteroarylaminoalkyl, arylaminoalkyl, heteroaryloxyalkyl, and aryloxyalkyl groups;

R$_{66}$, R$_{67}$, R$_{68}$, and R$_{69}$ may be the same or different and are independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups.

Further preferred pyrrole compounds include those shown in Formula (XV):

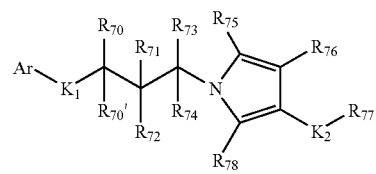

(XV)

wherein:

K$_1$ is nitrogen, oxygen, or optionally substituted carbon;

W is absent or is selected from the group consisting of —O—, —S—, —S(O)—, —SO$_2$—, —NH—, —NH—CO—, —NR'CO—, —NHSO$_2$—, —NR'SO$_2$—, —CO—, —CO$_2$—, —CH$_2$—, —CF$_2$—, CHF, —CONH—, —CONR'—, and —NR'—, where R' is alkyl, substituted alkyl, cycloalkyl, aryl, heteroaryl, heterocyclo;

Ar is optionally substituted aryl, heteroaryl, or a protecting group;

R$_{70}$ and R$_{70}$' are independently selected from the group consisting of hydrogen and methyl;

R$_{71}$, R$_{72}$, R$_{73}$, and R$_{74}$ are independently selected from the group consisting of hydrogen, hydroxyl, and optionally substituted loweralkyl, cycloloweralkyl, cyclicaminoalkyl, alkylaminoalkyl, loweralkoxy, amino, alkylamino, alkylcarbonyl, arylcarbonyl, aralkylcarbonyl, heteroarylcarbonyl, heteroaralkylcarbonyl, aryl and heteroaryl;

R$_{75}$ and R$_{78}$ are independently selected from the group consisting of hydrogen, halo, and optionally substituted loweralkyl, cycloalkyl, alkoxy, amino, aminoalkoxy, carbonyloxy, aminocarbonyloxy, alkylcarbonylamino, arylcarbonylamino, aralkylcarbonylamino, heteroarylcarbonylamino, heteroaralkylcarbonylamino, cycloimido, heterocycloimido, amidino, cycloamidino, heterocycloamidino, guanidinyl, aryl, heteroaryl, heterocycloalkyl, heterocyclocarbonyloxy, heteroarylcarbonyloxy, and arylsulfonamido;

R$_{76}$ is selected from the group consisting of hydrogen, aryl, heteroaryl, substituted heteroaryl, heterocyclyl, and substituted heterocyclyl;

R$_{77}$ is selected from the group consisting of hydrogen, hydroxy, halo, carboxyl, nitro, amino, amido, amidino, imido, cyano, sulfonyl, methanesulonyl, and substituted or unsubstituted alkyl, alkoxy, alkylcarbonyl, arylcarbonyl, aralkylcarbonyl, heteroarylcarbonyl, heteroaralkylcarbonyl, alkylcarbonyloxy, arylcarbonyloxy, aralkylcarbonyloxy, heteroarylcarbonyloxy, heteroaralkylcarbonyloxy, alkylaminocarbonyloxy, arylaminocarbonyloxy, formyl, loweralkylcarbonyl, loweralkoxycarbonyl, aminocarbonyl, aminoaryl, alkylsulfonyl, sulfonamido, aminoalkoxy, alkylamino, heteroarylamino, alkylcarbonylamino, alkylaminocarbonylamino, arylaminocarbonylamino, aralkylcarbonylamino, heteroarylcarbonylamino, arylcarbonylamino, heteroarylcarbonylamino cycloamido, cyclothioamido, cycloamidino, heterocycloamidino, cycloalkyl, cycloimido, heterocycloimido, guanidinyl, aryl, heteroaryl, heterocyclo, heterocycloalkyl, arylsulfonyl and arylsulfonamido;

Anthraquinone compounds of the instant invention include, for example, compounds of Formula (XVI):

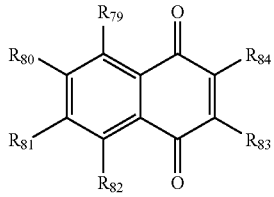

XVI wherein,
R$_{79}$, R$_{80}$, R$_{81}$, and R$_{82}$ may be the same or different and are independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, sulfonyl, aminosulfonyl, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups; and, R$_{83}$ and R$_{84}$ are taken together to form a substituted or unsubstituted 5-6 membered ring containing all carbon atoms or 1-2 heteroatoms selected from the group consisting of O, S, and N.

Quinoxaline compounds referred to throughout this application include tricyclic, partially unconjugated compounds optionally substituted with nitrogen heteroatoms as shown in the preferred quinoxaline embodiment (XVII) below:

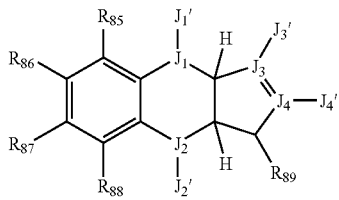

XVII wherein,
J$_1$ is either C or N,
J$_1$' is selected from the group consisting of H, substituted aryl, unsubstituted aryl, substituted heteroaryl, and unsubstituted heteroaryl;
J$_2$ is either C or N,
J$_2$' is selected from the group consisting of H, substituted aryl, unsubstituted aryl, substituted heteroaryl, and unsubstituted heteroaryl;
J$_3$ is selected from the group consisting of —CO—, —NH—, and —N=;
if J$_4$ is —O— then J$_4$' is absent; or,
if J$_4$ is =C— then J$_4$' is selected from the group consisting of H and substituted or unsubstituted alkyl, alkoxy, aryl, heteroaryl, heteroarylalkyl, arylalkyl, aminoalkyl, alkylamino, and alkylthio groups; and,
R$_{85}$, R$_{86}$, R$_{87}$, R$_{88}$, and R$_{89}$ may be the same or different and are independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, sulfonyl, aminosulfonyl, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups.

Triazine compounds refer to substituted 6-membered heterocyclic groups with 3 nitrogen atoms distributed throughout the ring. The preferred embodiments of the instant invention include those shown in structures (XVIII), (XIX) and (XX) shown below:

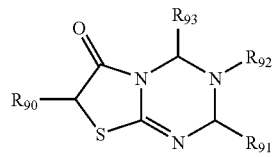

XVIII wherein,
R$_{90}$ is selected from the group consisting of substituted or unsubstituted alkyl, alkenyl, akynyl, aryl, heteroaryl, heteroarylalkyl, heteroarylalkenyl, arylalkyl, and arylalkenyl;
R$_{91}$ and R$_{93}$ are independently selected from the group consisting of H, and unsubstituted alkyl;
R$_{91}$ is aryl; preferably phenyl,

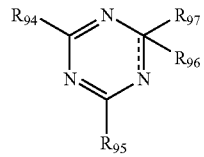

XIX wherein,
R$_{94}$ is selected from the group consisting of H, amino, alkyl, aminoalkyl, and halogen;
R$_{95}$ is selected from the group consisting of substituted or unsubstituted aryl, arylamino, arylalkylamino, heteroaryl, heteroarylamino, and heteroalkylamino;
R$_{96}$ and R$_{97}$ are independently selected from the group consisting of H, halogen, and alkyl, preferably methyl; or,
R$_{96}$ may form a double bond with the nitrogen atom directly below it as indicated by the dashed line in the above structure; and,

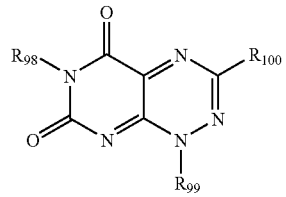

XX wherein,
R$_{98}$ is selected from the group consisting of H, substituted alkyl, and unsubstituted alkyl; preferably methyl,
R$_{99}$ is selected from the group consisting of H, substituted alkyl, and unsubstituted alkyl; preferably ethyl, $R_{100}$ is selected from the group consisting of substituted or unsubstituted aryl, heteroaryl, alkoxyaryl, arylalkyl, and heteroarylalkyl.

Benzazole compounds as described throughout this application include compounds of formula (XXI) as shown below:

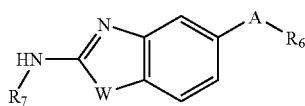

XXI wherein,
A is selected from the group consisting of —O—, —S—, —NH—, and —NR$_8$—;
W is selected from the group consisting of —CH$_2$—, —O—, —S—, —NH—, and —NR$_8$—;
$R_7$ is selected from the group consisting of carbocyclyl, unfused carbocyclylcarbocyclyl, substituted aryl, unsubstituted aryl, substituted heteroaryl, unsubstituted heteroaryl, substituted fused arylheteroaryl, unsubstituted fused arylheteroaryl, substituted unfused arylaryl and unsubstituted unfused arylaryl;
$R_6$ is selected from the group consisting of substituted or unsubstituted aryl, and heteroaryl; and,
$R_8$ is independently substituted or unsubstituted alkyl.

Pyrazalopyrimidine compounds as described throughout this application include compounds of formula (XXII) as shown below:

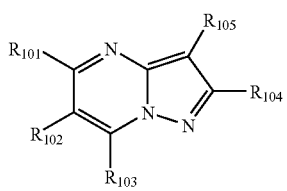

XXII wherein,
$R_{101}$ is selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, sulfonyl, aminosulfonyl, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups;
$R_{102}$ is selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups;
$R_{103}$ is selected from the group consisting of H, nitro, halogen, amino, hydroxy, cyano, carboxcyclic acid, trifluoromethyl, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups;
$R_{104}$ is selected from the group consisting of H and substituted or unsubstituted aryl, heteroaryl, arylalkoxy, heteroarylalkoxy, arylalkylamino, arylamino, heteroarylamino, heteroarylaminoalkyl, heterocyclyl, heterocyclylalkoxy, heterocyclylalkyl, carbocyclylalkyl and carbocyclyl groups;
$R_{105}$ is selected from the group consisting of H and substituted or unsubstituted aryl, heteroaryl, arylalkoxy, heteroarylalkoxy, arylalkylamino, arylamino, heteroarylamino, heteroarylaminoalkyl, heterocyclyl, heterocyclylalkoxy, heterocyclylalkyl, carbocyclylalkyl and carbocyclyl groups;
wherein at least one of $R_{104}$ and $R_{105}$ is not H.

In another embodiment the SMIP compounds have antiviral activity. In another embodiment the SMIP compounds have antimicrobial activity.

SMIP compounds identified by in-vitro (cellular or noncellular assays) or in-vivo methods are thoroughly described in Methods 1 and 2.

The subject invention also includes isotopically-labeled SMIP compounds, that are structurally identical to those disclosed above, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. Compounds of the present invention, prodrugs thereof, and pharmaceutically acceptable salts of said compounds and of said prodrugs that contain the aforementioned isotopes and/or other isotopes of other atoms are within the scope of this invention. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, may afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out known or referenced procedures and by substituting a readily available isotopically labeled reagent for a non-isotopically labeled reagent.

In accordance with the present invention, methods are provided for the administration of an effective amount of a SMIP compound to act as an adjuvant. Also provided are immunogenic compositions comprising a SMIP compound, an antigen, and optionally other adjuvants.

The SMIP compounds may be administered in an immune stimulatory effective amount for the treatment of cancers or infectious diseases either alone or in combination with other therapeutic agents. The SMIP compounds may be administered in an effective amount to modulate cell proliferation in the treatment of cancer, and may act for example through apoptosis or direct stimulation of immune cells to produce cytokines and/or become in other ways activated to destroy or contain malignant cell growth.

The invention provides immunogenic compositions, compounds and pharmaceutical compositions, and methods for modulating cellular proliferation in the treatment of cancer, by administering SMIP'S.

As adjuvants, the SMIP compounds are combined with numerous antigens and delivery systems to form a final immunogenic composition or vaccine product.

As immuno-therapeutics, the SMIP compounds are used alone or in combination with other therapies for treatment of chronic viral or bacterial infections such as HIV, HCV, HBV, HSV, and *H. pylori*, as well as medicaments for the reduction of tumor growth.

In one embodiment, the SMIP compound used in the methods and compositions disclosed herein is a compound of Formula (I), or tautomer thereof, or a pharmaceutically acceptable salt, ester, or prodrug thereof:

X—Y—Z    (I)

wherein,
X is selected from the group consisting of substituted or unsubstituted alkyl, aryl, heteroaryl, fused arylaryl, fused heteroarylaryl, fused heteroarylheteroaryl, unfused arylaryl, unfused heteroarylaryl, unfused heteroarylheteroaryl and heterocyclyl groups;
Y is a linking moiety; and,
Z is selected from the group consisting of substituted or unsubstituted aryl, heteroaryl, fused arylaryl, fused heteroarylaryl, and fused arylheteroaryl groups;
wherein, upon administration of compound I to a patient, human peripheral blood mononuclear cells are stimulated to produce cytokines.

Provided is a method of enhancing an immune response in a subject to an antigen, the method comprising administering to said subject an antigen and an effective amount of a SMIP compound, or a salt, ester or prodrug thereof, to enhance the immune response to said antigen. The antigen is associated, for example, with a disease such as BCG, cholera, plague, typhoid, hepatitis B infection, influenza, inactivated polio, rabies, measles, mumps, rubella, oral polio, yellow fever, tetanus, diphtheria, hemophilus influenzae b, meningococcus infection, and pneumococcus infection. The antigen could be any antigen known in the art including any antigen disclosed herein. The immune response is, for example, the cellular production of one or more cytokines.

Also provided is a pharmaceutical composition comprising an antigen and a SMIP compound capable of enhancing an immune response in a host to said antigen. The SMIP compound may be present in a concentration effective to enhance an immune response to an antigen. The composition may further comprise an aqueous carrier. The antigen may be associated with a disease such as BCG, cholera, plague, typhoid, hepatitis B infection, influenza, inactivated polio, rabies, measles, mumps, rubella, oral polio, yellow fever, tetanus, diphtheria, hemophilus influenzae b, meningococcus infection, and pneumococcus infection. The antigen could be any antigen known in the art including any antigen disclosed herein. The immune response is for example the cellular production of one or more cytokines leading to the enhancement of antigen-specific B and T cell responses and immunologic memory.

The SMIP compound used in the methods and compositions disclosed herein is, for example, a compound of Formula (II):

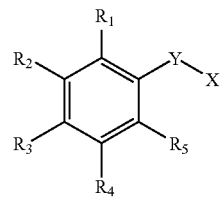

wherein,
Y is a linking moiety;
X is selected from the group consisting of substituted or unsubstituted alkyl, aryl, heteroaryl, fused arylaryl, fused heteroarylaryl, fused heteroarylheteroaryl, unfused arylaryl, unfused heteroarylaryl, unfused heteroarylheteroaryl and heterocyclyl groups;
$R_1$ is selected from the group consisting of H, halogen, hydroxy, amino, nitro, cyano, carboxylic acid, and substituted or unsubstituted alkyl, alkenyl, alkynyl alkylamino, aminoalkyl, alkylcarbonyloxy, alkoxycarbonyl, aminocarbonyl, alkylaminocarbonyl, carbonylamino, alkylcarbonylamino, alkoxy, alkoxyalkyl, carbocyclyl, heterocyclyl, aryl, heteroaryl, fused arylaryl, unfused arylaryl fused heteroarylaryl, unfused heteroarylaryl, fused arylheteroaryl and unfused arylheteroaryl groups;
$R_2$ is selected from the group consisting of H, halogen, hydroxy, amino, nitro, cyano, carboxylic acid, and substituted or unsubstituted alkyl, alkenyl, alkynyl alkylamino, aminoalkyl, alkylcarbonyloxy, alkoxycarbonyl, aminocarbonyl, alkylaminocarbonyl, carbonylamino, alkylcarbonylamino, alkoxy, alkoxyalkyl, carbocyclyl, heterocyclyl, aryl, heteroaryl, fused arylaryl, unfused arylaryl fused heteroarylaryl, unfused heteroarylaryl, fused arylheteroaryl and unfused arylheteroaryl groups; or,
$R_2$ is taken together with $R_3$ to form a fused arylaryl or heteroarylaryl ring system with the benzyl group that they are attached to; or,
$R_3$ is selected from the group consisting of H, halogen, hydroxy, amino, nitro, cyano, carboxylic acid, and substituted or unsubstituted alkyl, alkenyl, alkynyl alkylamino, aminoalkyl, alkylcarbonyloxy, alkoxycarbonyl, aminocarbonyl, alkylaminocarbonyl, carbonylamino, alkylcarbonylamino, alkoxy, alkoxyalkyl, carbocyclyl, heterocyclyl, aryl, heteroaryl, fused arylaryl, unfused arylaryl fused heteroarylaryl, unfused heteroarylaryl, fused arylheteroaryl and unfused arylheteroaryl groups;
$R_4$ is selected from the group consisting of H, halogen, hydroxy, amino, nitro, cyano, carboxylic acid, and substituted or unsubstituted alkyl, alkenyl, alkynyl alkylamino, aminoalkyl, alkylcarbonyloxy, alkoxycarbonyl, aminocarbonyl, alkylaminocarbonyl, carbonylamino, alkylcarbonylamino, alkoxy, alkoxyalkyl, carbocyclyl, heterocyclyl, aryl, heteroaryl, fused arylaryl, unfused arylaryl fused heteroarylaryl, unfused heteroarylaryl, fused arylheteroaryl and unfused arylheteroaryl groups; and
$R_5$ is selected from the group consisting of H, halogen, hydroxy, amino, nitro, cyano, carboxylic acid, and substituted or unsubstituted alkyl, alkenyl, alkynyl alkylamino, aminoalkyl, alkylcarbonyloxy, alkoxycarbonyl, aminocarbonyl, alkylaminocarbonyl, carbonylamino, alkylcarbonylamino, alkoxy, alkoxyalkyl, carbocyclyl, heterocyclyl, aryl, heteroaryl, fused arylaryl, unfused arylaryl fused heteroarylaryl, unfused heteroarylaryl, fused arylheteroaryl and unfused arylheteroaryl groups.

In another aspect of the invention, an acylpiperazine compound of formula (III) is provided as shown below:

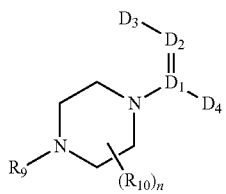

III wherein,
$R_9$ is selected from the group consisting of substituted or unsubstituted aryl, heteroaryl, arylalkyl, arylalkenyl, heteroarylalkyl, and heteroarylalkenyl;

$R_{10}$ is substituted or unsubstituted alkyl;

n is an integer from 0-2; and if $D_1$ is carbon than $D_2$ is oxygen, $D_3$ is absent, and $D_4$ is selected from the group consisting of substituted or unsubstituted aryl, heteroaryl, carbocycyl, alkoxyaryl, fused arylaryl, fused arylheteroaryl, and fused heteroarylaryl; or, if $D_1$ is nitrogen than $D_2$ is nitrogen, $D_4$ is absent, and $D_3$ is selected from the group consisting of substituted or unsubstituted aryl, heteroaryl, carbocycyl, alkoxyaryl, fused arylaryl, fused arylheteroaryl, and fused heteroarylaryl.

In another aspect of the invention, an indoledione compound of formula (IV) is provided as shown below:

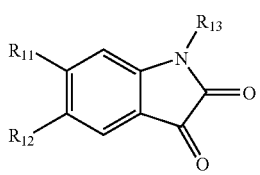

IV wherein,
$R_{11}$ and $R_{12}$ are independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups; and, $R_{13}$ is selected from the group consisting of substituted or unsubstituted aryl, heteroaryl, arylalkyl, heteroarylalkyl, heterocyclyl, heterocyclylalkyl, and alkylbenzyl.

In another aspect of the invention, a tetrahydroisoquinoline (THIQ) compound of formula (V) is provided as shown below:

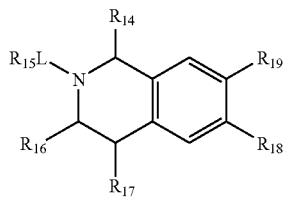

V wherein,
L is a covalent bond or selected from the group consisting of —$CH_2$—, —CO—, —O—, —S—, CHF, —NH—, —$NR_{20}$—, where $R_{20}$ is lower alkyl;

$R_{14}$ is selected from the group consisting of hydrogen, halogen, and substituted or unsubstituted alkyl;

$R_{15}$ is selected from the group consisting of substituted or unsubstituted carbocyclyl, aryl, arylalkyl, alkoxyaryl, heteroaryl, heterocyclyl;

$R_{16}$ is selected from the group consisting of hydrogen, halogen, and substituted or unsubstituted alkyl;

$R_{17}$ is selected from the group consisting of hydrogen, halogen, and substituted or unsubstituted alkyl; and, $R_{18}$ and $R_{19}$ are independently selected from the group consisting of H, hydroxy, halogen, alkoxy, amino, unsubstituted alkyl, substituted alkyl, and alkylamino.

In another aspect of the invention, a benzocyclodione compound of formula (VI) is provided as shown below:

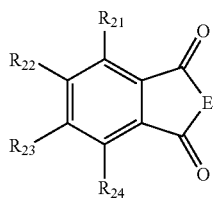

VI wherein,
E is selected from the group consisiting of $NR_{25}$ or $CR_{26}R_{27}$;

$R_{21}$, $R_{23}$, and $R_{24}$ are independently selected from the group consisting of H, hydroxy, halogen, alkoxy, amino, unsubstituted alkyl, substituted alkyl, and alkylamino;

$R_{22}$ is selected from the group consisiting or H, hydroxy, halogen, alkoxy, amino, and unsubstituted or substituted alkyl, and alkylamino, arylalkyl, heteroarylalkyl, aryl, heteroaryl, arylcarbonyl, heterocyclyl, heterocyclylalkyl, and heteroarylcarbonyl;

$R_{25}$ is selected from the group consisting of substituted or unsubstituted aryl, heteroaryl, heterocyclyl, carbocyclyl, arylalkyl, heteroarylalkyl, and heterocyclyalkyl;

$R_{26}$ is selected from the group consisiting of H, halogen, hydroxy, amino, and substituted or unsubstituted alkyl, carbonylalkyl, and alkylcarbonylalkyl; and, $R_{27}$ is selected from the group aryl, arylalkyl, heteroarylalkyl, heterocyclyl, heterocyclylalkyl, carbocyclyl, arylcarbonylalkyl, and arylalkylcarbonyl.

In another aspect of the invention, an aminoazavinyl compound of formula (VII) is provided as shown below:

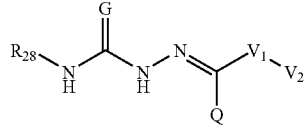

VII wherein,

G is either S or NH;

$R_{28}$ is selected from the group consisting of H, and substituted or unsubstituted alkyl, aryl, heteroaryl, heteroarylalkyl, arylalkyl, carbocyclyl, carbocyclylalkyl, heterocyclyl, and heterocyclylalkyl;

Q is selected from the group consisting of hydrogen, substituted alkyl, unsubstituted alkyl, and aryl, substituted aryl, heteroaryl, substituted heteroaryl, heterocyclyl, substituted heterocyclyl, biaryl, substituted biaryl, arylheteroaryl, substituted arylheteroaryl, heteroarylheteroaryl, and substituted heteroarylheteroaryl;

$V_1$ is selected from the group consisting of alkyl, substituted alkyl, aryl, substituted aryl, arylalkyl, substituted arylalkyl, heteroaryl, substituted heteroaryl, heteroarylalkyl, substituted heteroarylalkyl, alkoxy, substituted alkoxy, aminocarbonyl, alkoxycarbonyl, carboxyl sulfonyl, methanesulfonyl, and substituted or unsubstituted alkylcarbonyl, arylcarbonyl, aralkylcarbonyl, heteroarylcarbonyl, heteroaralkylcarbonyl, alkylcarbonyloxy, arylcarbonyloxy, aralkylcarbonyloxy, heteroarylcarbonyloxy, heteroaralkylcarbonyloxy, alkylaminocarbonyloxy, arylaminocarbonyloxy, formyl, loweralkylcarbonyl, loweralkoxycarbonyl, aminocarbonyl, aminoaryl, alkylsulfonyl, sulfonamido, aminoalkoxy, alkylamino, heteroarylamino, alkylcarbonylamino, alkylaminocarbonylamino, arylaminocarbonylamino, aralkylcarbonylamino, heteroarylcarbonylamino, arylcarbonylamino, cycloamidino, cycloalkyl, cycloimido, arylsulfonyl and arylsulfonamido; and, $V_2$ is selected from the group consisting of hydrodgen, halogen, alkyl, substituted alkyl, aryl, substituted aryl, arylalkyl, substituted arylalkyl, heteroaryl, substituted heteroaryl, heteroarylalkyl, substituted heteroarylalkyl, alkoxy, substituted alkoxy, aminocarbonyl, alkoxycarbonyl, carboxyl sulfonyl, methanesulfonyl, and substituted or unsubstituted alkylcarbonyl, arylcarbonyl, aralkylcarbonyl, heteroarylcarbonyl, heteroaralkylcarbonyl, alkylcarbonyloxy, arylcarbonyloxy, aralkylcarbonyloxy, heteroarylcarbonyloxy, heteroaralkylcarbonyloxy, alkylaminocarbonyloxy, arylaminocarbonyloxy, formyl, loweralkylcarbonyl, loweralkoxycarbonyl, aminocarbonyl, aminoaryl, alkylsulfonyl, sulfonamido, aminoalkoxy, alkylamino, heteroarylamino, alkylcarbonylamino, alkylaminocarbonylamino, arylaminocarbonylamino, aralkylcarbonylamino, heteroarylcarbonylamino, arylcarbonylamino, cycloamidino, cycloalkyl, cycloimido, arylsulfonyl and arylsulfonamido.

In another aspect of the invention, an aminobenzimidazole quinolinone (ABIQ) compound of formula (VIII) is provided as shown below:

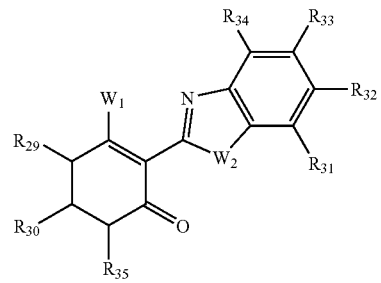

VIII wherein, $W_1$ is selected from the group consisting of —OH, —$OR_{36}$ groups, —$NR_{37}R_{38}$;

W2 is selected from the group consisting of O, S, and $NR_{39}$ groups;

$R_{29}$ and $R_{30}$ join to form a 5 to 6 membered substituted or unsubstituted ring comprising all carbon atoms or at least one O, N, or S atom;

$R_{35}$ and $R_{39}$ may be the same or different and are selected from the group consisting of H, —OH substituted and unsubstituted alkyl groups, substituted and unsubstituted aryl groups, —C(=O)H, —C(=O)-alkyl groups, and —C(=O)-aryl groups;

$R_{31}$, $R_{32}$, $R_{33}$, and $R_{34}$ may be the same or different and are independently selected from the group consisting of H, Cl, Br, F, I, —$NO_2$, —CN, —OH, —$OR_{40}$ groups, —$NR_{41}R_{42}$ groups, —C(=O)$R_{43}$ groups, —SH groups, substituted and unsubstituted amidinyl groups, substituted and unsubstituted guanidinyl groups, substituted and unsubstituted alkyl groups, substituted and unsubstituted aryl groups, substituted and unsubstituted alkenyl groups, substituted and unsubstituted alkynyl groups, substituted and unsubstituted heterocyclyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, substituted and unsubstituted aminoalkyl groups, substituted and unsubstituted heterocyclylaminoalkyl groups, substituted and unsubstituted diheterocyclylaminoalkyl groups, substituted and unsubstituted (alkyl)(heterocyclyl)aminoalkyl groups, substituted and unsubstituted (aryl)(heterocyclyl)aminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups;

$R_{36}$ is selected from the group consisting of substituted and unsubstituted alkyl groups, substituted and unsubstituted aryl groups, substituted and unsubstituted heterocyclyl groups, substituted and unsubstituted heterocyclylalkyl groups, —C(=O)H, —C(=O)-alkyl groups, —C(=O)-aryl groups, —C(=O)O-alkyl groups, —C(=O)O-aryl groups, —C(=O)$NH_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —$NH_2$, —NH(alkyl) groups, —NH(aryl) groups, —N(alkyl)$_2$ groups, —N(alkyl)

(aryl) groups, —N(aryl)$_2$ groups, —C(═O)NH(heterocyclyl) groups, —C(═O)N(heterocyclyl)$_2$ groups, —C(═O)N(alkyl)(heterocyclyl) groups, and —C(═O)N(aryl)(heterocyclyl) groups;

$R_{37}$ is selected from the group consisting of H, substituted and unsubstituted alkyl groups, substituted and unsubstituted aryl groups, and substituted and unsubstituted heterocyclyl groups;

$R_{38}$ is selected from the group consisting of H, substituted and unsubstituted alkyl groups, substituted and unsubstituted aryl groups, substituted and unsubstituted heterocyclyl groups, —OH, alkoxy groups, aryloxy groups, —NH$_2$, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted alkylamino groups, substituted and unsubstituted arylamino groups, substituted and unsubstituted dialkylamino groups, substituted and unsubstituted diarylamino groups, substituted and unsubstituted (alkyl)(aryl)amino groups, —C(═O)H, —C(═O)-alkyl groups, —C(═O)-aryl groups, —C(═O)O-alkyl groups, —C(═O)O-aryl groups, —(═O)NH$_2$, —C(═O)NH(alkyl) groups, —C(═O)NH(aryl) groups, —C(═O)N(alkyl)$_2$ groups, —C(═O)N(aryl)$_2$ groups, —C(═O)N(alkyl)(aryl) groups, —C(═O)-heterocyclyl groups, —C(═O)—O-heterocyclyl groups, —C(═O)NH(heterocyclyl) groups, —C(═O)—N(heterocyclyl)$_2$ groups, —C(═O)—N(alkyl)(heterocyclyl) groups, —C(═O)—N(aryl)(heterocyclyl) groups, substituted and unsubstituted heterocyclylaminoalkyl groups, substituted and unsubstituted diheterocyclylaminoalkyl groups, substituted and unsubstituted (alkyl)(heterocyclyl)aminoalkyl groups, substituted and unsubstituted (aryl)(heterocyclyl)aminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups;

$R_{41}$ is selected from the group consisting of H, substituted and unsubstituted alkyl groups, substituted and unsubstituted aryl groups, and substituted and unsubstituted heterocyclyl groups;

$R_{42}$ is selected from the group consisting of H, substituted and unsubstituted alkyl groups, substituted and unsubstituted aryl groups, substituted and unsubstituted heterocyclyl groups, —C(═O)H, —C(═O)-alkyl groups, —C(═O)-aryl groups, —C(═O)NH$_2$, —C(═O)NH(alkyl) groups, —C(═O)NH(aryl) groups, —C(═O)N(alkyl)$_2$ groups, —C(═O)N(aryl)$_2$ groups, —C(═O)N(alkyl)(aryl) groups, —C(═O)O-alkyl groups, —C(═O)O-aryl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, —C(═O)-heterocyclyl groups, —C(═O)—O-heterocyclyl groups, —C(═O)NH(heterocyclyl) groups, —C(═O)—N(heterocyclyl)$_2$ groups, —C(═O)—N(alkyl)(heterocyclyl) groups, —C(═O)—N(aryl)(heterocyclyl) groups, substituted and unsubstituted heterocyclylaminoalkyl groups, substituted and unsubstituted diheterocyclylaminoalkyl groups, substituted and unsubstituted (heterocyclyl)(alkyl)aminoalkyl groups, substituted and unsubstituted (heterocyclyl)(aryl)aminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups; and $R_{43}$ is selected from the group consisting of H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted and unsubstituted alkyl groups, substituted and unsubstituted aryl groups, —OH, substituted and unsubstituted alkoxy groups, substituted and unsubstituted heterocyclyl groups, substituted and unsubstituted aryloxy groups, heterocyclyloxy groups, —NHOH, —N(alkyl)OH groups, —N(aryl)OH groups, —N(alkyl)O-alkyl groups, —N(aryl)O-alkyl groups, —N(alkyl)O-aryl groups, and —N(aryl)O-aryl groups.

Preferably $R_{29}$ and $R_{30}$ join together to form a substituted or unsubstituted phenyl ring.

In another aspect of the invention, a hydropthalamide compound of formula (IX) is provided as shown below:

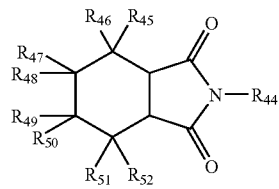

IX wherein, $R_{44}$ is selected from the group consisting of substituted or unsubstituted aryl, heteroaryl, arylalkyl, heteroarylalkyl, fused arylaryl, unfused arylaryl, fused heteroarylaryl, unfused heteroarylaryl, fused arylheteroaryl, and unfused arylheteroaryl;

$R_{45}$, $R_{47}$, $R_{49}$, and $R_{51}$ may be the same or different and are independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl; and $R_{46}$, $R_{48}$, $R_{50}$, and $R_{52}$ may be the same or different and are independently selected from the group consisting of H, halogen, and substituted or unsubstituted alkyl groups.

In another aspect of the invention, a benzophenone compound of formula (X) is provided as shown below:

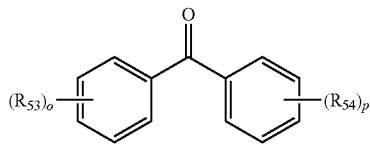

wherein,
R$_{53}$ is independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl;

R$_{54}$ is independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl; and o and p are integers from 0-4.

In another aspect of the invention, an isoxazole compound of formula (XI) is provided as shown below:

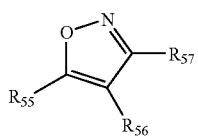

wherein,
R$_{55}$ is selected from the group consisting of substituted or unsubstituted aryl, arylalkyl, heteroaryl, heteroarylalkyl, heterocyclyl, and heterocyclylalkyl;

R$_{56}$ is selected from the group consisting of substituted or unsubstituted aryl, arylalkyl, heteroaryl, heteroarylalkyl, heterocyclyl, and heterocyclylalkyl;

R$_{57}$ is selected from the group consisting of H, halogen, hyroxy, and substituted or unsubstituted alkyl, aryl, heteroaryl, heterocyclyl, and carbonyl.

In another aspect of the invention, a sterol compound of formula (VI) is provided as shown below:

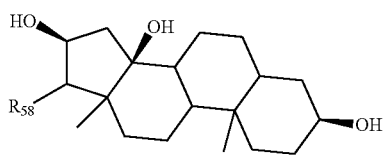

wherein,
R$_{58}$ is selected from the group consisting of substituted or unsubstituted aryl, arylalkyl, heteroaryl, heteroarylalkyl, heterocyclyl, and heterocyclylalkyl. Preferably R$_{58}$ is a pyranone substituent.

In another aspect of the invention, a quinazilinone compound of formula (XIII) is provided as shown below:

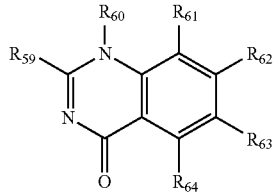

wherein,
R$_{59}$ is selected from the group consisting of H, halogen, hydroxy, and substituted or unsubstituted alkyl, aminoalkyl, alklyaminoalkyl, alkoxy, dialkylaminoalkyl, hydroxyalkyl, alkenyl, alkynyl, carbocyclyl, carbocyclylalkyl, heterocyclyl, and heterocyclylalkyl;

R$_{60}$ is selected from the group consisting of substituted or unsubstituted aryl, heteroaryl, arylalkyl, heteroarylalkyl, and heterocyclylalkyl; and, R$_{61}$, R$_{62}$, R$_{63}$, and R$_{64}$ may be the same or different and are independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups.

In another aspect of the invention, a pyrrole compound of formula (XIV) is provided as shown below:

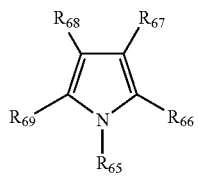

wherein,
R$_{65}$ is selected from the group consisting of H, hydroxy, and substituted or unsubstituted alkyl, aryl, heteroaryl, heteroarylalkyl, arylalkyl, heteroarylaminoalkyl, arylaminoalkyl, heteroaryloxyalkyl, and aryloxyalkyl groups;

R$_{66}$, R$_{67}$, R$_{68}$, and R$_{69}$ may be the same or different and are independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups.

In a more preferred embodiment, pyrrole compounds include those shown in Formula (XV):

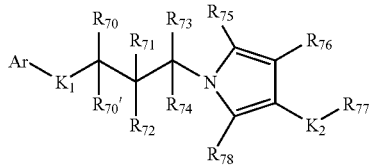

(XV)

wherein:
- $K_1$ is nitrogen, oxygen, or optionally substituted carbon;
- W is absent or is selected from the group consisting of —O—, —S—, —S(O)—, —SO$_2$—, —NH—, —NHCO—, —NR'CO—, —NHSO$_2$—, —NR'SO$_2$—, —CO—, —CO$_2$—, —CH$_2$—, —CF$_2$—, CHF, —CONH—, —CONR'—, and —NR'—, where R' is alkyl, substituted alkyl, cycloalkyl, aryl, heteroaryl, heterocyclyl;
- Ar is optionally substituted aryl, heteroaryl, or a protecting group;
- $R_{70}$ and $R_{70}'$ are independently selected from the group consisting of hydrogen and methyl;
- $R_{71}$, $R_{72}$, $R_{73}$, and $R_{74}$ are independently selected from the group consisting of hydrogen, hydroxyl, and optionally substituted loweralkyl, cycloloweralkyl, cyclicarninoalkyl, alkylaminoalkyl, loweralkoxy, amino, alkylamino, alkylcarbonyl, arylcarbonyl, aralkylcarbonyl, heteroarylcarbonyl, heteroaralkylcarbonyl, aryl and heteroaryl;
- $R_{75}$ and $R_{78}$ are independently selected from the group consisting of hydrogen, halo, and optionally substituted loweralkyl, cycloalkyl, alkoxy, amino, aminoalkoxy, carbonyloxy, aminocarbonyloxy, alkylcarbonylamino, arylcarbonylamino, aralkylcarbonylamino, heteroarylcarbonylamino, heteroaralkylcarbonylamino, cycloimido, heterocycloimido, amidino, cycloamidino, heterocycloamidino, guanidinyl, aryl, heteroaryl, heterocycloalkyl, heterocyclocarbonyloxy, heteroarylcarbonyloxy, and arylsulfonamido;
- $R_{76}$ is selected from the group consisting of hydrogen, aryl, heteroaryl, substituted heteroaryl, heterocyclyl, and substituted heterocyclyl; and,
- $R_{77}$ is selected from the group consisting of hydrogen, hydroxy, halo, carboxyl, nitro, amino, amido, amidino, imido, cyano, sulfonyl, methanesulonyl, and substituted or unsubstituted alkyl, alkoxy, alkylcarbonyl, arylcarbonyl, aralkylcarbonyl, heteroarylcarbonyl, heteroaralkylcarbonyl, alkylcarbonyloxy, arylcarbonyloxy, aralkylcarbonyloxy, heteroarylcarbonyloxy, heteroaralkylcarbonyloxy, alkylaminocarbonyloxy, arylaminocarbonyloxy, formyl, loweralkylcarbonyl, loweralkoxycarbonyl, aminocarbonyl, aminoaryl, alkylsulfonyl, sulfonamido, aminoalkoxy, alkylamino, heteroarylamino, alkylcarbonylamino, alkylaminocarbonylamino, arylaminocarbonylamino, aralkylcarbonylamino, heteroarylcarbonylamino, arylcarbonylamino, heteroarylcarbonylamino cycloamido, cyclothioamido, cycloamidino, heterocycloamidino, cycloalkyl, cycloimido, heterocycloimido, guanidinyl, aryl, heteroaryl, heterocyclo, heterocycloalkyl, arylsulfonyl and arylsulfonamido.

In another aspect of the invention, an anthraquinone compound of formula (XVI) is provided as shown below:

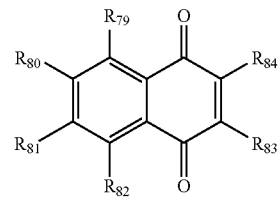

XVI wherein,
- $R_{79}$, $R_{80}$, $R_{81}$, and $R_{82}$ may be the same or different and are independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, sulfonyl, aminosulfonyl, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups; and,
- $R_{83}$ and $R_{84}$ are taken together to form a substituted or unsubstituted 5-6 membered ring containing all carbon atoms or 1-2 heteroatoms selected from the group consisting of O, S, and N.

In another aspect of the invention, a quinoxaline compound of formula (XVII) is provided as shown below:

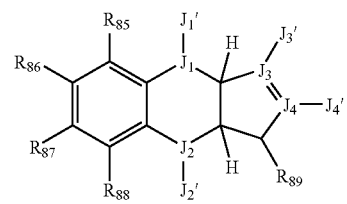

XVII wherein,
- $J_1$ is either C or N,
- $J_1'$ is selected from the group consisting of H, substituted aryl, unsubstituted aryl, substituted heteroaryl, and unsubstituted heteroaryl;
- $J_2$ is either C or N,
- $J_2'$ is selected from the group consisting of H, substituted aryl, unsubstituted aryl, substituted heteroaryl, and unsubstituted heteroaryl;
- $J_3$ is selected from the group consisting of —CO—, —NH—, and —N=;
- if $J_4$ is —O— then $J_4'$ is absent; or,
- if $J_4$ is =C— then $J_4'$ is selected from the group consisting of H and substituted or unsubstituted alkyl, alkoxy, aryl, heteroaryl, heteroarylalkyl, arylalkyl, aminoalkyl, alkylamino, and alkylthio groups; and,
- $R_{85}$, $R_{86}$, $R_{87}$, $R_{88}$, and $R_{89}$ may be the same or different and are independently selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, sulfonyl, aminosulfonyl, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups.

In another aspect of the invention, a triazine compound of formula (XVIII) is provided as shown below:

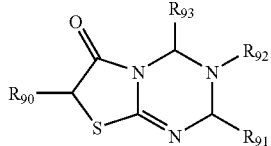

XVIII wherein,
R$_{90}$ is selected from the group consisiting of substituted or unsubstituted alkyl, alkenyl, akynyl, aryl, heteroaryl, heteroarylalkyl, heteroarylalkenyl, arylalkyl, and arylalkenyl;
R$_{91}$ and R$_{93}$ are independently selected from the group consisiting of H, and unsubstituted alkyl;
R$_{91}$ is aryl; preferably phenyl.

In another embodiment of the invention, triazine compounds of formula (XIX) are provided:

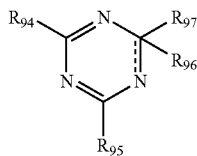

XIX wherein,
R$_{94}$ is selected from the group consisting of H; amino, alkyl, aminoalkyl, and halogen;
R$_{95}$ is selected from the group consisting of substituted or unsubstituted aryl, arylamino, arylalkylamino, heteroaryl, heteroarylamino, and heteroalkylamino;
R$_{96}$ and R$_{97}$ are independently selected from the group consisting of H, halogen, and alkyl, preferably methyl; or,
R$_{96}$ may form a double bond with the nitrogen atom directly below it as indicated by a dashed line.

In still another embodiment of the invention, triazine compounds of formula (XX) are provided:

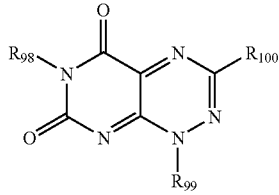

XX wherein,
R$_{98}$ is selected from the group consisting of H, substituted alkyl, and unsubstituted alkyl; preferably methyl,
R$_{99}$ is selected from the group consisting of H, substituted alkyl, and unsubstituted alkyl; preferably ethyl, and,
R$_{100}$ is selected from the group consisting of substituted or unsubstituted aryl, heteroaryl, alkoxyaryl, arylalkyl, and heteroarylalkyl.

In another aspect of the invention, a benzazole compound of formula (XXI) is provided as shown below:

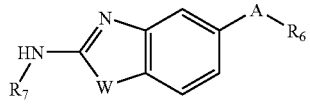

XXI wherein,
A is selected from the group consisting of —O—, —S—, —NH—, and —NR$_8$—;
W is selected from the group consisting of —CH$_2$—, —O—, —S—, —NH—, and —NR$_8$—;
R$_7$ is selected from the group consisting of carbocyclyl, unfused carbocyclylcarbocyclyl, substituted aryl, unsubstituted aryl, substituted heteroaryl, unsubstituted heteroaryl, substituted fused arylheteroaryl, unsubstituted fused arylheteroaryl, substituted unfused arylaryl and unsubstituted unfused arylaryl;
R$_6$ is selected from the group consisting of substituted or unsubstituted aryl, and heteroaryl; and,
R$_8$ is independently substituted or unsubstituted alkyl.

In another embodiment of the invention, pryazalopryimidine compounds of formula (XXII) are provided:

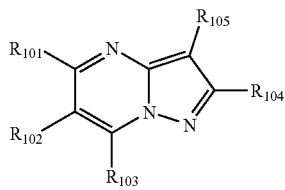

XXII wherein,
R$_{101}$ is selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, sulfonyl, aminosulfonyl, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocycylalkyl, and carbocyclyl groups;
R$_{102}$ is selected from the group consisting of H, nitro, halogen, amino, hydroxy, cyano, carboxcyclic acid, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups;
R$_{103}$ is selected from the group consisting of H, nitro, halogen, amino, hydroxy, cyano, carboxcyclic acid, trifluoromethyl, and substituted or unsubstituted alkyl, aryl, heteroaryl, alkoxy, alkylcarbonyl, alkylcarbonylamino, alkylaminocarbonyl, aminocarbonyl, arylalkoxy, heteroarylalkoxy, alkylamino, arylalkylamino, arylamino, heteroarylamino, heteroarylaminoalkyl, heterocyclyl, heterocyclylalkoxy, heterocyclylalkyl, and carbocyclyl groups;

$R_{104}$ is selected from the group consisting of H and substituted or unsubstituted aryl, heteroaryl, arylalkoxy, heteroarylalkoxy, arylalkylamino, arylamino, heteroarylamino, heteroarylaminoalkyl, heterocyclyl, heterocyclylalkoxy, heterocyclylalkyl, carbocyclylalkyl and carbocyclyl groups;

$R_{105}$ is selected from the group consisting of H and substituted or unsubstituted aryl, heteroaryl, arylalkoxy, heteroarylalkoxy, arylalkylamino, arylamino, heteroarylamino, heteroarylaminoalkyl, heterocyclyl, heterocyclylalkoxy, heterocyclylalkyl, carbocyclylalkyl and carbocyclyl groups;

wherein at least one of $R_{104}$ and $R_{105}$ is not H.

It should be understood that the organic compounds described herein may exhibit the phenomenon of tautomerism. It should be understood that the invention encompasses any tautomeric form of the drawn structure. The compounds comprise asymmetrically substituted carbon atoms. Such asymmetrically substituted carbon atoms can result in the compounds comprising mixtures of stereoisomers at a particular asymmetrically substituted carbon atom or a single stereoisomer. As a result, racemic mixtures, mixtures of diastereomers, as well as single diastereomers of the compounds are included in the present invention. The terms "S" and "R" configuration, are as defined by the *IUPAC 1974 Recommendations for Section E, Fundamental Stereochemistry, Pure Appl. Chem.* (1976) 45, 13-30. The terms α and β are employed for ring positions of cyclic compounds. The α-side of the reference plane is that side on which the preferred substituent lies at the lowered numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, are as defined by the *Chemical Abstracts Index Guide-Appendix IV* (1987) paragraph 203.

One embodiment of the invention is directed to a method of inducing an immunostimulatory effect in a patient comprising administering a SMIP compound in an amount effective to stimulate an immune response such as a cell-mediated immune response.

The SMIP compounds can be used with or without an antigen in therapeutic applications, for example to treat cancer or infectious diseases. The SMIP compounds also may be used in combination with other therapeutic agents, such as anti-virals and monoclonal antibodies in different therapeutic applications.

One preferred embodiment of the method of inducing an immunostimulatory effect in a patient is directed to administering an immunogenic composition comprising a vaccine in an amount effective to stimulate an immune response such as a cell-mediated immune response and, as a vaccine adjuvant, a SMIP compound, in an amount effective to potentiate the immune response such as the cell-mediated immune response to the vaccine.

It is contemplated that a vast number of disorders can be treated with the SMIP compounds and compositions of the present invention. Preferred methods of the invention include SMIP compounds as single agents or in combination with (an)other agent(s), to treat diseases including bacterial diseases, mycotic diseases, viral diseases, malignant tumors, hyperlipemias, and ischemic heart diseases; for example, digestive diseases, circulatory organs' diseases, urinary/genital organs' diseases, immune diseases, cranial nerve diseases, eye diseases, skin diseases, and diseases of nose, ear and throat.

Examples of such diseases susceptive to the SMIP compounds and combinations are bacterial diseases such as bacterial corneal ulcer, bacterial conjunctivitis, bacterial food poisoning, septic shock, endotoxin shock, bacterial endocarditis, bacterial meningitis, bacterial pneumonia, bacterial aneurysm, and bacterial cerebral aneurysm; viral diseases such as fungal meningitis, fungal corneal ulcer, fungal skin diseases, candidiasis, and tinea; viral diseases such as viral gastroenterocolitis, viral hepatitis, viral bronchitis, viral colon inflammatory, viral myocarditis, viral meningitis, viral enterocolitis, viral encephalitis, viral pneumonia, and AIDS; massive malignant tumors such as renal cell carcinoma, mycosis fungoides, and chronic granuloma; blood malignant tumors such as colonic cancer, rectal cancer, carcinoma of the colon and rectum, gastric cancer, thyroid carcinoma, cancer of the tongue, bladder carcinoma, cilium carcinoma, hepatoma, prostatic cancer, carcinoma uteri, cancer of pharynx, lung cancer, breast cancer, malignant melanoma, Kaposi's sarcoma, brain tumor, neuroblastoma, ovarian tumor, testicular tumor, pancreatic tumor, renal cancer, hypernephroma, hemangioendothelioma, adult T-cell leukemia (ATL), chronic myelogenous leukemia (CML), and malignant lymphoma; autoimmune-, allergic- and viral-diseases such as active chronic hepatitis, atrophic gastritis, autoimmune hemolytic anemia, Basedow disease, Behcet's syndrome, Crohn's disease, CRST syndrome, cold agglutinin hemolytic anemia, idiopathic ulcerative colitis, Goodpasture's syndrome, hyperthyroidism, chronic thyroiditis, inflammation of pulmonary alveoli, glomerulonephritis, idiopathic thrombocytopenic purpura, juvenile diabetes mellitus, insulin dependent diabetes mellitus, leukopenia, multi sclerosis, myasthenia gravis, paroxysmal cold hemoglobinuria, pernicious anemia, polyarteritis nodosa, polymyositis, primary biliary cirrhosis, rheumatic fever, rheumatoid arthritis, Sjögren's syndrome, sympathetic ophthalmia, progressive systemic sclerosis, Wegener granulomatosis, asthma, atopic dermatitis, bronchial asthma, graft-versus-host disease, allergic rhinitis, pollinosis, and allergy for bee's toxic; hepatic diseases such as alcoholic hepatitis, toxic hepatitis, viral cirrhosis, alcoholic cirrhosis, toxic cirrhosis, biliary cirrhosis, fatty liver, hepatic tumor, and hepatic vascular disorder; gallbladder/biliary tract diseases such as cholangitis, cholecystitis, primary clerosing cholangitis, gallbladder tumor, and cancer of the bile duct; pancreatic diseases such as acute insufficiency, pancreatic tumor, and pancreatic cysts; circulatory organs' diseases such as ischemia, ischemic heart disease, cerebral ischemia, basilar artery migraine, abnormal vascularnet at the brain base, cerebral apoplexy, aneurysm of the brain base, arteriosclerosis, vascular endothelial disorder, noninsulin-dependent diabetes mellitus, occlusion of the mesenteric vessel, and superior mesenteric artery syndrome; nerve diseases such as Parkinson's disease, spinal atrophy, amyotrophic lateral sclerosis, Alzheimer's disease, dementia, cerebrovascular dementia, AIDS dementia, and Meningitis; digestive diseases such as peptic ulcer, peptic esophagus ulcer, intestinal polyp, intestinal adhesion, intestinal rigidity, and gastric ulcer; sleep disturbances caused by the incidence of mental diseases, central nervous system depressants, habitual alcohols, and the disorder of respiratory system; and other diseases induced by side effects accompanied by the administration of hypnotics.

Agents combined with the SMIP compounds, contemplated to be useful in treating the aformentioned diseases include those well known in the art, such as, anesthetics, hypnotic sedatives, anti-anxieties, antiepileptics, antipyretic antiphlogistics, stimulants, wake amines, anti-parkinson drugs, agents for psychoneuroses, agents for central nervous system, skeletal muscle relaxants, agents for autonomic nervous system, antispastic agents, cytotoxic agents, monoclonal antibodies, drugs for eye, drugs for nose and ear, antivertiginous drugs, cardiotonics, antiarrhythmic drugs, diuretics, pressure reduction drugs, vasoconstrictors, coronary vaso-dilators, peripheral vasodilating drugs, hyperlipemia drugs, breath stimulants, antitussive and expectorant drugs, bronchodilators, drugs for allergy, antidiarrheal drugs, drugs for intestinal disorders, peptic ulcer drugs, stomachic digestants, antacids, cholagogouses, pituitary hormone drugs, salivary gland hormones, thyroid hormone drugs, antithyroid drugs, anabolic steroids, corticosteroids, androgen drugs, estrogen drugs, corpus luteum hormone drugs, mixed hormones, urinary/genital organ drugs, anus drugs, surgical sterilizations/antiseptics, wound protectives, externals for purulent diseases, analgesics, antipruritics, astringents, antiphlogistics, externals for parasite skin diseases, skin-softening drugs, caustics, dental/oral drugs, vitamins, inorganic preparations, supplemental liquids, hemostatics, anticoagulation drugs, drugs for liver diseases, antidotes, habitual intoxication drugs, drugs for treatment of gout, enzyme preparations, diabetic drugs, antioncotics, antihistaminics, drugs for stimulation treatment, antibiotics, chemotherapeutics, biological preparations, anthelmintics, anti-Protozoas, drugs for preparations, X-ray contrast media, and diagnostic drugs.

Further methods of the invention are provided wherein compositions described herein are used for the treatment of cancer and reduction of tumor growth. In one aspect a SMIP compound of the invention is combined with a known MAb for the treatment of cancer. In a presently preferred aspect of this embodiment of the present invention, an antibody and a SMIP compound are administered. It may be particularly preferred that said antibody, individually, has an inhibiting effect upon tumor cell growth and that the SMIP compound induces the production of cytokines.

In accordance with another embodiment of the present invention, there is provided a therapeutic composition for inhibiting tumor cell growth in a subject, which composition comprises an effective amount of a combination of at least a SMIP compound and a MAb and a pharmaceutically acceptable carrier, wherein said combination is more effective to inhibit growth of certain mammalian tumor cells than are either of the agents when administered individually.

In another embodiment methods of treating cancer are provided wherein known anticancer agents are combined with SMIP compounds to reduce tumor growth in a subject. A number of suitable anticancer agents are contemplated for use in the methods of the present invention. Indeed, the present invention contemplates, but is not limited to, administration of numerous anticancer agents such as: agents that induce apoptosis; polynucleotides (e.g., ribozymes); polypeptides (e.g., enzymes); drugs; biological mimetics; 25 alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons [e.g. IFN-a, etc.] and interleukins [e.g. IL-2, etc.], etc.); adoptive immunotherapy agents; hematopoietic growth factors; agents that induce tumor cell differentiation (e.g. all-trans-retinoic acid, etc.); gene 30 therapy reagents; antisense therapy reagents and nucleotides; tumor vaccines; and inhibitors of angiogenesis, and the like. Numerous other examples of chemotherapeutic compounds and anticancer therapies suitable for coadministration with the disclosed SMIP compounds are known to those skilled in the art.

In preferred embodiments, anticancer agents comprise agents that induce or stimulate apoptosis. Agents that induce apoptosis include, but are not limited to, radiation (e.g., W); kinase inhibitors (e.g., Epidermal Growth Factor Receptor [EGFR] kinase; inhibitor, Vascular Growth Factor Receptor [VGFR] kinase inhibitor, Fibroblast Growth 5 Factor Receptor [FGFR] kinase inhibitor, Platelet-derived Growth Factor Receptor [PGFR] I kinase inhibitor, and Bcr-Abl kinase inhibitors such as STI-571, Gleevec, and Glivec]); antisense molecules; antibodies [e.g., Herceptin and Rituxan]; anti-estrogens [e.g., raloxifene and tamoxifen]; anti-androgens [e.g., flutamide, bicalutamide, finasteride, aminoglutethamide, ketoconazole, and corticosteroids]; cyclooxygenase 2 (COX-2) inhibitors [e.g., Celecoxib, meloxicam, NS-398, and non-steroidal antiinflammatory drugs I (NSAIDs)]; and cancer chemotherapeutic drugs [e.g., irinotecan (Camptosar), CPT-11, fludarabine (Fludara), dacarbazine (DTIC), dexamethasone, mitoxantrone, Mylotarg, VP-; 16, cisplatinum, 5-FU, Doxrubicin, Taxotere or taxol]; cellular signaling molecules; ceramides and cytokines; and staurosprine, and the like.

In another embodiment methods of treating allergies are provided comprising administering a SMIP compound alone or in combination with at one other agent known to be effective against allergies, wherein said combination is more effective in treating an allergic condition than the know agent(s) are without the addition of said SMIP compound. In a more preferred embodiment the known agent is antihistamine and/or leukotriene inhibitor. In another preferred embodiment, the allergic condition is asthma. In another preferred embodiment, the allergic condition is selected from the group consisting of allergic rhinitis, dermatosis, and urticaria. In an even more preferred embodiment the combination is administered to a subject enterally, parenterally, intranasally, subcutaneously, or intraarterially.

In another embodiment, the present invention provides methods of screening a SMIP compound and a test compound comprising: providing a SMIP compound; a test compound; a first group of cells; and contacting the first group of cells with the SMIP compound and the test compound; and observing the effects of contacting the first group of cells with the SMIP compound and the test compound. In some of these embodiments, the present invention further provides the additional step of comparing the effects observed in the first cells against a second group of the cells contacted with the SMIP compound alone, or with the test compound alone. Effects that may be observed include, but are not limited to, changes in cell proliferation, changes in TNF alpha levels, changes in infected viral content of a cell, changes in bacterial infection levels in a cell, changes in histamine levels of a cell, changes in apoptotic stats, and changes in the expression of Bcl-2 family proteins, and the like.

In another embodiment methods of manufacturing compounds and compositions described herein are provided and contemplated to fall within the scope of the invention.

Qualitative and quantitative measurement of the immune response of a compound or composition can be implemented using methods known in the art, such as measuring antigen specific antibody production, activation of specific populations of lymphocytes such as CD4+, CD8+ T cells or NK cells, and/or production of cytokines such as IFN, IL-2, IL-4 or IL-12. Methods for measuring specific antibody responses include enzyme-linked immunosorbent assay (ELISA) as known in the art. Measurement of numbers of specific types of lymphocytes such as CD4+ T cells can be achieved, for example, with fluorescence-activated cell sorting (FACS). Cytotoxicity assays can be performed, e.g., as described in Raz et al., (1994) Proc. Natl. Acad. Sci. USA 91:9519-9523. Serum concentrations of cytokines can be measured, for example, by ELISA. Such assays are described, e.g., in Selected Methods in Cellular Immunology (1980) Mishell and Shiigi, eds., W.H. Freeman and Co.

In one embodiment, a compound or composition, such as a SMIP compound, is considered effective to elicit an immune response if a concentration of 20 µM (or alternatively 100 µM, or 200 µM, or 300 µM) of the SMIP compound causes the production of TNF-a in an in vitro cell based assay of human peripheral blood mononuclear cells, wherein the concentration of the human peripheral blood mononuclear cells is about 500,000/mL, and wherein the cells are exposed to the compound for about 18-24 hours, e.g., about 24 hours.

The above method of stimulating a local immune response for example in selected cells or tissues of a patient includes the stimulation of a local immune response wherein the selected cells or tissues are infected or cancerous. In one embodiment the selected cells or tissues are infected with a fungus or bacterium. In another embodiment the selected tissues are inflamed with an allergen, for example in an asthmatic condition. In another embodiment the selected cells are infected with a virus or bacteria. In still a more particular embodiment the infectious agent is HCV, HIV, HBV, HSV, *H. pylori*, HSV Type 1 or 2, or Human Papilloma Virus.

The methods and compounds disclosed herein can be used generally for the treatment of asthma by steering the immune response away from Type 2 cytokine secretion and effector mechanisms (e.g. IgE production and/or mast cell/basophil activation).

The immunogenic compositions of the invention can contain further pharmaceutically acceptable ingredients, excipients, carriers, and the like well known to those skilled in the art.

The vaccine composition may include an additional adjuvant. Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without specific immunostimulating agents such as muramyl peptides or bacterial cell wall components), such as, for example (a) MF59™ (WO90/14837), containing 5% squalene, 0.5% Tween 80, and 0.5% Span 85 (optionally containing MTP-PE) formulated into submicron particles using a microfluidizer, (b) SAF, containing 5% squalene, 0.5% Tween 80, 5% pluronic-blocked polymer L121, and thr-MDP either microfluidized into a submicron emulsion or vortexed to generate a larger particle size emulsion, and (c) Ribi™ adjuvant system (RAS), (Ribi immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+ CWS (Detox™); (3) saponin adjuvants, such as QS21 or Stimulon™ (Cambridge Bioscience, Worcester, Mass.) may be used or particles generated therefrom such as ISCOMs (immunostimulating complexes), which ISCOMs may be devoid of additional detergent e.g. WO00/07621; (4) Complete Freund's Adjuvant (CFA) and Incomplete Freund's Adjuvant (IFA); (5) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (6) momophosphoryl lipid A (MPL) or 3-O-deacylated MPL (3dMPL), optionally in the substantial absence of alum when used with pneumococcal saccharides e.g. WO00/56358; and RC529 (7) combinations of 3dMPL with, for example, QS21 and/or oil-in-water emulsions e.g. EP-A-0835318; (8) oligonucleotides comprising CpG motifs, i.e. containing at least one CG dinucleotide, with 5-methylcytosine optionally being used in place of cytosine; (9) a polyoxyethylene ether or a polyoxyethylene ester e.g. WO99/52549; (10) a polyoxyethylene sorbitan ester surfactant in combination with an octoxynol (WO0121207) or a polyoxyethylene alkyl ether or ester surfactant in combination with at least one additional non-ionic surfactant such as an octoxynol (WO01/21152); (11) a saponin and an immunostimulatory oligonucleotide (e.g. a CpG oligonucleotide) (WO00/62800); (12) an immunostimulant and a particle of metal salt e.g WO00/23105; (13) a saponin and an oil-in-water emulsion e.g. WO99/11241; (14) a saponin (e.g. QS21)+3dMPL+ IL-12 (optionally+a sterol) e.g. WO98/57659; (14) other substances that act as immunostimulating agents to enhance the effectiveness of the composition. In one particular embodiment, Alum (especially aluminium phospate and/or hydroxide) and MF59 are preferred for use with saccharide antigens.

The invention is also directed to administering the immunogenic composition. The vaccine is administered in an amount effective to stimulate an immune response. The amount that constitutes an effective amount depends, inter alia, on the particular vaccine used, the particular adjuvant compound being administered and the amount thereof, the immune response that is to be enhanced (humoral or cell mediated), the state of the immune system (e.g., suppressed, compromised, stimulated), and the desired therapeutic result. Accordingly it is not practical to set forth generally the amount that constitutes an effective amount of the vaccine. Those of ordinary skill in the art, however, can readily determine the appropriate amount with due consideration of such factors.

The immunogenic compositions of the invention can be administered to animals, e.g., mammals human and non-human, including, for example, pocket pets, fowl, and the like according to conventional methods well known to those skilled in the art (e.g., orally, subcutaneously, nasally, topically).

Suitable vaccines include, but are not limited to, any material that raises either humoral or cell mediated immune response, or both. Suitable vaccines include live viral and bacterial antigens and inactivated viral, tumor-derived, protozoal, organism-derived, fungal, and bacterial antigens, toxoids, toxins, polysaccharides, proteins, glycoproteins, peptides, and the like. Conventional vaccines, such as those used in connection with BCG (live bacteria), cholera, plague, and typhoid (killed bacteria), hepatitis B, influenza, inactivated polio, and rabies (inactivated virus), measles, mumps, rubella, oral polio, and yellow fever (live virus), tetanus and diphtheria (toxoids), hemophilus influenzae b, meningococcal, and pneumococcal (bacterial polysaccharides) also can be used. Any antigen known in the art or disclosed herein may be used.

Furthermore, it is contemplated that certain currently experimental vaccines, especially materials such as recombinant proteins, glycoproteins, and peptides that do not raise a strong immune response, will also find use in connection with the SMIP compound. Exemplary experimental subunit antigens include those related to viral disease such as adenovirus, AIDS, chicken pox, cytomegalovirus, dengue, feline leukemia, fowl plague, hepatitis A, hepatitis B, hepatitis C, HSV-1, HSV-2, hog cholera, influenza A, influenza B, Japanese encephalitis, measles, parainfluenza, rabies, respiratory syncytial virus, rotavirus, wart, and yellow fever.

Specific antigens for use with the invention include, but are not limited to, those listed below. The number(s) in parenthesis indicate representative resources of the antigen. The resource list follows the antigen list and each resource is incorporated by reference in its entirety.

Specific antigens include: a protein antigen from *N. meningitides* serogroup B (1-7); an outer-membrane vesicle (OMV) preparation from *N. meningitides* serogroup B. (8, 9, 10, 11); a saccharide antigen from *N. meningitides* serogroup A, C W135 and/or Y, such as the oligosaccharide (12) from serogroup C (13); a saccharide antigen from *Streptocaccus pneumoniae* (14, 15, 16); an antigen from *N. gonorrhoeae* (1, 2, 3); an antigen from *Chlamydia pneumoniae* (17, 18, 19, 20, 21, 22, 23); an antigen from *Chlamydia trachomatis* (24); an antigen from hepatitis A virus, such as inactivated virus (25, 26); an antigen from hepatitis B virus, such as the surface and/or core antigens (e.g. 26, 27); an antigen from hepatitis C virus (28); an antigen from *Bordetella pertussis*, such as petussis holotoxin (PT) and filamentous haemagglutinin (FHA) from *B. pertussis*, optionally also combination with pertactin and/or agglutinogens 2 and 3 (29, 30); a diphtheria antigen, such as a diphtheria toxoid (31:chapter 3) e.g. the $CRM_{197}$ mutant (32); a tetanus antigen, such as a tetanus toxoid (31 :chapter 4); a protein antigen from *Helicobacter pylori* such as CagA (33), VacA (33), NAP (34), HopX (5), HopY (35) and/or urease; a saccharide antigen from Haemophilus influenzae B (13); an antigen from *Porphyromonas gingivalis* (36); polio antigen(s) (37, 38) such as IPV or OPV; rabies antigen(s) (39) such lyophilized inactivated virus (40, RabAvert™); measles, mumps and/or rubella antigens (31: chapters 9, 10, & 11); influenza antigen(s) (31: chapter 19), such as the haemagglutinin and/or neuraminidase surface proteins; an antigen from *Moraxella catarrhalis* (41); an antigen from *Streptococcus agalactiae* (group B *streptococcus*) (42, 43); an antigen from *Streptococcus pyogenes* (group A streptococcus) (43, 44, 45); and an antigen from *Staphylococcus aureus* (46).

The composition may comprise one or more of the above antigens.

Where a saccharide or carbohydrate antigen is used, it is preferably conjugated to a carrier protein in order to enhance antigenicity (47-56). Preferred carrier proteins are bacterial toxine or toxoids, such as diphtheria or tetanus toxoids. The $CRM_{197}$ diphtheria toxoid is particularly preferred. Other suitable carrier proteins include the *N. meningitides* outer membrane protein (57), synthetic peptides (58, 59), heat shock proteins (60), pertussis proteins (61, 62), protein D from *H. influenzae* (63), toxin A or B from *C. difficile* (64) etc. Where a mixture comprises capsular saccharides from both serogroups A and C, it is preferred that the ratio (w/w) of MenA saccharide:MenC saccharide is greater than 1 (e.g. 2:1, 3:1, 4:4, 5:1, 10:1 or higher). Saccharides from different serogroups of *N. meningitides* may be conjugated to the same or different carrier proteins.

Any suitable conjugation reaction can be used, with any suitable linker where necessary. Toxic protein antigens may be detoxified where necessary (e.g. detoxification of pertussis toxin by chemical and/or genetic means (30)). Where a diphtheria antigen is included in the composition it is preferred also to include tetanus antigens and pertussis antigens. Similar, where a tetanus antigen is include it is preferred also to include diphtheria and pertussis antigens. Similar, where pertussis antigen is included it is preferred also to include diphtheria and tetanus antigens.

The pharmaceutical compositions containing the SMIP compounds described herein can include additives such as excipients. Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., N.J. (1991) or "Remington: The Science and Practice of Pharmacy," $20^{th}$ ed., Lippincott Williams & Wilkins, Baltimore, Md. (2000), incorporated herein by reference.

Pharmaceutical compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Other additives include immunostimulatory agents known in the art. Immunostimulatory oligonucleotides and polynucleotides are described in PCT WO 98/55495 and PCT WO 98/16247. U.S. Patent Application No. 2002/0164341 describes adjuvants including an unmethylated CpG dinucleotide (CpG ODN) and a non-nucleic acid adjuvant. U.S. Patent Application No. 2002/0197269 describes compositions comprising an antigen, an antigenic CpG-ODN and a polycationic polymer. Other immunostimulatory additives described in the art may be used, for example, as described in U.S. Pat. Nos. 5,026,546; 4,806,352; and 5,026,543.

A controlled release delivery system may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the invention may be administered enterally, orally, parenterally, sublingually, by inhalation spray, rectally, or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intramuscular, intraperitoneal, intranasal, subdermal, rectal, and the like. Topical administration may also involve the use of transdermal administration such as transdermal patches or ionophoresis devices. The term parenteral includes subcutaneous injections, intravenous, intramuscular, intrastemal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

As to the mode of administration, it should be emphasized that it is the combination of therapeutic agents that gives rise to its synergistic therapeutic effect no matter whether the first and the second agent are administered together or separately. Therefore, the two agents may be given together in a single dose or in separate ones with respect to space and time.

Effective amounts of the compounds of the invention generally include any amount sufficient to detectably treat viral infections.

Successful treatment of a subject in accordance with the invention may result in the inducement of a reduction or alleviation of symptoms in a subject afflicted with a medical or biological disorder to, for example, halt the further progression of the disorder, or the prevention of the disorder.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq (1976).

While the compounds of the invention can be administered as the sole active pharmaceutical agent, they can also be used in combination with one or more other agents used in the treatment of disorders. Representative agents useful in combination with the compounds of the invention for the treatment of viral infections include, for example, Interferon, Ribavirin, gancyclovir and the like.

When additional active agents are used in combination with the compounds of the present invention, the additional active agents may generally be employed in therapeutic amounts as indicated in the PHYSICIANS' DESK REFERENCE (PDR) $53^{rd}$ Edition (1999), that is incorporated herein by reference, or such therapeutically useful amounts as would be known to one of ordinary skill in the art.

The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

Compounds of the present invention can be readily synthesized using the methods described herein, or other methods, that are well known in the art.

The compounds can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylproionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylaamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

Various compounds and methods of their synthesis are disclosed in international patent application Publication Nos. WO02/18327 (benzamide and pyridylamide based compounds); WO0222598, and WO02/18383 (ABIQ based compounds); and WO 02/81443 (pthalamide base compounds), that have been found within context of this invention to be useful for immune potentiation. The entire disclosure of these U.S. and international publications is incorporated herein by this reference. Other compounds or intermediates of interest in the present invention were purchased from commercially available sources using the following method: the chemical structure of interest was drawn into the ACD-SC database (from MDL Information Systems). A search of the following companies/institutions, among others, retrieved the identified compound's supplier and purchasing information: ASDI, ASINEX, BIONET, CHEMBRIDGE, CHEMDIV, CHEMEX, CHEMSTAR, COMGENEX, CSC, INTERBIOSCREEN, LABOTEST, MAYBRIDGE, MICROSOURCE/GENESIS, OLIVIA, ORION, PEAKDALE, RYAN SCIENTIFIC, SPECS, TIMTEC, U OF FLORIDA, and ZELINSKY.

Antigen References:
1 International patent application WO99/24578
2 International patent application WO99/36544.
3 International patent application WO99/57280.
4 International patent application WO00/22430.
5 Tettelin et al. (2000) Science 287:1809-1815.
6 International patent application WO96/29412.
7 Pizza et al. (2000) Science 287:1816-1820.
8 PCT WO 01/52885.
9 Bjune et al. (1991) Lancet 338(8775).
10 Fuskasawa et al. (1999) Vaccine 17:2951-2958.
11 Rosenqist et al. (1998) Dev. Biol. Strand 92:323-333.
12 Constantino et al. (1992) Vaccine 10:691-698.
13 Constantino et al. (1999) Vaccine 17:1251-1263.
14 Watson (2000) Pediatr Infect Dis J 19:331-332.
15 Rubin (20000) Pediatr Clin North Am 47:269-285,v.
16 Jedrzejas (2001) Microbiol Mol Biol Rev 65:187-207.
17 International patent application filed on 3$^{rd}$ Jul. 2001 claiming priority from GB-0016363.4;WO 02/02606; PCT IB/01/00166.
18 Kalman et al. (1999) Nature Genetics 21:385-389.
19 Read et al. (2000) Nucleic Acids Res 28:1397-406.
20 Shirai et al. (2000) J. Infect. Dis 181(Suppl 3):S524-S527.
21 International patent application WO99/27105.
22 International patent application WO00/27994.
23 International patent application WO00/37494.
24 International patent application WO99/28475.
25 Bell (2000) Pediatr Infect Dis J 19:1187-1188.
26 Iwarson (1995) APMIS 103:321-326.
27 Gerlich et al. (1990) Vaccine 8 Suppl:S63-68 & 79-80.
28 Hsu et al. (1999) Clin Liver Dis 3:901-915.
29 Gastofsson et al. (1996) N. Engl. J. Med. 334-:349-355.
30 Rappuoli et al. (1991) TIBTECH 9:232-238.
31 Vaccines (1988) eds. Plotkin & Mortimer. ISBN 0-7216-1946-0.
32 Del Guidice et al. (1998) Molecular Aspects of Medicine 19:1-70.
33 International patent application WO93/018150.
34 International patent application WO99/533 10.
35 International patent application WO98/04702.
36 Ross et al. (2001) Vaccine 19:135-142.
37 Sutter et al. (2000) Pediatr Clin North Am 47:287-308.
38 Zimmerman & Spann (1999) Am Fan Physician 59:113-118, 125-126.
39 Dreensen (1997) Vaccine 15 Suppl"S2-6.
40 MMWR Morb Mortal Wkly rep Jan. 16, 1998:47(1):12, 9.
41 McMichael (2000) Vaccine19 Suppl 1:S101-107.
42 Schuchat (1999) Lancer 353(9146):51-6.
43 GB patent applications 0026333.5, 0028727.6 & 0105640.7.
44 Dale (1999) Infect Disclin North Am 13:227-43, viii.
45 Ferretti et al. (2001) PNAS USA 98: 4658-4663.
46 Kuroda et al. (2001) Lancet 357(9264):1225-1240; see also pages 1218-1219.
47 Ramsay et al. (2001) Lancet 357(9251):195-196.
48 Lindberg (1999) Vaccine 17 Suppl 2:S28-36.
49 Buttery & Moxon (2000) J R Coil Physicians Long 34:163-168.
50 Ahmad & Chapnick (1999) Infect Dis Clin North Am 13:113-133, vii.
51 Goldblatt (1998) J. Med. Microbiol. 47:663-567.
52 European patent 0 477 508.
53 U.S. Pat. No. 5,306,492.
54 International patent application WO98/42721.
55 Conjugate Vaccines (eds. Cruse et al.) ISBN 3805549326, particularly vol. 10:48-114.
56 Hermanson (1996) Bioconjugate Techniques ISBN: 012323368 & 012342335X.
57 European patent application 0372501.
58 European patent application 0378881.
59 European patent application 0427347.
60 International patent application WO93/17712.
61 International patent application WO98/58668.
62 European patent application 0471177.
63 International patent application WO00/56360.
64 International patent application WO00/67161.

The foregoing may be better understood by reference to the following Examples, Methods, and Schemes that are presented for illustration and not to limit the scope of the inventive concepts. Those groups of compounds that do not have experimental procedures relating to their synthesis are either commercially available, described by procedures incorporated herein by reference, or are easily synthesized by one skilled in the art from easily recognizable, commercially available starting materials.

All patents, patent applications and publications referred to herein are incorporated by reference in their entirety.

EXAMPLES

Benzazole Compounds

Scheme 1

Compounds of the invention containing a benzimidazole core may be prepared using a number of methods familiar to one of skill in the art. In one method, suitably functionalized diamines may be coupled with various thioisocyanates to form the intermediate thioureas. Cyclization to form the benzimidazole moiety may be effected under known conditions such as with treatment carbodiimides or alkyl halides. Alternatively the diamines may be reacted sequentially with carbonyl diimidazole and phosphoryl chloride followed by coupling with the appropriate amine.

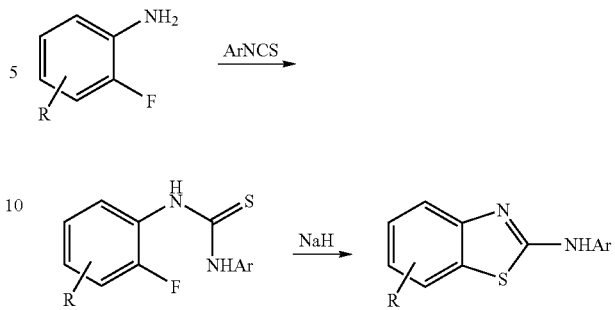

Benzothiazoles may generally be substituted in accordance with the present invention, such as through the following synthetic pathway:

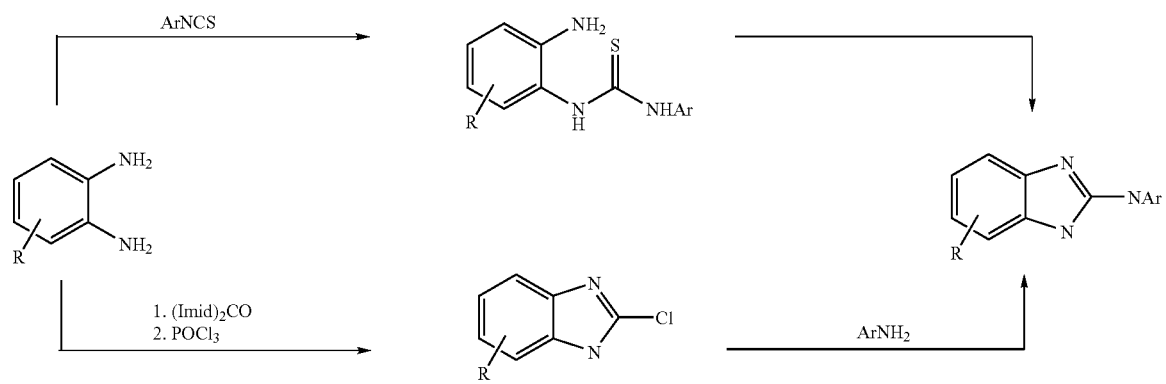

Compounds containing the oxazole structure may similarly be prepared according to the methods above or according to other known general procedures. Haviv et. al. (J. Med. Chem. 1988, 31, 1719) describes a procedure for assembling oxazole cores wherein a hydroxy aniline is treated with ethyl potassium xanthate. The resulting sulfuryl benzoxazole may then be chlorinated and coupled with an amine.

Compounds containing a benzothiazole core may also be prepared according to known methods. An ortho-halothioisocyanate may be reacted with an amine to form a thiourea. Reduction with NaH then allows formation of the thiazole ring.

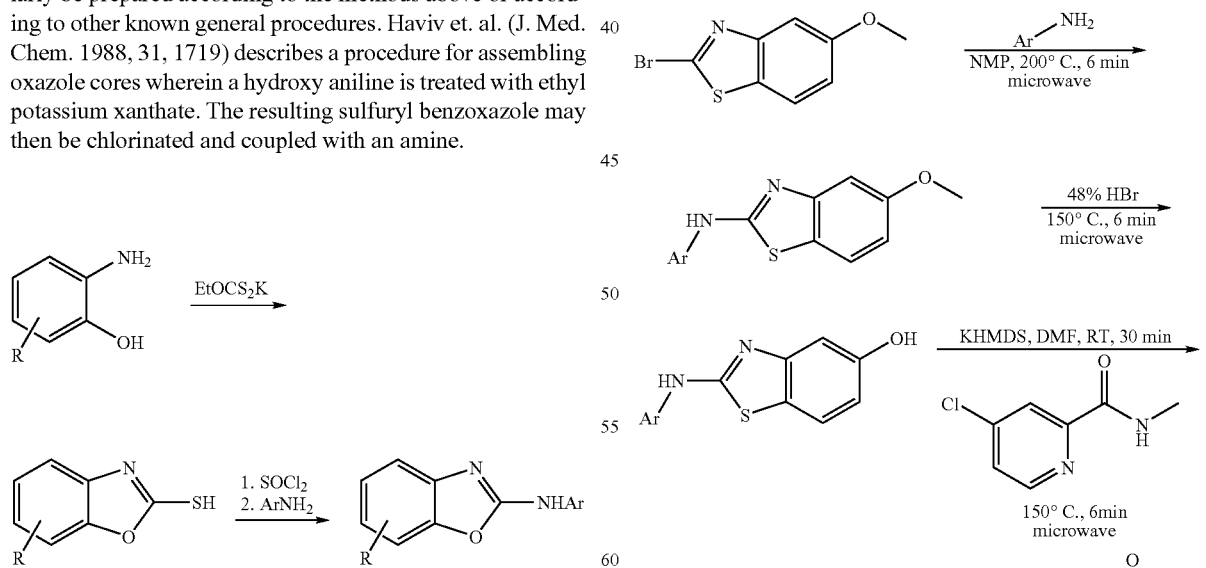

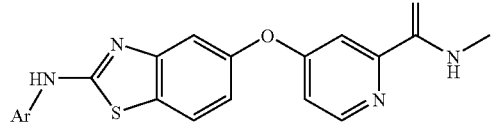

Example 1

Synthesis of 4-[(2-{[4-chloro-3-(trifluoromethyl)phenyl]amino}-1H-benzimidazol-6-yl)oxy]-N-methylpyridine-2-carboxamide The compound 4-[(2-{[4-chloro-3-(trifluoromethyl)phenyl]amino}-1H-benzimidazol-6-yl)oxy]—N-methylpyridine-2-carboxamide (159322) was synthesized as follows:

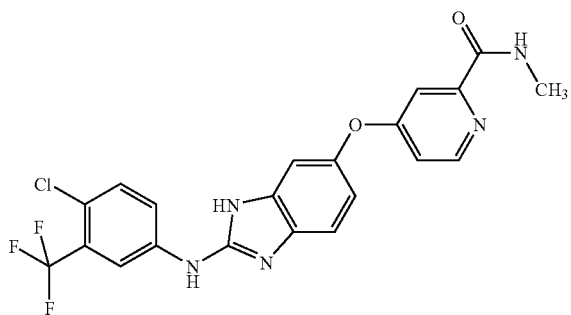

Step 1. Synthesis of 4-[(4-amino-3-nitrophenyl)oxy]-N-methylpyridine-2-carboxamide: A mixture containing 4-amino-3-nitrophenol (1 eq) and potassium bis(trimethylsilyl)amide (2eq) was stirred in dimethylformamide for 2 hours at room temperature. To this mixture was added (4-chloro(2-pyridyl))-N-methylcarboxamide (1 eq) and potassium carbonate (1.2eq) and stirred at 90° C. for 3 days. The reaction mixture was then concentrated and partitioned between ethyl acetate and water. The organic layer was separated and washed with brine, dried, filtered, and concentrated in vacuum to give brown solid. Purification on silica gel (2% triethyl amine/50% ethyl acetate in hexane) gave 4-[(4-amino-3-nitrophenyl)oxy]-N-methylpyridine-2-carboxamide as an orange solid. The product gave satisfactory NMR. HPLC, 3.39 min; MS: $MH^+=289$.

Step 2. Synthesis of 4-[(3,4-diaminophenyl)oxy]-N-methylpyridine-2-carboxamide: The mixture containing [4-(3-amino-4-nitrophenoxy)(2-pyridyl)]-N— in methanol with catalytic amount of 10%Pd/C was hydrogenated until disappearance of the yellow color to yield the product amine. HPLC, 2.5 mins; MS: $MH^+=259$.

Step 3. Synthesis of 4-[(2-{[4-chloro-3-(trifluoromethyl)phenyl]amino}-1H-benzimidazol-6-yl)oxy]-N-methylpyridine-2-carboxamide:

The mixture containing 4-[(3,4-diaminophenyl)oxy]-N-methylpyridine-2-carboxamide (1 eq) and 4-chloro-3-(trifluoromethyl)benzeneisothiocyanate (1 eq) in tetrahydrofuran was stirred at room temperature for 16 hours to give the corresponding thiourea. To the resulting mixture was added 1-ethyl-3-(3-dimethylaminopropyl)carbodiimide hydrochloride (2eq) and the mixture was stirred for another 10 hours. The mixture was concentrated and partitioned between ethyl acetate and water. The organic layer was washed with brine and dried. Purification on HPLC gave 4-[(2-{[4-chloro-3-(trifluoromethyl)phenyl]amino}-1H-benzimidazol-6-yl)oxy]-N-methylpyridine-2-carboxamide. MS: $MH^+=462$

Example 2

Synthesis of 4-({2-[(4-bromophenyl)amino]-1-methyl-1H-benzimidazol-5-yl}oxy)-N-methylpyridine-2-carboxamide The compound 4-({2-[(4-bromophenyl)amino]-1-methyl-1H-benzimidazol-5-yl}oxy)-N-methylpyridine-2-carboxamide (161651) was synthesized as follows:

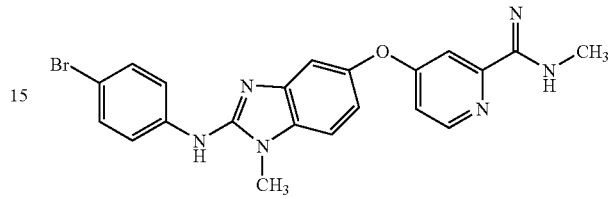

Step 1. Synthesis of 4-{[3-amino-4-(methylamino)phenyl]oxy}-N-methylpyridine-2-carboxamide: A solution of 4-[(4-amino-3-nitrophenyl)oxy]-N-methylpyridine-2-carboxamide (1 eq) in methylene chloride was treated with trifluoroacetic anhydride (1 eq) and stirred for 10 minutes at 0° C. The mixture was quenched with satd. $NaHCO_3$ solution. The organic layer was separated and washed with water, brine, dried and evaporated. MS: $MH^+=385.2$ To a solution of the trifluoroacetamide (1 eq) in a mixture of toluene, acetonitrile and sodium hydroxide solution (50%) was added benzyltrimethylammonium chloride (1 eq) and dimethyl sulfate (1.2 eq). The biphasic mixture was stirred overnight at room temperature and evaporated. The mixture was taken up in ethyl acetate, washed with water, brine, dried and evaporated. The crude product was purified by column chromatography eluting with 1:1 hexanes and ethylacetate followed by 2% triethylamine in 1:1 hexanes and ethyl acetate followed by 2% triethylamine in 1:1 hexanes and ethyl acetate to afford N-methyl-4-{[4-(methylamino)-3-nitrophenyl]oxy}pyridine-2-carboxamide as a reddish orange solid. MS: $MH^+=303.1$.

The solution of nitromethylaniline in methanol was treated with 5% palladium on carbon and stirred under hydrogen atmosphere for 15 min. (until the disappearance of yellow coloration) at room temperature. The mixture was filtered and the filtrate was concentrated to provide 0.36 g of the diamine 4-{[3-amino-4-(methylamino)phenyl]oxy}-N-methylpyridine-2-carboxamide. MS: $MH^+=273.3$.

Step 2. Synthesis of 4-({2-[(4-bromophenyl)amino]-1-methyl-1H-benzimidazol-5-yl}oxy)-N-methylpyridine-2-carboxamide: A solution of the diamine 4-{[3-amino-4-(methylamino)phenyl]oxy}-N-methylpyridine-2-carboxamide (1 eq) in methanol was treated with 4-bromophenylisothiocyanate (1 eq) and stirred at 60° C.-65° C. for 2 hours. The reaction mixture was cooled down to room temperature and methyl iodide (1 eq) was added and stirred overnight at 60° C. The reaction was cooled to room temperature, evaporated, taken up in ethyl acetate, and washed with water and brine, dried, and evaporated under reduced pressure. Column chromatography using a gradient solvent system of hexanes and ethyl acetate and either 1:1 methylene chloride and acetone or 5% methanol in methylene chloride yielded the product as a half white powder. MS: $MH^+=452.3$ Aminobenzimidazolylquinolinones Compounds of structure I may be synthesized from simple starting molecules as shown in Schemes 1-4 and exemplified in the Examples. As shown in Scheme 1, compounds of structure I may generally be prepared using aromatic compounds substituted with amines and carboxylic acid groups.

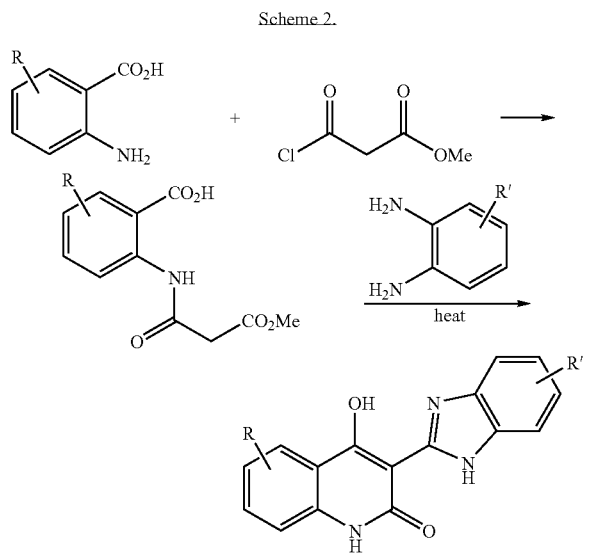

As shown in Scheme 2, a substituted aromatic compound such as a substituted or unsubstituted 2-aminobenzoic acid may be reacted with an acyl halide such as methyl 2-(chlorocarbonyl)acetate to produce an amide that will react with a substituted or unsubstituted 1,2-diaminobenzene. The resulting product is a 4-hydroxy-substituted compound of structure I. One skilled in the art will recognize that the procedure set forth in Scheme 1 may be modified to produce various compounds.

A method for preparing 4-amino substituted compounds of structure I is shown in Scheme 3. As shown in Scheme 3, aromatic compounds substituted with amine and nitrile groups may be used to synthesize 4-amino substituted compounds of structure I. A compound such as ethyl 2-cyanoacetate may be reacted with ethanol to produce ethyl 3-ethoxy-3-iminopropanoate hydrochloride. Subsequent reaction with a substituted or unsubstituted 1,2-phenylenediamine provides substituted or unsubstituted ethyl 2-benzimidazol-2-ylacetate. Reaction of a substituted or unsubstituted ethyl 2-benzimidazol-2-ylacetate with an aromatic compound having an amine and nitrile group such as substituted or unsubstituted 2-aminobenzonitrile with a base such as lithium bis(trimethylsilyl)amide or a Lewis acid such as tin tetrachloride provides the substituted or unsubstituted 4-amino substituted compound of structure I.

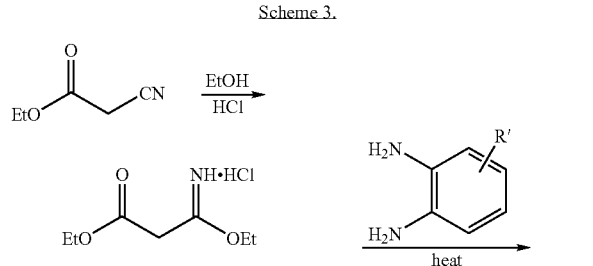

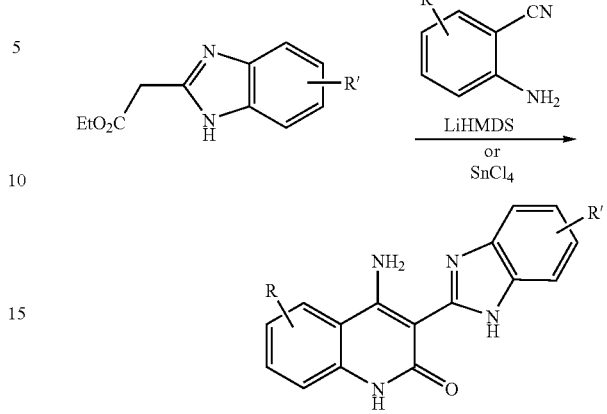

Scheme 4 illustrates a general synthetic route that allows for the synthesis of 4-dialkylamino and 4-alkylamino compounds of structure I. An inspection of Scheme 3 shows that 4-hydroxy substituted compounds of structure I may be converted into the 4-chloro derivative by reaction with phosphorous oxychloride or thionyl chloride. The 4-chloro derivative may then be reacted with an alkylamine or dialkylamine to produce the corresponding 4-alkylamino or 4-dialkylamino derivative. Deprotection affords the final 4-alkylamino or 4-dialkylamino compounds of structure I. Other groups that may be reacted with the 4-chloro derivative in this manner include, but are not limited to, ROH, RSH, and CuCN.

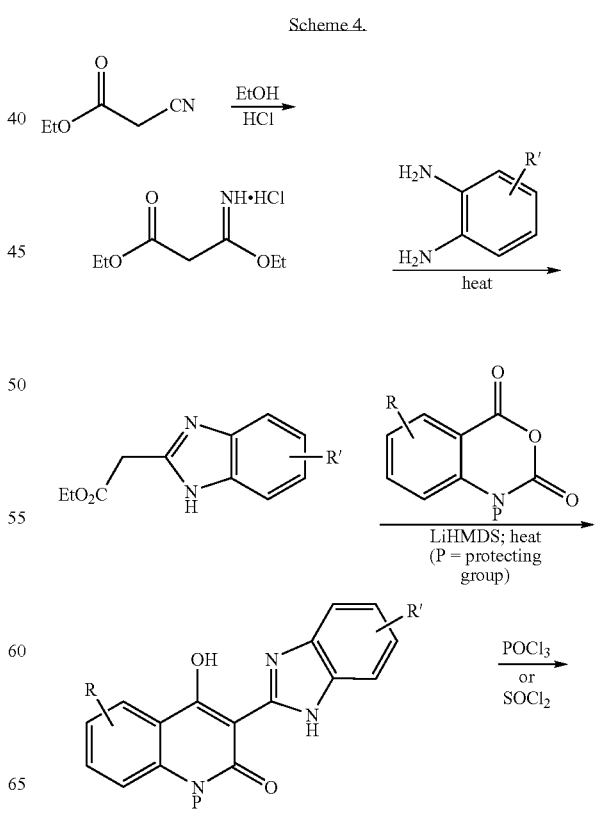

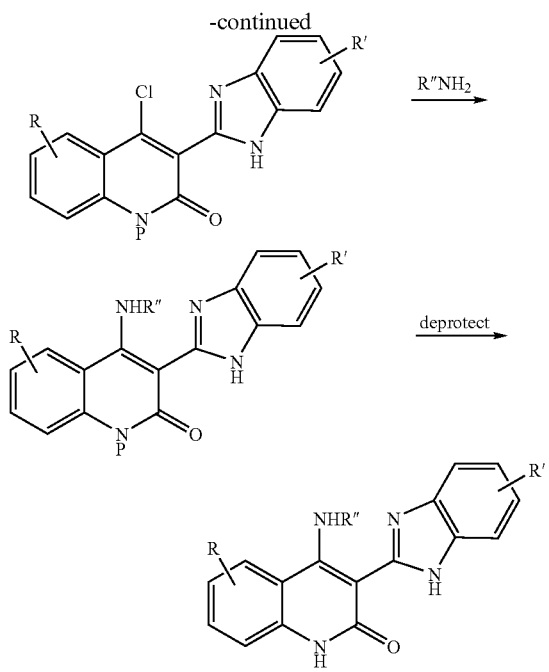

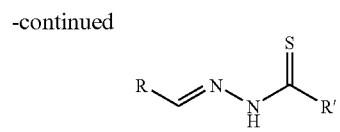

A solution of aldehyde (1.0 equiv.) and thiosemicarbazide (1.05 equiv.) in acetic acid was stirred overnight. Excess of acetic acid was removed to give a residue, that was washed with ethanol, or purified by preparative-HPLC to give the thiosemicarbazone.

Scheme 7

A solution of aldehyde (1.0 equiv.), thiosemicarbazide (1.05 equiv.) and acetic acid (0.1 equiv.) in methanol was stirred overnight. Methanol was removed to give a residue, that was worked up as in Scheme 6.

Scheme 8

To a solution of {[(1E)-1-aza-2-(4-fluoro-3-nitrophenyl) vinyl]amino}-aminomethane-1-thione in ethanol was added an arylamine (2.1 equiv.). The solution was stirred at room temperature until the starting fluoride disappeared. The solution was purified to the product.

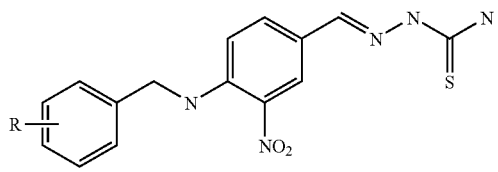

As shown in Scheme 5, the synthesis of compounds of structure I having a H, alkyl group, aryl group, or heterocyclyl group in the 4-position may be accomplished using a substituted or unsubstituted 2-benzimidazol-2-ylacetate prepared as shown in Schemes 3 and 4.

Scheme 5.

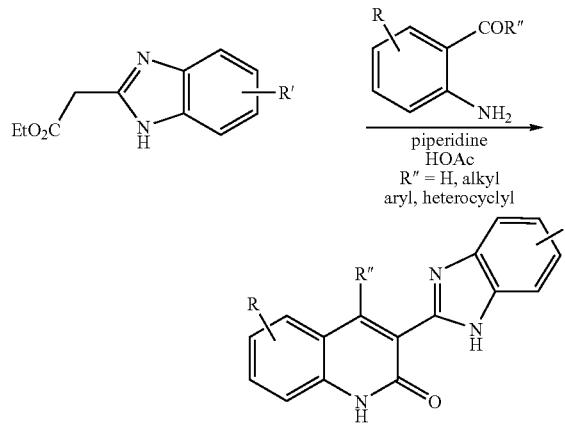

Thiosemcarbazones

General Procedure for the Preparation of Thiosemicarbazones

Scheme 9

A mixture of 4-(diethylamino)-2-hydroxybenzaldehyde (1 equiv.), benzylic bromide (1.2 equiv.) and powder potassium carbonate in ethanol was stirred at room temperature for 2 days. Ethanol was removed, and the residue was dissolved in ethyl acetate and water. The organic layer was washed with aqueous NaHCO$_3$ and brine, dried over Na$_2$SO$_4$., and concentrated. The residue, was purified on silica gel eluting with ethyl acetate/hexane to give 4-(diethylamino)-2-benzoxylic-benzaldehyde.

The aldehydes were converted to thiosemicarbazones according to Scheme 7.

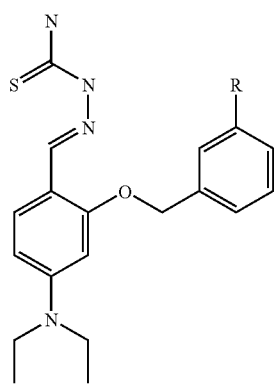

Scheme 6

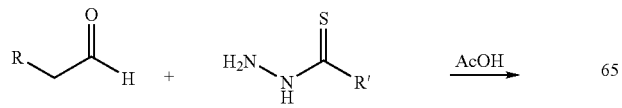

Scheme 10

A solution of 3,4-difluorobenzenecarbonitrile (1 equiv.), amine (1.5 equiv.) and DIEA (2 equiv.) in NMP was heated in a Smith Microwave (Personal Chemistry) for 30 minutes. The reaction mixture was purified on silica gel to give 4-substituted 3-fluorobenzenecarbonitrile.

To a solution of nitrile in toluene at −78° C. was added DIBAL-H (1 M in toluene, 1.5 equiv.). The reaction mixture was warmed to rt, and stirred for 16 h, and quenched with methanol/ethyl acetate/brine (1:1:4). After being stirred at rt for 30 min, the solution was extracted with ethyl acetate (3×). The combined organic layers were washed with aqueous $NaHCO_3$, brine and concentrated. The aldehyde was purified on silica gel or directly converted to thiosemicarbazones (Scheme 7).

Scheme 11

A solution of 2,4,5-trifluorobenzenecarbonitrile (1 equiv.) and 4-arylpiperazine (1.2 equiv.) and DIEA (1.2 equiv.) in THF was heated at 80° C. for 2 hours. The mixture was purified on silica gel to give 4-substituted 2,5-difluorobenzenecarbonitrile.

Scheme 12

To an alcohol (1.0 equiv) was added potassium t-butoxide in THF (1 M, 1.1 equiv). After 5 minutes, the solution was added to a solution of 4-N-substituted-2,5-difluorobenzenecarbonitrile (1 equiv.) in THF. The reaction mixture was stirred at rt overnight and quenched with aqueous ammonium chloride. The aqueous layer was extracted with ethyl acetate (3×). The combined organic layers were washed with brine, and concentrated to give a residue, that was purified to give 4-N-substituted-2-O-substituted-5-fluorobenzenecarbonitrile.

4-N-substituted-2-O-substituted-5-fluorobenzenecarbonitrile was reduced with DIBAL-H to give a 4-N-substituted-2-O-substituted-5-fluorobenzaldehyde according to procedure in Scheme 10.

The aldehyde was converted to the corresponding thiosemicarbazone using Scheme 7.

Scheme 13

A solution of 4-N-substituted-2,5-difluorobenzenecarbonitrile (1 equiv.), amine (1.5 equiv.) and DIEA (2 equiv.) in NMP was heated in a Smith Microwave (Personal Chemistry) for 30 minutes. The reaction mixture was purified on silica gel to give 4-N-substituted-2-N-substituted-5-fluorobenzenecarbonitrile.

4-N-substituted-2-N-substituted-5-fluorobenzenecarbonitrile was reduced with DIBAL-H according to procedure described in Scheme 10 to give 4-N-substituted-2-N-substituted-5-fluorobenzaldehyde.

Preparation of amino {3-[5-(3-chlorophenyl)(2-furyl)](2-pyrazolinyl)}methane-1-thione

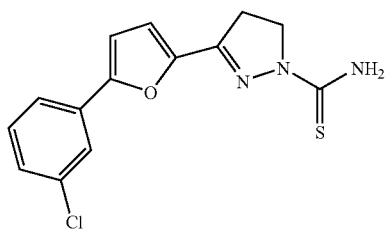

To a solution of 5-(3-chlorophenyl)furan-2-carbaldehyde (1.0 equiv.) in THF at 0° C. was added MeMgBr in ether (3.0 equiv.) and stirred for 45 min. The reaction was quenched with water, diluted with ether and filtered through Celite. The organic layer was separated and washed with brine, dried over $MgSO_4$, and concentrated to give the 1-[5-(3-chlorophenyl)-2-furyl]ethan-1-ol.

To a solution of secondary alcohol(1.0 equiv.) in $CH_2Cl_2$ was added $MnO_2$ (10 equiv.). The reaction was stirred overnight, filtered through Celite, and concentrated to give 1-[5-(3-chlorophenyl)-2-furyl]ethan-1-one.

To a mixture of ketone (1.0 equiv.), paraformaldehyde (2.0 equiv.), and dimethylamine hydrochloride (2.0 equiv) and molecular sieves in ethanol was added concentrated hydrochloric acid (cat.). The reaction was refluxed overnight under nitrogen and the concentrated. A few drops of HCl was added, and the mixture was worked up with DCM and water. The organic layer was discarded. The aqueous layer was adjusted to basic and extracted with DCM (3×). The organic layer was washed with brine, dried over $MgSO_4$, and concentrated to yield 3-(dimethylamino)-1-[5-(3-chlorophenyl)(2-furyl)]propan-1-one.

Thiosemicarbazide (1.0 equiv.) was dissolved in MeOH upon heating under nitrogen. Aqueous sodium hydroxide (6 M, 9.0 equiv.) was added to the reaction. A methanol solution of 3-(dimethylamino)-1-[5-(3-chlorophenyl)(2-furyl)]propan-1-one (1.0 equiv) was then added dropwise to the reaction mixture. The solvent was removed and the residue was dissolved in DCM and washed with water, brine, dried over $MgSO_4$, and concentrated. The final compound was purified by preparative-HPLC to give amino {3-[5-(3-chlorophenyl)(2-furyl)](2-pyrazolinyl)}methane-1-thione; LC/MS m/z 306.2 (MH+); Rt=3.06 minutes.

Scheme 14

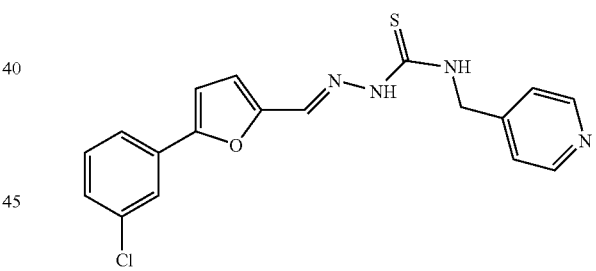

To a solution of 4-pyridylmethylamine (1.0 equiv.) and triethylamine (2.0 equiv.) in $CHCl_3$ was added $CS_2$ (1.0 equiv.)) and stirred overnight. The reaction was cooled to 0° C. and ethyl chloroformate (1.0 equiv.) was added dropwise. The reaction was stirred for 15 min at 0° C. and then stirred at room temperature for 2 hrs followed by addition of (tert-butyl)oxycarbohydrazide (1.2 equiv.). After stirring for an addition hour the mixture was washed with aqueous citric acid (5%), saturated $NaHCO_3$, brine, dried over $MgSO_4$, and concentrated. The desired Boc protected thiosemicarbazide was purified using column chromatography.

To a solution of Boc protected thiosemicarbazide (1.0 equiv.) dissolved in DCM was added HCl in dioxane (2M, 8.3 equiv.) and stirred for 15 min. MeOH is then added to dissolve the precipitate, followed by addition of the furfural, and small amount of acetic acid (0.5 mL). The mixture is stirred overnight and the solvents are removed to give a residue purified by preparative-HPLC to give the thiosemicarbazone.

Synthesis of 4-[4-(4-methylpiperazin-1-yl)phenoxymethyl]benzaldehyde

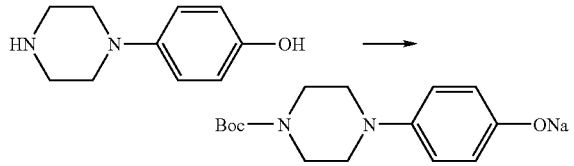

To a solution of 4-piperazin-1-yl phenol (1 equivalent) in CHCl₃, cooled to 0° C., was added di-t-butyl dicarbonate (1 equivalent) in CHCl₃ drop-wise. The solution was stirred at 0° C. for 1 hour before removing from the cold bath and stirring at ambient temperatures for 18 hours. The organic solution was washed aqueous NaHCO₃ and brine dried over MgSO₄ and concentrated the crude material was used without purification.

A solution of the resulting 4-(1-BOC-piperazin-4-yl)phenol (1 equivalent) in dry CH₃CN was slowly added drop-wise to a slurry of NaH (1 equivalent) in dry CH₃CN at room temperature under N₂. The slurry was stirred at room temperature for 2 hours before the solids were filtered and washed with Et₂O.

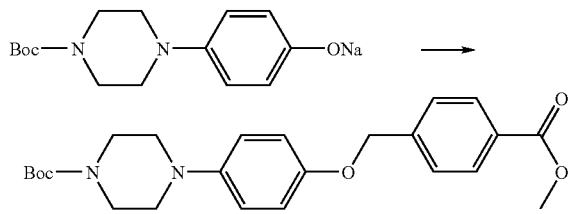

Sodium 4-(1-BOC-piperazin-4-yl)phenoxide (1 equivalent) and methyl 4-bromomethylbenzoate (1 equivalent) were combined in dry acetone and heated to reflux at 60° C. for 18 hours. The slurry was filtered and the filtrate was then concentrated to provide the crude methyl 4-[4-(1-BOC-piperazin-4-yl)phenoxymethyl]benzoate, that was used without purification.

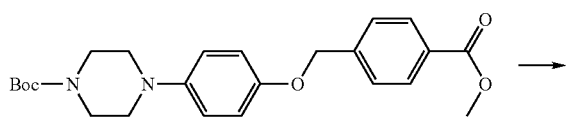

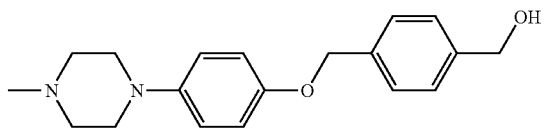

To a slurry of LiAlH₄ (4 equivalents) in dry THF, cooled to 0° C. under N₂, was slowly added drop-wise a solution of methyl 4-[4-(1-BOC-piperazin-4-yl)phenoxymethyl]benzoate (1 equivalent) in dry THF. Once the addition was complete, the slurry was heated to reflux at 80° C. for 1 hour. The slurry was subsequently cooled to 0° C. and treated with water, 10% aq. NaOH and with water again. The resulting solids were filtered, and the filtrate was diluted with chloroform, washed with brine, dried over MgSO₄ and concentrated, providing the crude 4-[4-(4-methylpiperazin-1-yl)phenoxymethyl]benzyl alcohol that was used without purification.

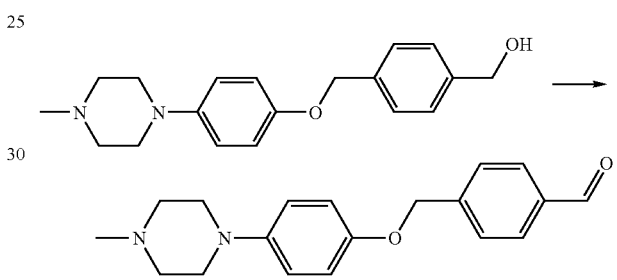

To a solution of DMSO (2.6 equivalents) in dry DCM, cooled to −78° C. under N₂ was added oxalyl chloride (1.1 equivalents) in DCM drop-wise. The solution was stirred at −78° C. for 5 minutes before a solution of 4-[4-(4-methylpiperazin-1-yl)phenoxymethyl]benzyl alcohol (1 equivalent) in DCM was added drop-wise, and allowed to stir at −78° C. for another 30 minutes. Triethylamine (2.5 equivalents) was slowly dripped in before allowing the solution to reach ambient temperatures. The solution was washed with aqueous NaHCO₃ and brine, dried over MgSO₄ and concentrated to provide the crude 4-[4-(4-methylpiperazin-1-yl)phenoxymethyl]benzaldehyde that was converted to thiosemicarbazones according to Scheme 7.

Pyrroles

Scheme 15
Synthesis of Pyrrole

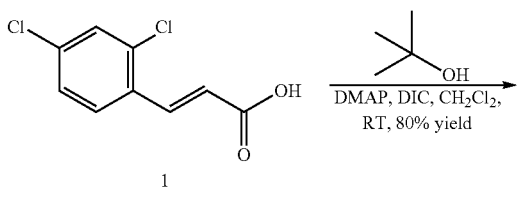

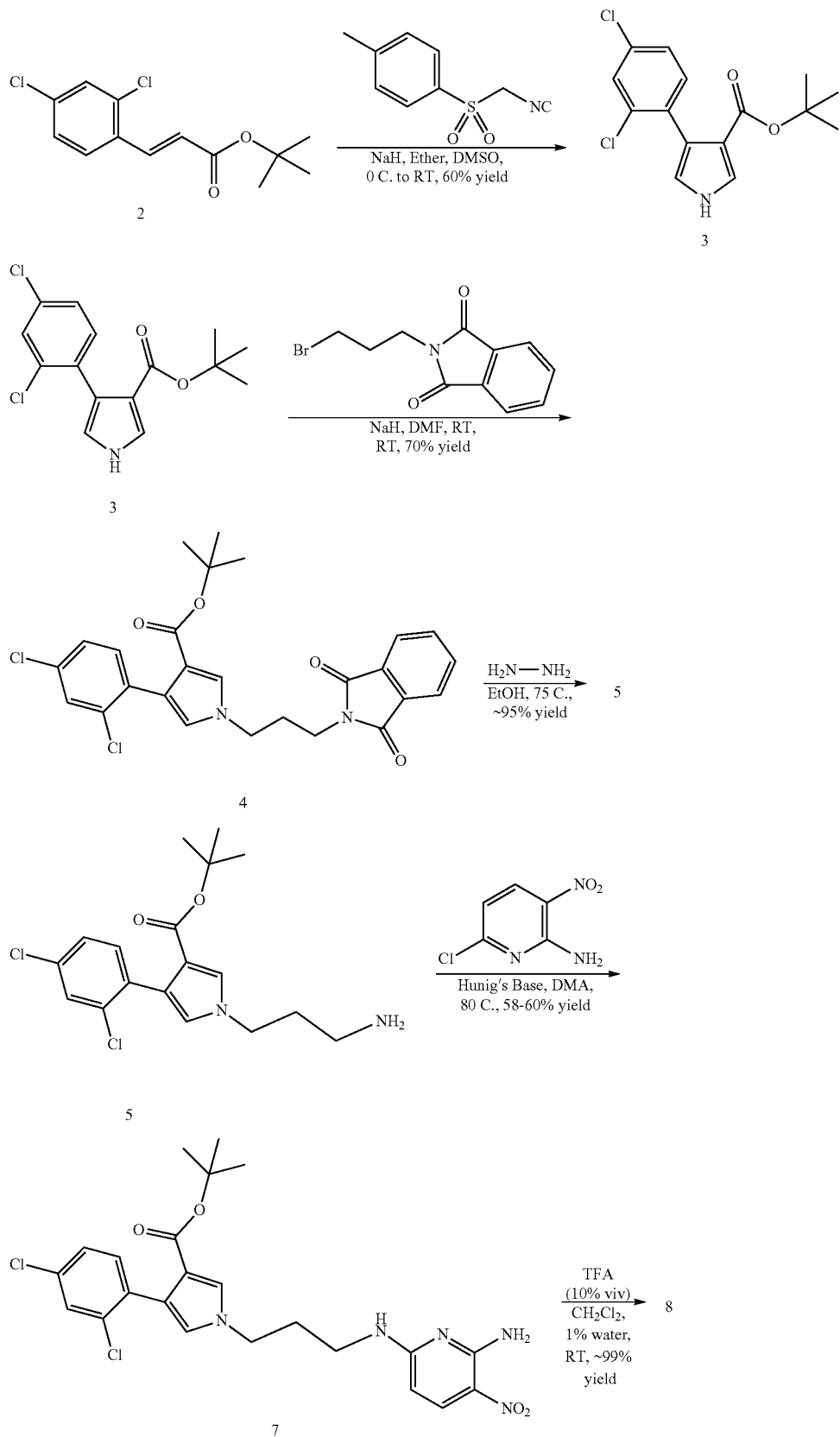

-continued
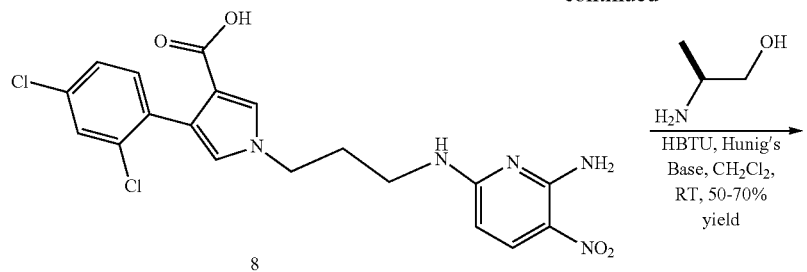
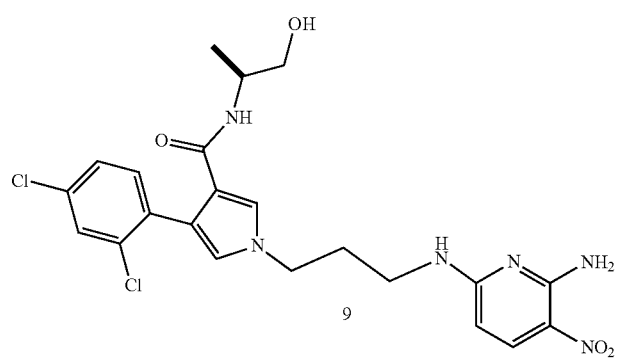
Purified by preparative HPLC
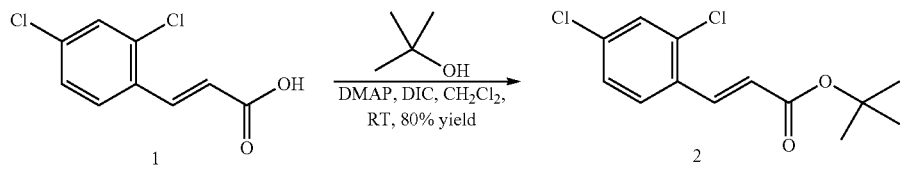
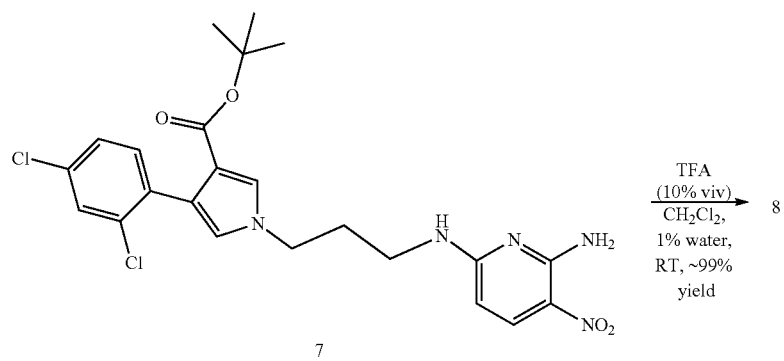
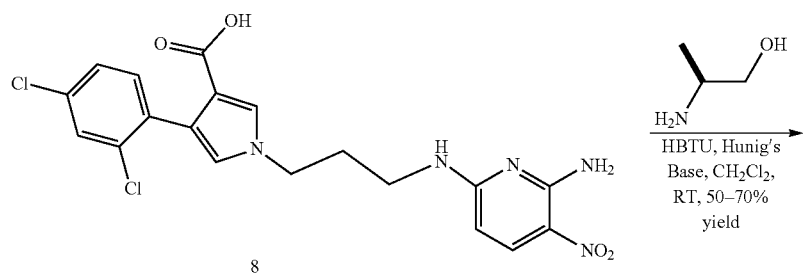

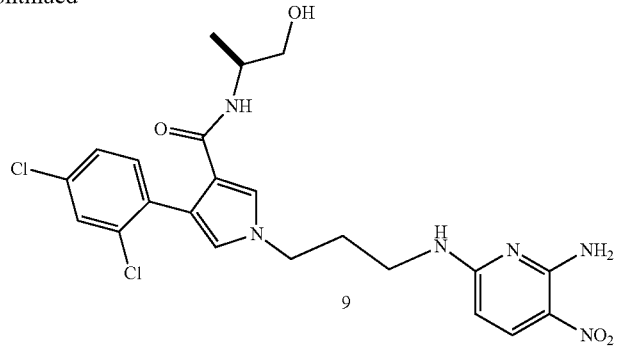

9

Purified by preparative HPLC

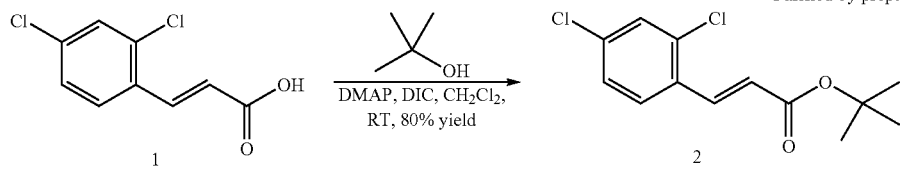

Preparation of tert-butyl (2E)-3-(2,4-dichlorophenyl)prop-2-enoate (2)

Neat DIC (1.4 eq) was added to a well stirred solution of cinnamate (1 eq), t-butyl alcohol (4 eq), DMAP (1.4 eq) and CH$_2$Cl$_2$ under argon at rt. (Note—The cinnamate must be completely in solution which may require gentle warming. Allow the solution to cool to room temperature before adding the DIC. To avoid an exotherm on larger scales, it may be prudent to dilute the DIC with CH$_2$Cl$_2$ before the addition and have an ice bath ready.) After stirring for 8 hours, the reaction develops a white precipitate. The reaction may be monitored by TLC eluting with 25% EtOAc/Hexane (Rf of product was 0.9). The entire reaction was loaded into a separatory funnel (washing with CH$_2$Cl$_2$). The organic mixture was washed with citrate, sat. aq. NaHCO$_3$, water, and brine. The organic layer was dried (Na$_2$SO$_4$), filtered, and concentrated to dryness to give the crude product as an oil. The crude oil was mixed with hexane and stirred for 30 min. The precipitate that forms was filtered over celite and the filtrate was evaporated. The hexane mixture was loaded onto a filter plug of silica and eluted with EtOAc/hexane (97:2 v/v). The first eluted UV active fractions are collected and evaporated to give >99% pure 2 (75-80% yields).

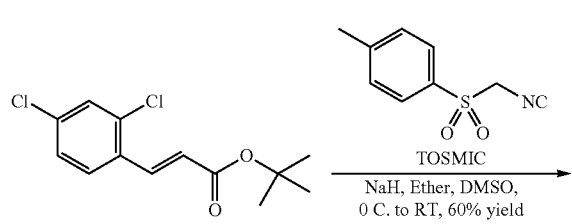

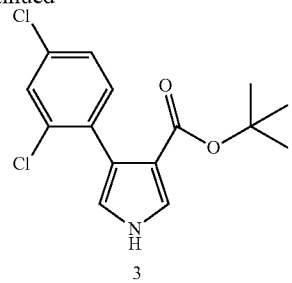

3

Preparation of tert-butyl 4-(2,4-dichlorophenyl)pyrrole-3-carboxylate (3)

Dry ether was added to NaH (1.5 eq as the oil dispersion) under argon. After decanting off the ether via syringe, the NaH was suspended again with fresh ether under argon. A solution of TOSMIC (1.1 eq) and 2 (1 eq) dissolved in a mixture of ether and DMSO was added dropwise to the stirred suspension of NaH at 0° C. over 20-30 min. The addition was mildly exothermic and evolved gas. After the addition, the reaction was allowed to warm to ambient rt. The progress of the reaction was followed by TLC (25% EtOAc/Hexane, the UV active product was at R$_f$=0.4) and LCMS until done (~2-3 h). Upon completion, the reaction was carefully quenched with sat. aq. NH$_4$Cl (added slowly to avoid strong gas evolution and exotherm) and diluted with ether. The layers were separated and the organic phase was washed with sat. aq. NaHCO$_3$, water, and brine. The crude dark solid can be purified by recrystallization. Best results were achieved either through recrystallization directly from a mixture of hot EtOAc/hexane (1:3 v/v) or by dissolving the crude product in minimal hot EtOAc followed by addition of hexane (~2 volumes of hexane based on the volume of EtOAc). The hot solutions were allowed to cool to room temperature and age over night. The crystals were first filtered and then washed with hexane giving 99% pure product in 60-70% yield.

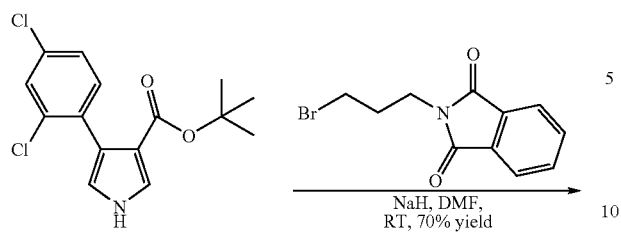

3

Preparation of tert-butyl 4-(2,4-dichlorophenyl)-1-
[3-(1,3-dioxobenzo[c]azolin-2-yl)propyl]pyrrole-3-
carboxylate (4)

Solid NaH (1.5 eq as the oil dispersion) was added in small portions to a solution of pyrrole 3 (1 eq) and 3-bromopropyl phthalimide (1.2 eq) dissolved in DMF stirred at room temperature and flushed with argon. NOTE—Some gas evolves, but the temperature does not seem to rise above 40-50° C. The reaction was stirred for 1.5 h at room temperature under argon. The reaction was followed by TLC (CH$_2$Cl$_2$/acetonitrile (95:5 v/v), the UV active product was at R$_f$=0.5) and LCMS. Upon completion, the reaction was quenched with sat. aq. NH$_4$Cl (add slowly to avoid strong gas evolution and exotherm). Sat. aq. NaHCO$_3$ was then added to avoid an emulsion, and the basic organic mixture was extracted with ether. The combined ether layers were washed with sat. aq. NaHCO$_3$, water, brine, dried Na$_2$SO$_4$, filtered, and concentrated to dryness to give the crude product. The crude product was purified by eluting through silica with EtOAc/Hexane (1:4 v/v). The purified product contained some residual 3-bromopropyl phthalimide, that did not interfere with subsequent synthetic steps. The material was taken on and used without further purification. Assume a quantitative yield.

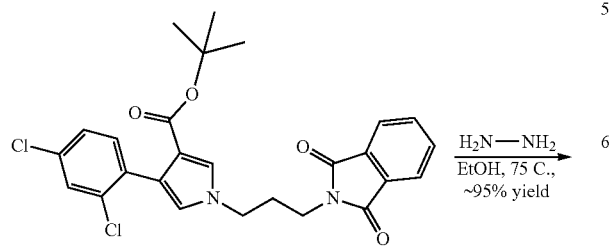

4

-continued

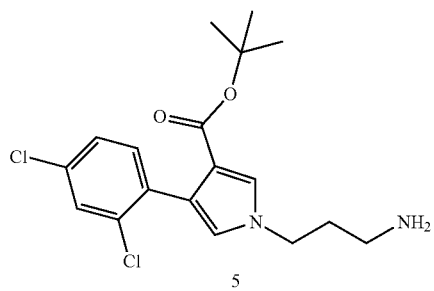

5

Preparation of tert-butyl 1-(3-aminopropyl)-4-(2,4-
dichlorophenyl)pyrrole-3-carboxylate (5)

The Pthalimido Pyrrole 4 (1 eq) was dissolved in ethanol and hydrazine (3 eq) at room temperature under nitrogen. Upon heating to reflux, the reaction generated a white precipitate. Stir at reflux until complete (~2 h) by TLC (CH$_2$Cl$_2$/acetonitrile (95:5 v/v), the UV active product was at R$_f$=0.2) and LCMS. Upon reaching completion, the reaction was allowed to cool to room temperature and the precipitate was vacuum-filtered off using a medium to fine cintered-glass filter. The filtrate was concentrated under reduced pressure to a gummy solid. The crude material was taken up in ethanol/EtOAc (1:1 v/v), stirred and the precipitate was filtered off in the same fashion as before. The filtrate was concentrated under reduced pressure and than dried in vacuo for 10-15 min. This process of adding ethanol/EtOAc, filtering and concentrating was done one more time or as needed to remove the majority of the white precipitate and residual hydrazine. The product was then dried in vacuo overnight. The material was used without further purification. Once dried, the reaction yielded the product as a glass (~87% yield over 2 steps).

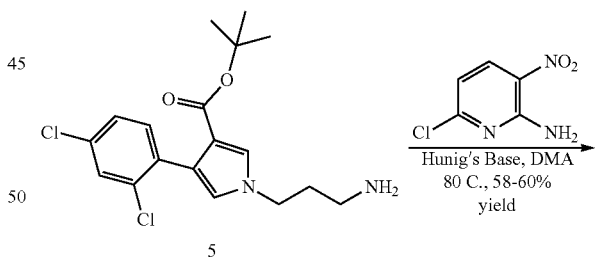

5

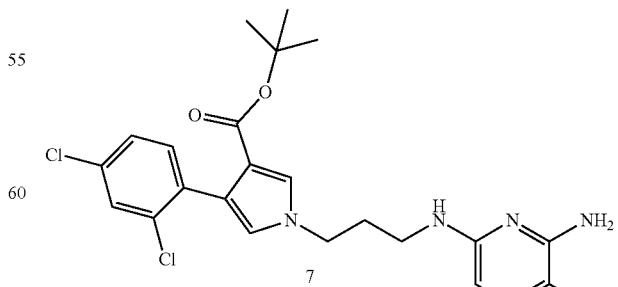

7

Preparation of tert-butyl 1-{3-[(6-amino-5-nitro(2-pyridyl))amino]propyl}-4-(2,4-dichlorophenyl)pyrrole-3-carboxylate (7)

To the premixed dry reagents, pyrrole 5 (1 eq) and powdered 6-chloro-3-nitro-2-pyridylamine (6) (1.1 eq), was added the DMA followed by Hünig's base (2 eq) sequentially with stirring at rt. The reaction was then heated to 80° C. overnight. The reaction was followed by TLC (EtOAc/hexane (1:1 v/v), the UV active yellow product was at $R_f$=0.25), HPLC and LCMS. Upon completion as judged by HPLC, the reaction was allowed to cool to 70° C. Ethylene diamine (anhydrous) was then added to the reaction to destroy any remaining unreacted chloropyridine 6. After 15 min stirring at 70° C., the reaction was cooled and quenched with the addition of sat. aq. NaHCO$_3$. The aqueous mixture was extracted with EtOAc, and the combined organic layers were washed with sat. aq. NaHCO$_3$, water, brine, dried, filtered, and concentrated to dryness to give the crude product as a brown-yellow solid. The crude product was purified by flash chromatography eluted with EtOAc/hexane (4:6 v/v). The purified SnAr adduct 7 was isolated in 58% yield as a yellow solid.

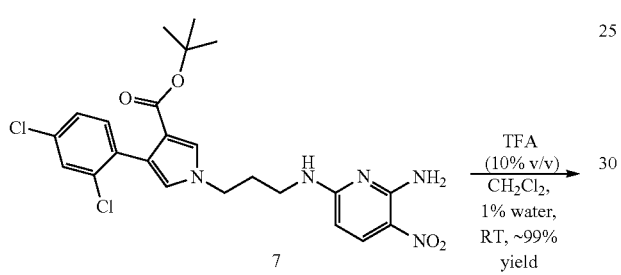

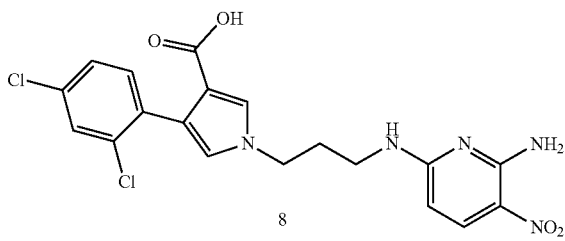

Preparation of 1-{3-[(6-amino-5-nitro(2-pyridyl))amino]propyl}-4-(2,4-dichlorophenyl)pyrrole-3-carboxylic acid (8)

In a vial, TFA (catalytic amount) was added to a stirred mixture of tert-butyl ester pyrrole 7 (1 eq), water (.1%), and CH$_2$Cl$_2$ at rt. The vial stirred at room temperature until done (~12 h. The reaction was then concentrated under reduced pressure at room temperature and dried in vacuo. The crude residue was dissolved again in CH$_2$Cl$_2$ and concentrated under reduced pressure at rt. The material was used in the final coupling step without further purification as the TFA salt.

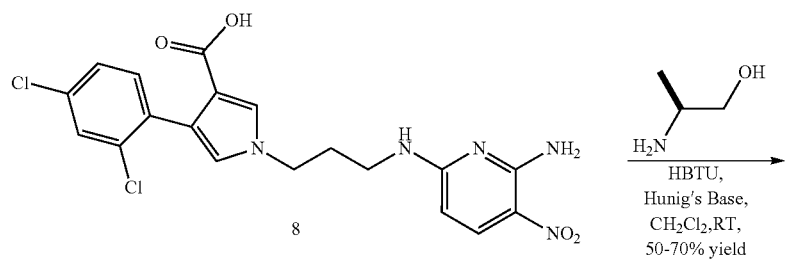

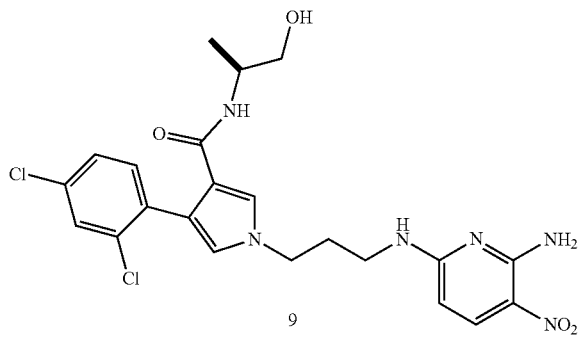

CHIR 154703

Preparation of N-((1S)-2-hydroxy-isopropyl)(1-{3-[(6-amino-5-nitro(2-pyridyl))amino]propyl}-4-(2,4-dichlorophenyl)pyrrol-3-yl)carboxantide (9,)

(2S)-(+)-2-Aminopropan-1-ol (1.5 eq) was added to a stirred mixture of acid (8) (1 eq), HBTU (1.5 eq), Hünig's base (2 eq) and DMF (premixed sequentially in this order in a vial) at room temperature under argon. The reaction was stirred for 3-4 h until complete as shown by LCMS and HPLC. The reaction mixture was subsequently diluted with EtOAc, washed with NaHCO$_3$, and concentrated to afford a powder in a 70% yield.

Nomenclature for the Example compounds was provided using ACD Name version 5.07 software (Nov. 14, 2001) available from Advanced Chemistry Development, Inc. Some of the compounds and starting materials were named using standard IUPAC nomenclature.

Examples 2-67 of Table 1 were synthesized following the synthetic methodology described above in the Examples and Schemes, and screened following the methods that directly follow the table. The precursors are readily recognizable by one skilled in the art and are commercially available from Aldrich (Milwaukee, Wis.) or Acros Organics (Pittsburgh, Pa.), among others.

TABLE 1

| Example | Structure | Name | MH+ |
|---|---|---|---|
| 2 | 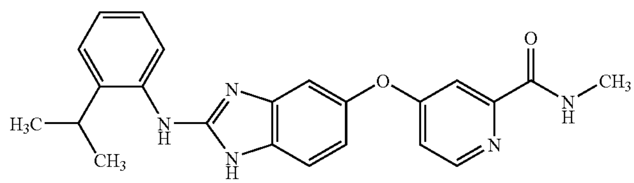 | N-methyl-4-[(2-{[2-(1-methylethyl)phenyl]amino}-1H-benzimidazol-5-yl)oxy]pyridine-2-carboxamide | 402.5 |
| 3 | 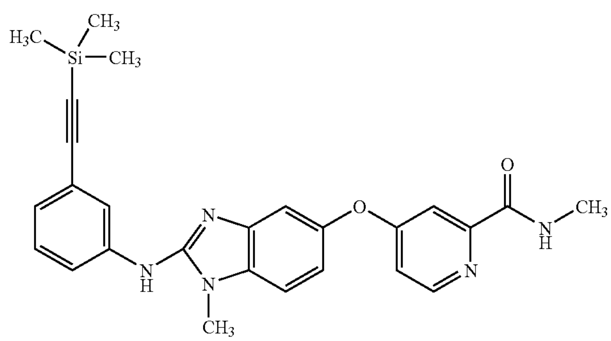 | N-methyl-4-{[1-methyl-2-({3-[(trimethylsilyl)ethynyl]phenyl}amino)-1H-benzimidazol-5-yl]oxy}pyridine-2-carboxamide | 470.6 |
| 4 | 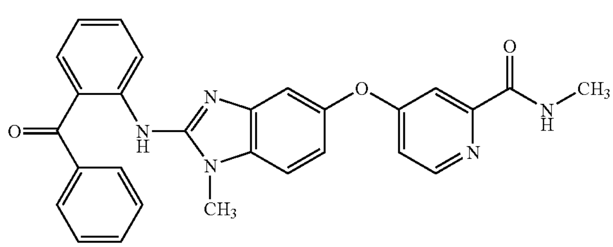 | N-methyl-4-[(1-methyl-2-{[2-(phenylcarbonyl)phenyl]amino}-1H-benzimidazol-5-yl)oxy]pyridine-2-carboxamide | 478.5 |
| 5 | 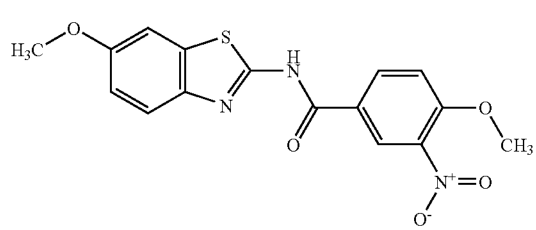 | 4-(methyloxy)-N-[6-(methyloxy)-1,3-benzothiazol-2-yl]-3-nitrobenzamide | 360.4 |
| 6 | 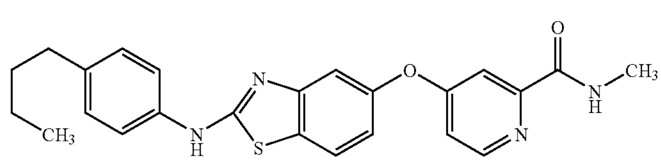 | 4-({2-[(4-butylphenyl)amino]-1,3-benzothiazol-5-yl}oxy)-N-methylpyridine-2-carboxamide | 433.5 |

TABLE 1-continued

| Example | Structure | Name | MH+ |
|---|---|---|---|
| 7 | 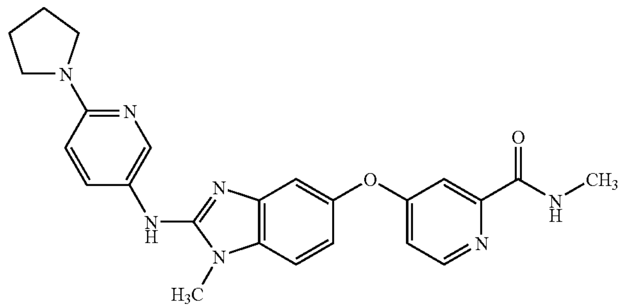 | N-methyl-4-({1-methyl-2-[(6-pyrrolidin-1-ylpyridin-3-yl)amino]-1H-benzimidazol-5-yl}oxy)pyridine-2-carboxamide | 444.5 |
| 8 | 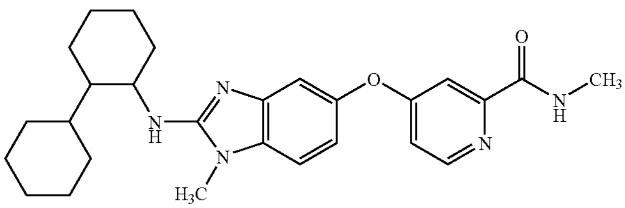 | 4-({2-(1,1'-bi(cyclohexyl)-2-ylamino]-1-methyl-1H-benzimidazol-5-yl}oxy)-N-methylpyridine-2-carboxamide | 462.6 |
| 9 | 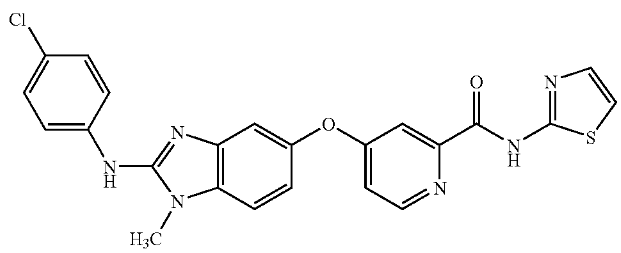 | 4-({2-[(4-chlorophenyl)amino]-1-methyl-1H-benzimidazol-5-yl}oxy)-N-1,3-thiazol-2-ylpyridine-2-carboxamide | 477.9 |
| 10 | 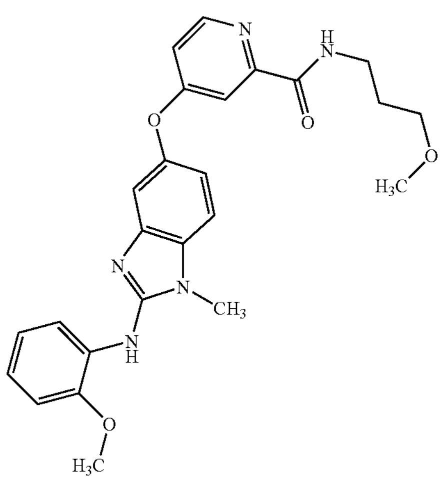 | 4-[(1-methyl-2-{[2-(methyloxy)phenyl]amino}-1H-benzimidazol-5-yl)oxy]-N-[3-(methyloxy)propyl]pyridine-2-carboxamide | 462.5 |
| 11 | 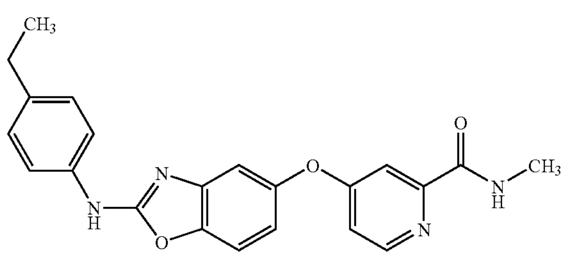 | 4-({2-[(4-ethylphenyl)amino]-1,3-benzoxazol-5-yl}oxy)-N-methylpyridine-2-carboxamide | 389.4 |

TABLE 1-continued

| Example | Structure | Name | MH+ |
|---|---|---|---|
| 12 | 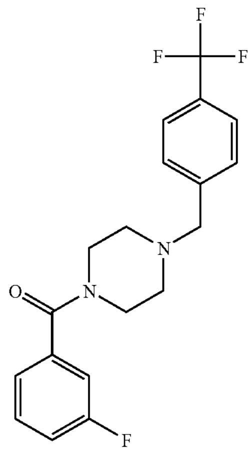 | 1-[(3-fluorophenyl)carbonyl]-4-{[4-(trifluoromethyl)phenyl]methyl}piperazine | 367.4 |
| 13 | 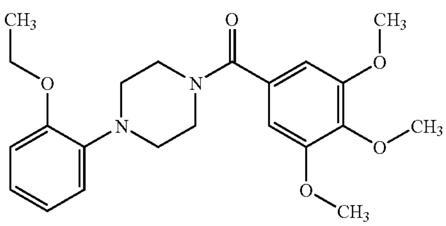 | 1-[2-(ethyloxy)phenyl]-4-{[3,4,5-tris(methyloxy)phenyl]carbonyl}piperazine | 401.5 |
| 14 | 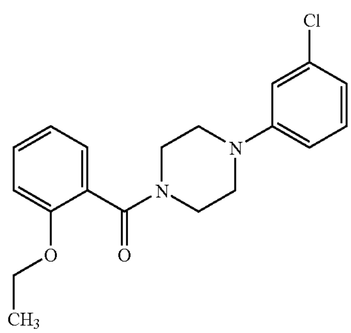 | 1-(3-chlorophenyl)-4-{[2-(ethyloxy)phenyl]carbonyl}piperazine | 345.8 |
| 15 | 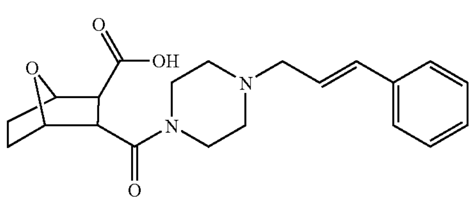 | 3-({4-[(2E)-3-phenylprop-2-enyl]piperazin-1-yl}carbonyl)-7-oxabicyclo[2.2.1]heptane-2-carboxylic acid | 371.4 |
| 16 | 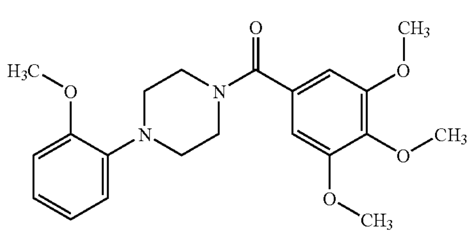 | 1-[2-(methyloxy)phenyl]-4-{[3,4,5-tris(methyloxy)phenyl]carbonyl}piperazine | 387.4 |

TABLE 1-continued

| Example | Structure | Name | MH+ |
|---|---|---|---|
| 17 | 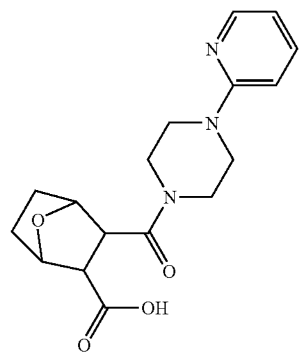 | 3-[(4-pyridin-2-ylpiperazin-1-yl)carbonyl]-7-oxabicyclo[2.2.1]heptane-2-carboxylic acid | 332.4 |
| 18 | 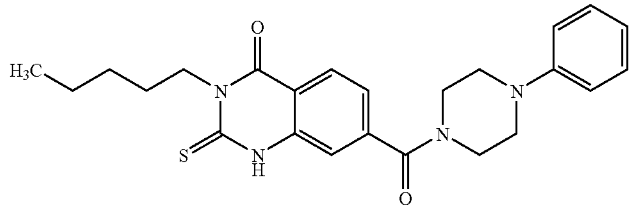 | 3-pentyl-7-[(4-phenylpiperazin-1-yl)carbonyl]-2-thioxo-2,3-dihydroquinazolin-4(1H)-one | 437.6 |
| 19 | 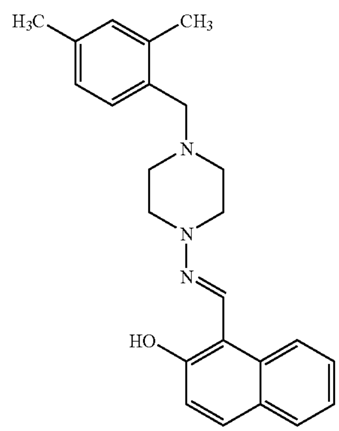 | 1-[(E)-({4-[(2,4-dimethylphenyl)methyl]piperazin-1-yl}imino)methyl]naphthalen-2-ol | 374.5 |
| 20 | 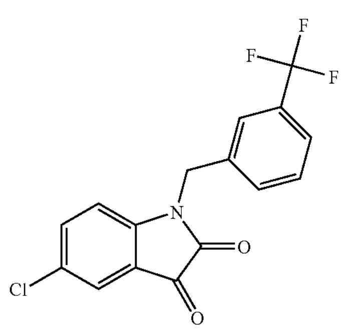 | 5-chloro-1-{[3-(trifluoromethyl)phenyl]methyl}-1H-indole-2,3-dione | 340.7 |
| 21 | 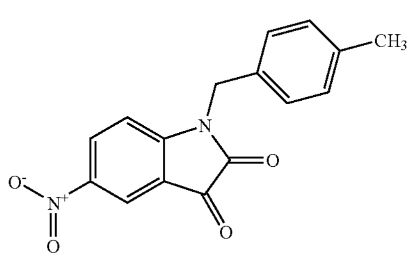 | 1-[(4-methylphenyl)methyl]-5-nitro-1H-indole-2,3-dione | 297.3 |

TABLE 1-continued

| Example | Structure | Name | MH+ |
|---|---|---|---|
| 22 | 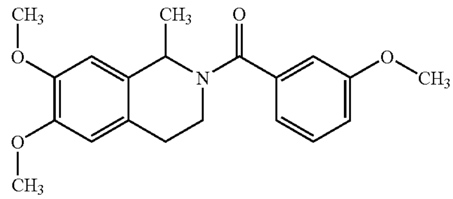 | 1-methyl-6,7-bis(methyloxy)-2-{[3-(methyloxy)phenyl]carbonyl}-1,2,3,4-tetrahydroisoquinoline | 342.4 |
| 23 | 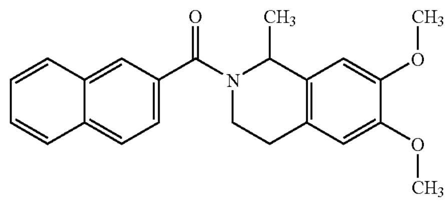 | 1-methyl-6,7-bis(methyloxy)-2-(naphthalen-2-ylcarbonyl)-1,2,3,4-tetrahydroisoquinoline | 362.4 |
| 24 | 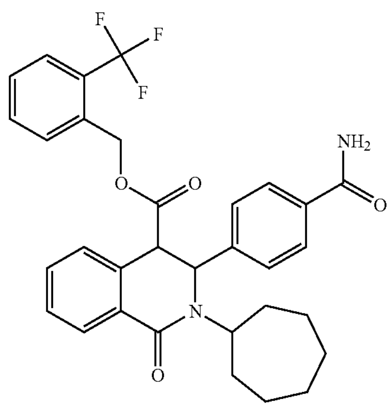 | [2-(trifluoromethyl)phenyl]methyl-3-[4-(aminocarbonyl)phenyl]-2-cycloheptyl-1-oxo-1,2,3,4-tetrahydroisoquinoline-4-carboxylate | 565.6 |
| 25 | 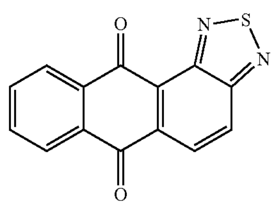 | anthra[1,2-c][1,2,5]thiadiazole-6,11-dione | 267.3 |
| 26 | 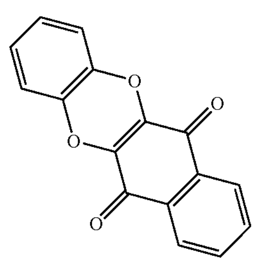 | benzo[b]oxanthrene-6,11-dione | 265.2 |
| 27 | 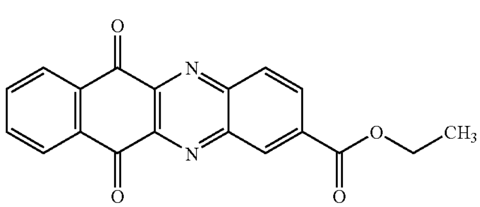 | ethyl 6,11-dioxo-6,11-dihydrobenzo[b]phenazine-2-carboxylate | 333.3 |

TABLE 1-continued

| Example | Structure | Name | MH+ |
|---|---|---|---|
| 28 | 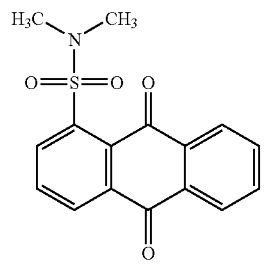 | N,N-dimethyl-9,10-dioxo-9,10-dihydroanthracene-1-sulfonamide | 316.3 |
| 29 | 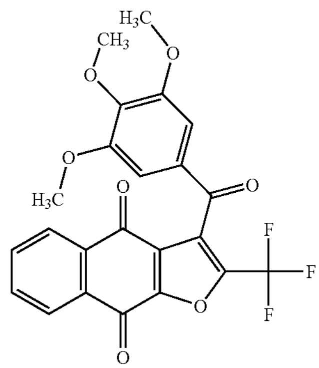 | 2-(trifluoromethyl)-3-{[3,4,5-tris(methyloxy)phenyl]carbonyl}naphtho[2,3-b]furan-4,9-dione | 461.4 |
| 30 | 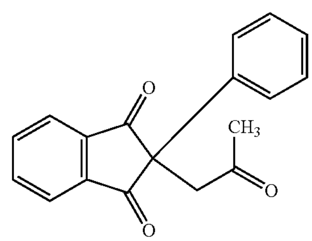 | 2-(2-oxopropyl)-2-phenyl-1H-indene-1,3(2H)-dione | 279.3 |
| 31 | 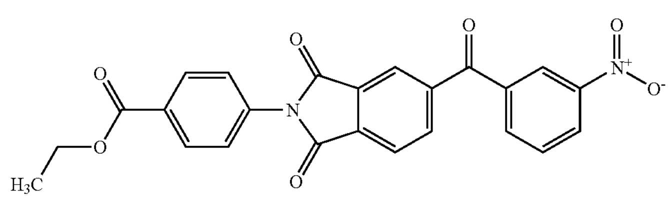 | ethyl 4{5-[(3-nitrophenyl)carbonyl]-1,3-dioxo-1,3-dihydro-2H-isoindol-2-yl}benzoate | 445.4 |
| 32 | 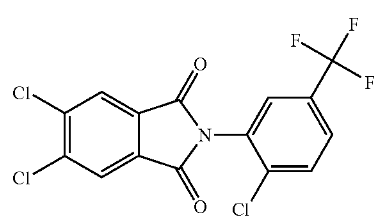 | 5,6-dichloro-2-[2-chloro-5-(trifluoromethyl)phenyl]-1H-isoindole-1,3(2H)-dione | 395.6 |
| 33 | 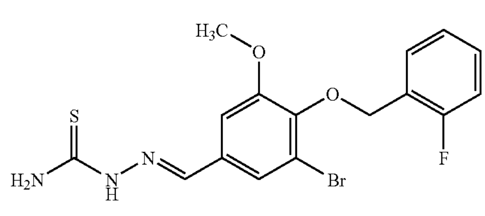 | 3-bromo-4-{[(2-fluorophenyl)methyl]oxy}-5-(methyloxy)benzaldehydethiosemicarbazone | 413.3 |

TABLE 1-continued

| Example | Structure | Name | MH+ |
|---|---|---|---|
| 34 | 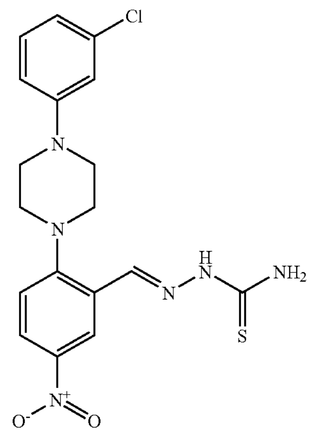 | 2-[4-(3-chlorophenyl)piperazin-1-yl]-5-nitrobenzaldehyde thiosemicarbazone | 419.9 |
| 35 | 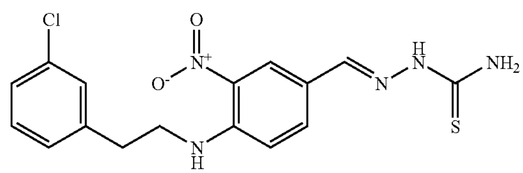 | 4-{[2-(3-chlorophenyl)ethyl]amino}-3-nitrobenzaldehyde thiosemicarbazone | 378.9 |
| 36 | 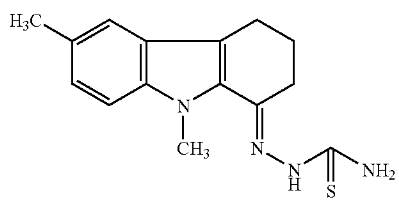 | (1E)-6,9-dimethyl-2,3,4,9-tetrahydro-1H-carbazol-1-one thiosemicarbazone | 287.4 |
| 37 | 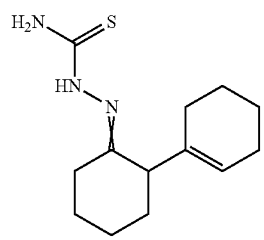 | (2E)-1,1'-bi(cyclohexan)-1-en-2-one thiosemicarbazone | 252.4 |
| 38 | 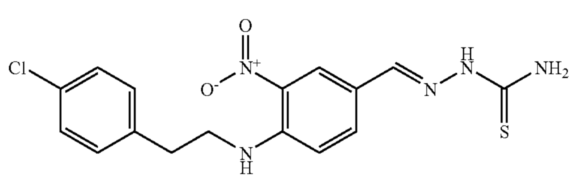 | 4-{[2-(4-chlorophenyl)ethyl]amino}-3-nitrobenzaldehyde thiosemicarbazone | 378.9 |
| 39 | 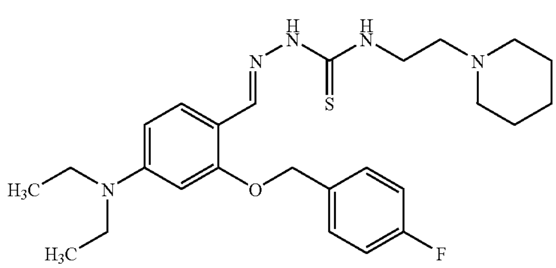 | 4-(diethylamino)-2-{[(4-fluorophenyl)methyl]oxy}benzaldehyde N-(2-piperidin-1-ylethyl) thiosemicarbazone | 486.7 |

TABLE 1-continued

| Example | Structure | Name | MH+ |
|---|---|---|---|
| 40 | 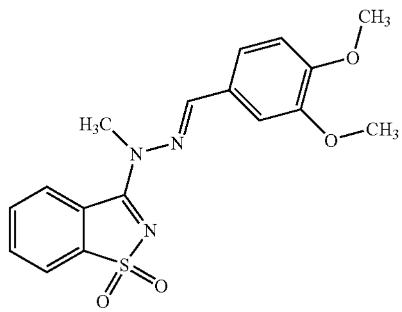 | 3,4-bis(methyloxy)benzaldehyde (1,1-dioxido-1,2-benzisothiazol-3-yl)(methyl)hydrazone | 360.4 |
| 41 | 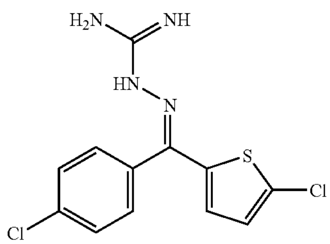 | (2E)-2-[(4-chlorophenyl)(5-chlorothien-2-yl)methylidene]hydrazinecarboximidamide | 314.2 |
| 42 | 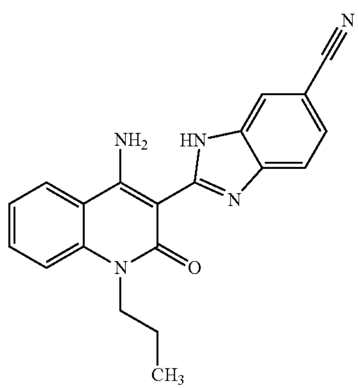 | 2-(4-amino-2-oxo-1-propyl-1,2-dihydroquinolin-3-yl)-1H-benzimidazole-6-carbonitrile | 344.4 |
| 43 | 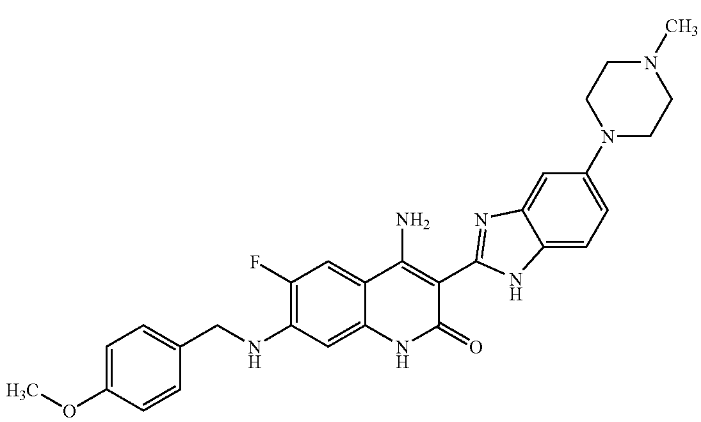 | 4-amino-6-fluoro-7-({[4-(methyloxy)phenyl]methyl}amino)-3-[5-(4-methylpiperazin-1-yl)-1H-benzimidazol-2-yl]quinolin-2(1H)-one | 528.6 |

TABLE 1-continued

| Example | Structure | Name | MH+ |
|---|---|---|---|
| 44 | 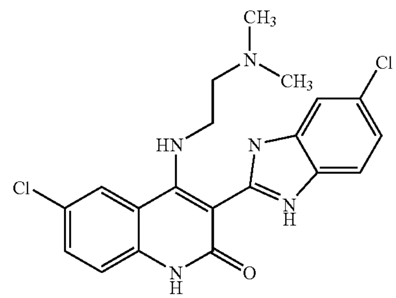 | 6-chloro-3-(5-chloro-1H-benzimidazol-2-yl)-4-{[2-(dimethylamino)ethyl]amino}quinolin-2(1H)-one | 417.3 |
| 45 | 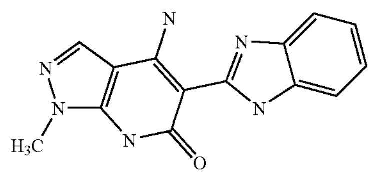 | 4-amino-5-(1H-benzimidazol-2-yl)-1-methyl-1,7-dihydro-6H-pyrazolo[3,4-b]pyridin-6-one | 281.3 |
| 46 | 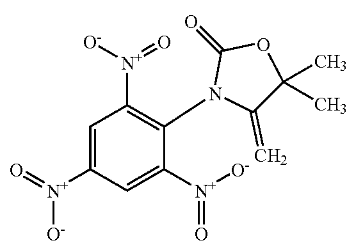 | 5,5-dimethyl-4-methylidene-3-(2,4,6-trinitrophenyl)-1,3-oxazolidin-2-one | 339.2 |
| 47 | 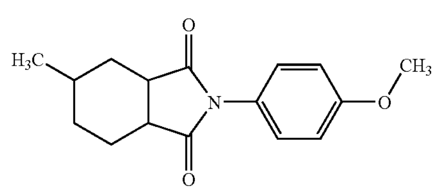 | 5-methyl-2-[4-(methyloxy)phenyl]hexahydro-1H-isoindole-1,3(2H)-dione | 274.3 |
| 48 | 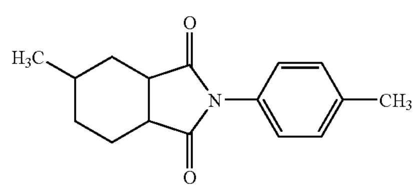 | 5-methyl-2-(4-methylphenyl)hexahydro-1H-isoindole-1,3(2H)-dione | 258.3 |
| 49 | 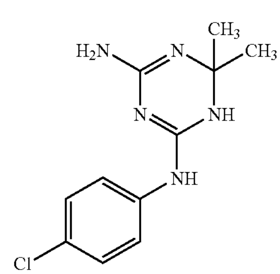 | N~2~-(4-chlorophenyl)-6,6-dimethyl-1,6-dihydro-1,3,5-triazine-2,4-diamine | 252.7 |

TABLE 1-continued

| Example | Structure | Name | MH+ |
|---|---|---|---|
| 50 | 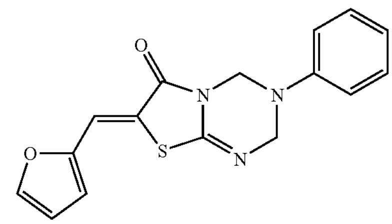 | (7Z)-7-(furan-2-ylmethylidene)-3-phenyl-3,4-dihydro-2H-[1,3]thiazolo[3,2-a][1,3,5]triazin-6(7H)-one | 312.4 |
| 51 | Chiral | (3aR,9R,9aR)-6,7-dihydroxy-9-[3,4,5-tris(methyloxy)phenyl]-3a,4,9,9a-tetrahydronaphtho[2,3-c]furan-1(3H)-one | 387.4 |
| 52 | 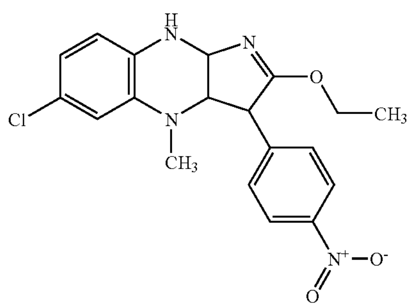 | 6-chloro-2-(ethyloxy)-4-methyl-3-(4-nitrophenyl)-3a,4,9,9a-tetrahydro-3H-pyrrolo[2,3-b]quinoxaline | 387.8 |
| 53 | 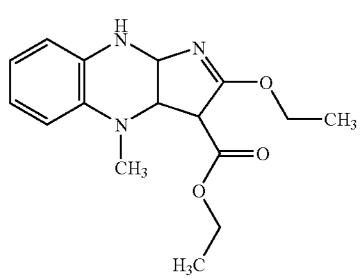 | ethyl 2-(ethyloxy)-4-methyl-3a,4,9,9a-tetrahydro-3H-pyrrolo[2,3-b]quinoxaline-3-carboxylate | 304.4 |
| 54 | 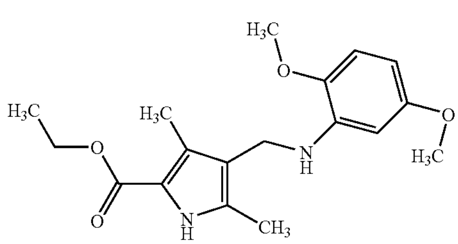 | ethyl 4-({[2,5-bis(methyloxy)phenyl]amino}methyl)-3,5-dimethyl-1H-pyrrole-2-carboxylate | 333.4 |

TABLE 1-continued

| Example | Name | MH+ |
|---|---|---|
| 55 | 1-{3-[(6-amino-5-nitropyridin-2-yl)amino]propyl}-4-(2-chlorophenyl)-N-[(2S)-2-hydroxypropyl]-1H-pyrrole-3-carboxamide | 473.9 |
| 56 | (4-methylphenyl)(5-nitro-2-piperidin-1-ylphenyl)methanone | 325.4 |
| 57 | (2S,5R)-N~1~-(4-methylphenyl)-5-phenyl-N~2~-(2-pyridin-2-ylethyl)pyrrolidine-1,2-dicarboxamide | 429.5 |
| 58 | 2-[(3S)-3-(acetylamino)-2-oxopyrrolidin-1-yl]-N-[2-(4-fluorophenyl)ethyl]acetamide | 322.4 |
| 59 | N-[2-(2,4-dichlorophenyl)ethyl]-4-({(Z)-[(4,4-difluorocyclohexyl)imino][(3S)-3-methylpiperazin-1-yl]methyl}amino)benzamide | 553.5 |

TABLE 1-continued

| Example | Structure | Name | MH+ |
| --- | --- | --- | --- |
| 60 | 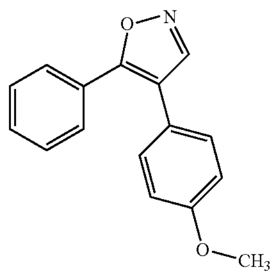 | 4-[4-(methyloxy)phenyl]-5-phenylisoxazole | 252.3 |
| 61 | 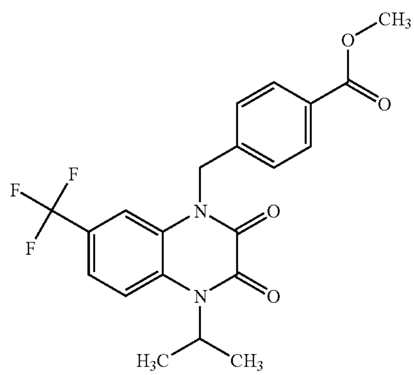 | methyl 4-{[4-(1-methylethyl)-2,3-dioxo-7-(trifluoromethyl)-3,4-dihydroquinoxalin-1(2H)-yl]methyl}benzoate | 421.4 |
| 62 | Chiral | (3beta,16beta)-3,14,16-trihydroxybufa-20,22-dienolide | 403.5 |
| 63 | 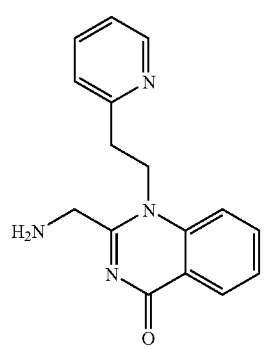 | 2-(aminomethyl)-1-(2-pyridin-2-ylethyl)quinazolin-4(1H)-one | 281.3 |

TABLE 1-continued

| Example | Structure | Name | MH+ |
|---|---|---|---|
| 64 | 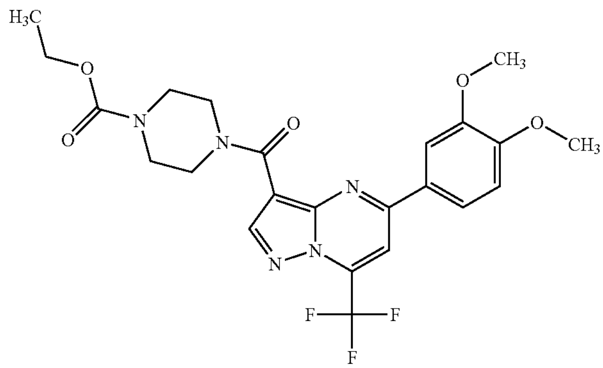 | ethyl 4-{[5-[3,4-bis(methyloxy)phenyl]-7-(trifluoromethyl)pyrazolo[1,5-a]pyrimidin-3-yl]carbonyl}piperazine-1-carboxylate | 508.5 |
| 65 | 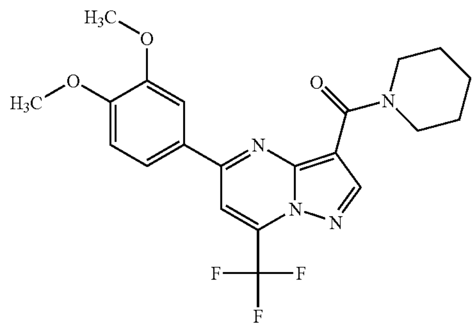 | 5-[3,4-bis(methyloxy)phenyl]-3-(piperidin-1-ylcarbonyl)-7-(trifluoromethyl)pyrazolo[1,5-a]pyrimidine | 435.4 |
| 66 | 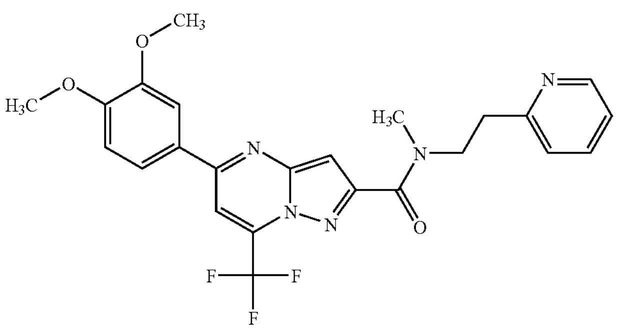 | 5-[3,4-bis(methyloxy)phenyl]-N-methyl-N-(2-pyridin-2-ylethyl)-7-(trifluoromethyl)pyrazolo[1,5-a]pyrimidine-2-carboxamide | 486.5 |
| 67 | 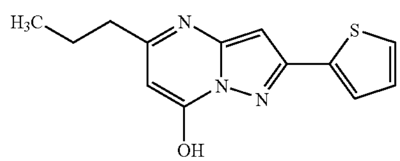 | 5-propyl-2-thien-2-ylpyrazolo[1,5-a]pyrimidin-7-ol | 260.3 |

Biological Methods

Method 1

Candidate small molecule immuno-potentiators can be identified in vitro. Compounds are screened in vitro for their ability to activate immune cells. One marker of such activation is the induction of cytokine production, for example TNF-a production. Apoptosis inducing small molecules may be identified having this activity. These small molecule immuno-potentiators have potential utility as adjuvants and immuno-therapeutics.

In an assay procedure (High Throughput Screening (HTS)) for small molecule immune potentiators (SMIPs), human peripheral blood mononuclear cells (PBMC), 500,000 per mL in RPMI 1640 medium with 10% FCS, were distributed in 96 well plates (100,000 per well) already containing 5 µM of compound in DMSO. The PBMCs were incubated for 18 h at 37° C. in 5% $CO_2$. Their ability to produce cytokines in response to the small molecule compounds is determined using a modified sandwich ELISA.

Briefly supernatants from the PBMC cultures were assayed for secreted TNF using a primary plate bound antibody for capture followed by a secondary biotinylated anti-TNF antibody forming a sandwich. The biotinylated second antibody was then detected using streptavidin-Europium and the amount of bound europium was determined by time resolved fluorescence. SMIP compounds were confirmed by their TNF inducing activity that was measured in the assay as increased Europim counts over cells incubated in RPMI medium alone. "Hits" were selected based on their TNF-inducing activity relative to an optimal dose of lipopolysaccharide LPS (1 µg/ml), a strong TNF inducer. The robustness of the assay and low backgrounds allowed for the routine selection of hits with ~10% of LPS activity that was normally between 5-10× background (cells alone). Selected hits are then subjected to confirmation for their ability to induce cytokines from multiple donors at decreasing concentrations. Those compounds with consistent activity at or below 5 µM are considered confirmed for the purposes of this assay. The assay is readily modified for screening for compounds effective at higher or lower concentrations.

Method 2

Each of Examples 2-67 elicited TNF-a production in human peripheral blood mononuclear cells. Many of the compounds showed activity at less than 20 µM with respect to production of TNF-a. Many of these compounds showed activity at less than 5 µM with respect to production of TNF-a. Many of these compounds showed activity in the production of TNF-a at less than 1.5 µM.

For this reason, each of the R groups of any of the compounds listed in Table 1 are preferred. Additionally, because of the excellent activity of each of the compounds, each of these compounds is individually preferred and is preferred as a member of a group that includes any or all of the other compounds and each compound is preferred in methods of modulating immunopotentiation and in methods of treating biological conditions associated therewith, for example to be used as a vaccine adjuvant. Each of the compounds is also preferred for use in preparation of medicaments for vaccines, immunopotentiation, reducing tumor growth and in treating biological conditions mediated therefrom.

In addition to the procedure described above, methods of measuring other cytokines (e.g. IL1-beta, IL-12, IL-6, IFN-gamma, IL-10 etc.) are well known in the art and can be used to find active SMIP compounds of the present invention.

Compounds may be useful that cause production of TNF-a at higher concentrations, such as 100 µM, 200 µM or 300 µM in the assays described herein. For example Loxoribine causes useful production of TNF-a at 300 µM (see Pope et al Immunostimulatory Compound 7-Allyl-8—Oxoguanosine (Loxoribine) Induces a Distinct Subset of Murine Cytokines Cellular Immunology 162: 333-339 (1995)).

While the invention has been described with respect to specific examples including presently preferred modes of carrying out the invention, those skilled in the art will appreciate that there are numerous variations and permutations of the above described systems and techniques that fall within the spirit and scope of the invention.

What is claimed is:

1. A pharmaceutical vaccine composition comprising a benzazole compound adjuvant and an antigen, wherein said benzazole compound adjuvant is present in an amount effective to enhance the immune response in a subject to the antigen, and wherein the benzazole compound is of formula (XXI):

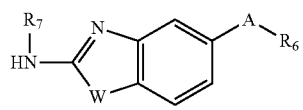

wherein A is —O—;
W is selected from the group consisting of —CH$_2$—, —O—, —S—, —NH—, and —NR$_8$—;
R$_7$ is selected from the group consisting of carbocyclyl, unfused carbocyclylcarbocyclyl, substituted aryl, unsubstituted aryl, substituted heteroaryl, unsubstituted heteroaryl, substituted fused arylheteroaryl, unsubstituted fused arylheteroaryl, substituted unfused arylaryl and unsubstituted unfused arylaryl;
R$_6$ is selected from the group consisting of substituted or unsubstituted aryl, and substituted or unsubstituted heteroaryl; and,
R$_8$ is independently substituted or unsubstituted alkyl, or a pharmaceutically acceptable salt, ester, or prodrug thereof.

2. The pharmaceutical vaccine composition of claim 1, wherein R$_6$ is substituted or unsubstituted pyridine.

3. The pharmaceutical vaccine composition of claim 2, wherein said pyridine is substituted by a carboxamide.

4. The pharmaceutical vaccine composition of claim 1 wherein the antigen is associated with a disease selected from the group consisting of mycobacterial infection, cholera, plague, typhoid, hepatitis B, influenza, polio, rabies, measles, mumps, rubella, yellow fever, tetanus, diphtheria, hemophilus influenzae b, meningococcal infection, and pneumococcal infection.

5. The pharmaceutical vaccine composition according to claim 1 wherein the immune response is the cellular production of one or more cytokines.

6. The pharmaceutical vaccine composition of claim 1, wherein the benzazole compound is selected from the group consisting of:
N-methyl-4-[(2-{[2-(1-methylethyl)phenyl]amino }-1H-benzimidazol-5-yl)oxy]pyridine-2-carboxamide;
N-methyl-4-{[1-methyl-2-({3-[(trimethylsilyl)ethynyl]phenyl}amino)-1H-benzimidazol-5-yl]oxy}pyridine-2-carboxamide;
N-methyl-4-[(1-methyl-2-{[2-(phenylcarbonyl)phenyl]amino }-1H-benzimidazol-5-yl)oxy]pyridine-2-carboxamide;
4-({2-[(4-butylphenyl)amino]-1,3-benzothiazol-5-yl}oxy)-N-methylpyridine-2-carboxamide;
N-methyl-4-(1-methyl-2-[(6-pyrrolidin-1-ylpyridin-3-yl)amino]-1H-benzimidazol-5-yl}oxy)pyridine-2-carboxamide;
4-({2-[1,1'-bi(cyclohexyl)-2-ylamino]-1-methyl-1 H-benzimidazol-5-yl}oxy)-N-methylpyridine-2-carboxamide;
4-({2-[(4-chlorophenyl)amino]-1-methyl-1 H-benzimidazol-5-yl}oxy)-N-1,3-thiazol-2-ylpyridine-2-carboxamide;
4-[(1-methyl-2-{[2-(methyloxy)phenyl]amino}-1H-benzimidazol-5-yl)oxy]-N-[-3-(methyloxy)propyl]pyridine-2-carboxamide; and
4-({2-[(4-ethylphenyl)amino]-1,3-benzoxazol-5-yl}oxy)-N-methylpyridine-2-carboxamide;
or a pharmaceutically acceptable salt thereof.

7. The pharmaceutical vaccine composition of claim 1, wherein the antigen is associated with influenza.

8. The pharmaceutical vaccine composition of claim 1, wherein the antigen comprises haemagglutinin and/or neuraminidase surface protein.

9. The pharmaceutical vaccine composition according to claim 1, further comprising a second adjuvant.

10. The pharmaceutical vaccine composition of claim 9, wherein the second adjuvant is an oil-in-water emulsion.

* * * * *